(12) United States Patent
Mjalli et al.

(10) Patent No.: US 7,820,821 B2
(45) Date of Patent: Oct. 26, 2010

(54) BENZAZOLE DERIVATIVES, COMPOSITIONS, AND METHODS OF USE AS AURORA KINASE INHIBITORS

(75) Inventors: Adnan M. M. Mjalli, Oak Ridge, NC (US); Brian S. Grella, High Point, NC (US); Govindan Subramanian, Bellemeade, NJ (US); Murty N. Arimilli, Oak Ridge, NC (US); Ramesh Gopalaswamy, Jamestown, NC (US); Robert C. Andrews, Jamestown, NC (US); Stephen Davis, Durham, NC (US); Xiaochuan Guo, High Point, NC (US); Jeff Zhu, High Point, NC (US)

(73) Assignee: TransTech Pharma, Inc., High Point, NC (US)

( * ) Notice: Subject to any disclaimer, the term of this patent is extended or adjusted under 35 U.S.C. 154(b) by 380 days.

(21) Appl. No.: 11/704,431

(22) Filed: Feb. 9, 2007

(65) Prior Publication Data

US 2007/0219235 A1 Sep. 20, 2007

Related U.S. Application Data

(60) Provisional application No. 60/772,497, filed on Feb. 10, 2006, provisional application No. 60/791,187, filed on Apr. 11, 2006.

(51) Int. Cl.
*A61K 31/496* (2006.01)
*C07D 401/14* (2006.01)
*C07D 403/14* (2006.01)

(52) U.S. Cl. .................. 544/370; 544/364; 514/254.06

(58) Field of Classification Search .................. 544/370
See application file for complete search history.

(56) References Cited

U.S. PATENT DOCUMENTS

| | | | |
|---|---|---|---|
| 4,925,853 A | 5/1990 | Smith et al. |
| 6,017,919 A | 1/2000 | Inaba et al. |
| 6,114,532 A | 9/2000 | Ries et al. |
| 6,303,600 B1 | 10/2001 | Cox et al. |
| 6,316,474 B1 | 11/2001 | McCauley et al. |
| 6,326,385 B1 | 12/2001 | Wickenden et al. |
| 6,605,632 B1 | 8/2003 | Lesieur et al. |
| 6,872,851 B1 | 3/2005 | Lesieur et al. |
| 6,878,712 B1 | 4/2005 | Butlin et al. |
| 6,951,948 B2 | 10/2005 | Deng et al. |
| 2002/0107245 A1 | 8/2002 | Wagle et al. |
| 2002/0156073 A1 | 10/2002 | Wagle et al. |
| 2003/0109714 A1 | 6/2003 | Wishart et al. |
| 2003/0171411 A1 | 9/2003 | Kodra et al. |
| 2004/0002424 A1 | 1/2004 | Minn et al. |
| 2004/0127492 A1 | 7/2004 | Vazquez et al. |
| 2004/0186148 A1 | 9/2004 | Shankar et al. |
| 2004/0229864 A1 | 11/2004 | Bourrain et al. |
| 2005/0101600 A1 | 5/2005 | Seko et al. |
| 2005/0176760 A1 | 8/2005 | Cezanne et al. |
| 2006/0019967 A1 | 1/2006 | Wu et al. |
| 2006/0068998 A1 | 3/2006 | Negoro et al. |
| 2006/0148855 A1 | 7/2006 | Macdonald et al. |

FOREIGN PATENT DOCUMENTS

| | | |
|---|---|---|
| EP | 0 260 744 | 3/1988 |
| EP | 0 266 326 | 5/1988 |
| EP | 0 385 850 | 9/1990 |
| EP | 1 375 486 | 1/2004 |
| WO | WO 96-39390 | 12/1996 |
| WO | WO 97-03069 | 1/1997 |
| WO | WO 97-11075 | 3/1997 |
| WO | WO 98-02438 | 1/1998 |
| WO | WO 02-39987 | 5/2002 |
| WO | WO 03-007955 | 1/2003 |
| WO | WO 03-053939 | 7/2003 |
| WO | WO 03-082272 | 10/2003 |
| WO | WO 2004-063169 | 7/2004 |
| WO | WO 2004-085425 | 10/2004 |
| WO | WO 2004-087153 | 10/2004 |
| WO | WO 2005-016914 | 2/2005 |
| WO | WO 2005-032548 | 4/2005 |
| WO | WO 2005-035526 | 4/2005 |
| WO | WO 2005-042520 | 5/2005 |
| WO | WO 2005-090379 | 9/2005 |
| WO | WO 2006-086539 | 8/2006 |
| WO | WO 2006-099379 | 9/2006 |

OTHER PUBLICATIONS

Patent Cooperation Treaty, International Preliminary Report on Patentability, International Appl. No. PCT/US2007/003579, Int'l Filing Date Sep. 2, 2007, Mailed Aug. 21, 2008.
Office Action in U.S. Appl. No. 11/374,723 of Mar. 21, 2008.
Prosecution history of U.S. Appl. No. 11/374,723, as of Mar. 11, 2009.
Cockerill et al., "Indazolylamino quinazolines and pyridopyrimidines as inhibitors of the EGFr and c-erB-2" Bioorganic & Medicinal Chemistry Letters, vol. 11, pp. 1401-1405 (2001).
Database Caplus Online, Chemical Abstracts Service, Columbus, Ohio, US; Schwink et al.: "Preparation of N-arylheterocycles as melanin concentrating hormone (MCH) antagonists." XP002439665 retrieved from STN Database accession No. 2004:696342 abstract & WO 2004-072025, Aug. 26, 2004.

(Continued)

*Primary Examiner*—Laura L. Stockton
(74) *Attorney, Agent, or Firm*—Kilpatrick Stockton LLP

(57) ABSTRACT

The present invention relates to compounds and methods from the treatment of cancer. The invention provides compounds that inhibit Aurora kinase, pharmaceutical compositions comprising compounds that inhibit Aurora kinase, and methods for the treatment of cancer using the compounds of the presentation invention or pharmaceutical compositions comprising compounds of the present invention.

28 Claims, 3 Drawing Sheets

OTHER PUBLICATIONS

Database Caplus Online, Chemical Abstracts Service, Columbus, Ohio, US; Inoue et al: "Preparation of isoquinoline and isochroman derivatives for treating virus infectious diseases." XP002439666 retrieved from STN Database accession No. 2003: 796470 abstract & WO 2003-082265; Oct. 9, 2003.

Database Caplus Online, Chemical Abstracts Service, Columbus, Ohio, US; Fuji et al: "Preparation of nitrogen-containing heteroaryl compounds having HIV integrase inhibitory activity." XP002439667 retrieved from STN Database accession No. 2002:695955 abstract & WO 2002-070486; Sep. 12, 2002.

Database Caplus Online, Chemical Abstracts Service, Columbus, Ohio, US; Kubo et al: "Benzimidazole derivatives as neovascularization Inhibitors and pharmaceutical compositions containing them." XP002439668 retrieved from STN Database accession No. 2000:356164 abstract & JP 2000 143635; May 26, 2000.

Database Caplus Online, Chemical Abstracts Service, Columbus, Ohio, US; Das et al: "Preparation of cyclic protein tyrosine kinase inhibitors." XP002447592 retrieved from STN Database accession No. 2000:756524, RN: 302963-85-5 abstract & WO 2000-62778; Oct. 26, 2000.

Database Caplus Online, Chemical Abstracts Service, Columbus, Ohio, US; Garin et al: "Diheterocyclic compounds from dithiocarbamates and derivatives thereof. II. 2, 2'—Diamino-6, 6'-bibenzoazoles." XP002447593 retrieved from STN Database accession No. 1990:440541, RN: 127933-27-1; 127933-2; 127933-29-3; 127933-30-6; 127933-38-4; 127933-39-5; 127933-40-8; 127933-41-9 abstract & Journal of Heterocyclic Chemistry, 27(2); 1990.

Database Caplus Online, Chemical Abstracts Service, Columbus, Ohio, US; Yamamoto et al: "2-p-(Substituted amino) anilinobenzimidazoles." XP002447594 retrieved from STN Database accession No. 1980:111007 RN: 72838-56-3; 72838-64-3 abstract & JP 54081271; Jun. 28, 1979.

International Search Report for related PCT application PCT/US2007/003579, mailed Apr. 9, 2007.

Written Opinion for related PCT application PCT/US2007/003579, mailed Apr. 9, 2007.

Office Action from U.S. Appl. No. 11/374,723 mailed Sep. 2, 2008.

Claims in U.S. Appl. No. 11/374,723 as of Jun. 19, 2009.

Adams, et al., "Chromosomal passengers and the (aurora) ABCs of mitosis," Trends in Cell Biology, vol. 11, No. 2, pp. 49-54(6) (2001). (abstract only).

Bischoff, et al., "The Aurora/Ipl1p kinase family; regulators of chromosome segregation and cytokinesis," Trends in Cell Biology, vol. 9, No. 11, pp. 454-459, (1999). (abstract only).

Chieffi, et al. "Aurora B Expression Directly Correlates with Prostate Cancer Malignancy and Influence Prostate Cell Proliferation," Prostate, vol. 66(3), pp. 326-333 (2006).

Knighton, et al., "Crystal structure of the catalytic subunit of cyclic adenosine monophosphate-dependent protein kinase," Science, vol. 253, No. 5018, pp. 407-414 (1991). (abstract only).

Kuang et al., "Tumour amplified kinase STK15/BTAK induces centrosome amplification, aneuploidy and transformation," Nat Genet., vol. 20(2), pp. 189-193 (1998). (abstract only).

The Protein Kinase Facts Book I, Academic Press, San Diego, Calif., 1995. (Table of Contents and Title Page).

The Protein Kinase Facts Book II, Academic Press, San Diego, Calif., 1995. (Table of Contents and Title Page).

Zhou, et al., "Tumour amplified kinase *STK15/BTAK* induces centrosome amplification, aneuploidy and transformation," Nature Genetics, vol. 20, pp. 189-193 (1998). (abstract only).

Examiner's Report from corresponding European Patent Office (EP Office) Application No. 07 750 418.1 issued on Dec. 1, 2008.

Bischoff et al., The EMBO J. 17(11) 3052-3065 (1998).

Hanks et al., T. FASEB J. 9, 576-596, (1995).

Hiles et al., Cell 70, 419-429 (1992).

Kimura et al., J. Biol. Chem. 274(11), 7334-7340, (1999).

Miyoshi et al., Int. J. Cancer 92, 370-373, (2001).

Sakakura et al., British Journal of Cancer 84(6), 824-831, (2001).

Takahashi et al., Japan J. Cancer Res. 91, 1007-1014, (2000).

Tatsuka et al., Cancer Research 58, 4811-4816, (1998).

Hu et al., Oncol. Res. 15(1), 49-57, (2005).(abstract only).

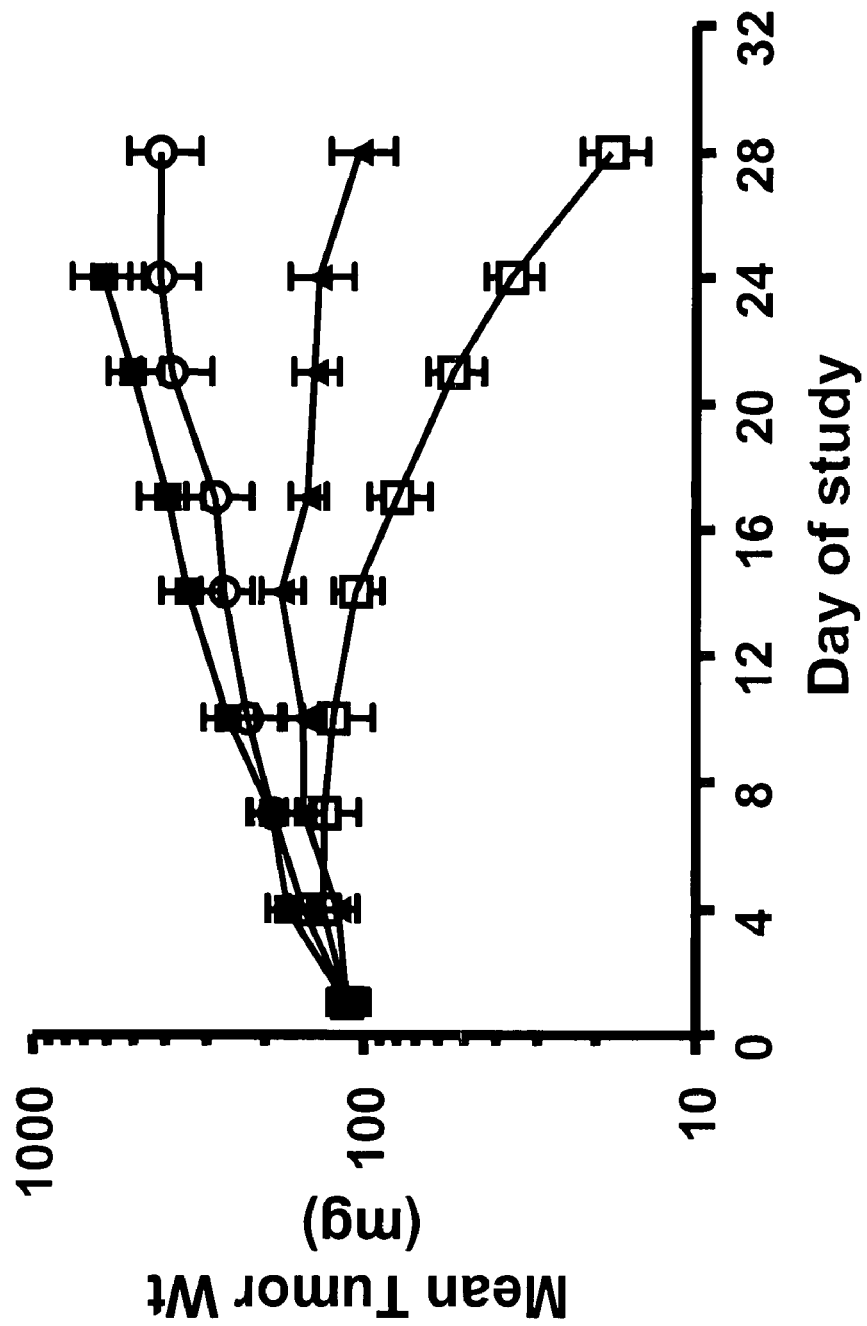

US 7,820,821 B2

BENZAZOLE DERIVATIVES, COMPOSITIONS, AND METHODS OF USE AS AURORA KINASE INHIBITORS

CROSS-REFERENCE TO RELATED APPLICATIONS

This application claims the benefit of priority under 35 U.S.C. §119(e) of U.S. Provisional Application No. 60/772,497, filed Feb. 10, 2006, entitled "Benzazole Derivatives, Compositions, and Methods of Use as Aurora Kinase Inhibitors", and U.S. Provisional Application No. 60/791,187, filed Apr. 11, 2006, entitled "Benzazole Derivatives, Compositions, and Methods of Use as Aurora Kinase Inhibitors", the disclosures of which are herein incorporated by reference in their entirety.

FIELD OF THE INVENTION

The present invention relates to azole derivatives useful as inhibitors of Aurora kinase, and methods of use of the benzazole derivatives to treat cancer.

BACKGROUND OF THE INVENTION

A better understanding of the signal transduction pathways and enzymes underlying disease etiology and pathophysiology has greatly facilitated the search for new therapeutic agents. One important class of enzymes that has been the subject of intensive investigation for targeting disease processes is protein kinases.

Protein kinases are key regulators of cell growth, differentiation, metabolism and function. Protein kinases are a family of structurally related enzymes that are responsible for control of a variety of signal transduction processes within the cell (*The Protein Kinase Facts Book, I and II*, Academic Press, San Diego, Calif.: 1995). Almost all protein kinases contain a catalytic domain consisting of approximately 250 to 300 amino acids. In general, protein kinases mediate their intracellular signaling by catalytic transfer of a γ-phosphoryl group from ATP to target protein substrates. Protein kinases are classified into families by the substrates they phosphorylate. Sequence motifs have been identified that correspond to each of these kinase families such as protein-tyrosine, protein-serine/threonine, and lipids (Hanks, S. K., Hunter, T., FASEB J. 1995, 9 576-596; Knighton et al., Science 1991, 253, 407-414; Hiles et al., Cell 1992, 70, 419-429). In response to a variety of stimuli, protein kinases allow the cell to make decisions by acting as a molecular "on/off" switch that can either perturb or regulate target protein function.

Abnormal protein kinase-mediated signal transduction in a cell is the underlying cause of many pathophysiological states. These disease states include, but are not limited to, autoimmune disease, allergy and asthma diseases, neurological and neurodegenerative diseases, metabolic diseases, Alzheimer's disease, cardiovascular disease, and cancer. Accordingly, protein kinases are considered rational drug targets for therapeutic intervention and protein kinase inhibitors are thought to be effective therapeutic agents.

The aurora family of serine/threonine protein kinases is essential for cell proliferation (Trends in Cell Biology 9, 454-459 (1999); Nat. Rev. Mol. Cell. Biol. 2, 21-32 (2001); Trends in Cell Biology 11, 49-54 (2001)). The human aurora kinase family consists of three highly homologous kinases (A or "2", B or "1" and C or "3"). During normal cell proliferation, these proteins are involved in chromosome segregation, mitotic spindle function, and cytokinesis. Aurora kinase expression is low in resting cells and peaks during the G2 and mitosis phases of the cell cycle. Several proposed mammalian substrates for Aurora kinases that are important for cell division include histone H3, TPX2, myosin II regulatory light chain, CENP-A, and protein phosphatase 1.

Since the elucidation of their key role in mitotic progression and cell division, Aurora kinases have been closely linked to tumorigenesis. For example, Aurora kinase gene amplification and overexpression has been reported in many cancers. A coding single nucleotide polymorphism (SNP) has been identified that is significantly more frequent in advanced gastric cancer relative to early stage gastric cancer, and this SNP correlates with elevated kinase activity (Cancer Lett. Jan. 10, 2006). Overexpression of Aurora A induces centrosome amplification, aneuploidy and transformation in rodent fibroblasts (Bischoff, J. R. et al. EMBO. J 17, 3052-3065 (1998); Nat. Genet. October 20(2):189-93 (1998)). This oncogenic activity is likely due to the generation of chromosome instability. Indeed, there is a strong correlation between Aurora A overexpression and chromosome aneuploidy in breast and gastric cancer. (Int., J. Cancer 92, 370-373 (2001); British Journal of Cancer 84, 824-831 (2001)). Aurora B expression is elevated in cell lines derived from tumors of the colon, breast, lung, melanoma, kidney, ovary, pancreas, CNS, gastric tract and leukemias (Oncol Res. 2005; 15(1):49-57; Tatsuka et al. 1998, 58, 4811-4816; British Journal of Cancer 84, 824-831 (2001); EMBO J. 17, 3052-3065 (1998)). In prostate cancer, increased nuclear expression of Aurora B was observed in high Gleason grade anaplastic prostate cancer tissues relative to low and intermediate grades, and Aurora B expression was accompanied by the phosphorylation of the histone H3 substrate (Prostate 66(3): 326-33 (2003)). Aurora C is overexpressed in primary colorectal cancer (Journal of Biological Chemistry 274, 7334-7340 (1999); Jpn. J. Cancer Res. 91, 1007-1014 (2000)).

Because Aurora kinase inhibition in tumor cells can result in mitotic arrest and apoptosis, these kinases are important targets for cancer therapy. Given the central role of mitosis in the progression of virtually all malignancies, inhibitors of the Aurora kinases therefore are expected to have the potential to block growth of cancers or tumors and have application across a broad range of human cancers or tumors.

SUMMARY OF THE INVENTION

This invention provides substituted benzazole derivatives and compositions that inhibit Aurora kinase. In an embodiment, the present invention provides compounds of Formula (I) as depicted below. In another embodiment, the present invention provides methods of preparation of compounds of Formula (I). In another embodiment, the present invention provides pharmaceutical compositions comprising the compounds of Formula (I). In another embodiment, the present invention provides methods of using the compounds of Formula (I) and pharmaceutical compositions comprising a compound of Formula (I) in treating human or animal disorders. The compounds of the invention are useful as inhibitors of Aurora kinase and thus may be useful for the management, treatment, control and adjunct treatment of diseases mediated by Aurora kinase activity such as cell proliferative disorders, including cancer.

Figure 2:
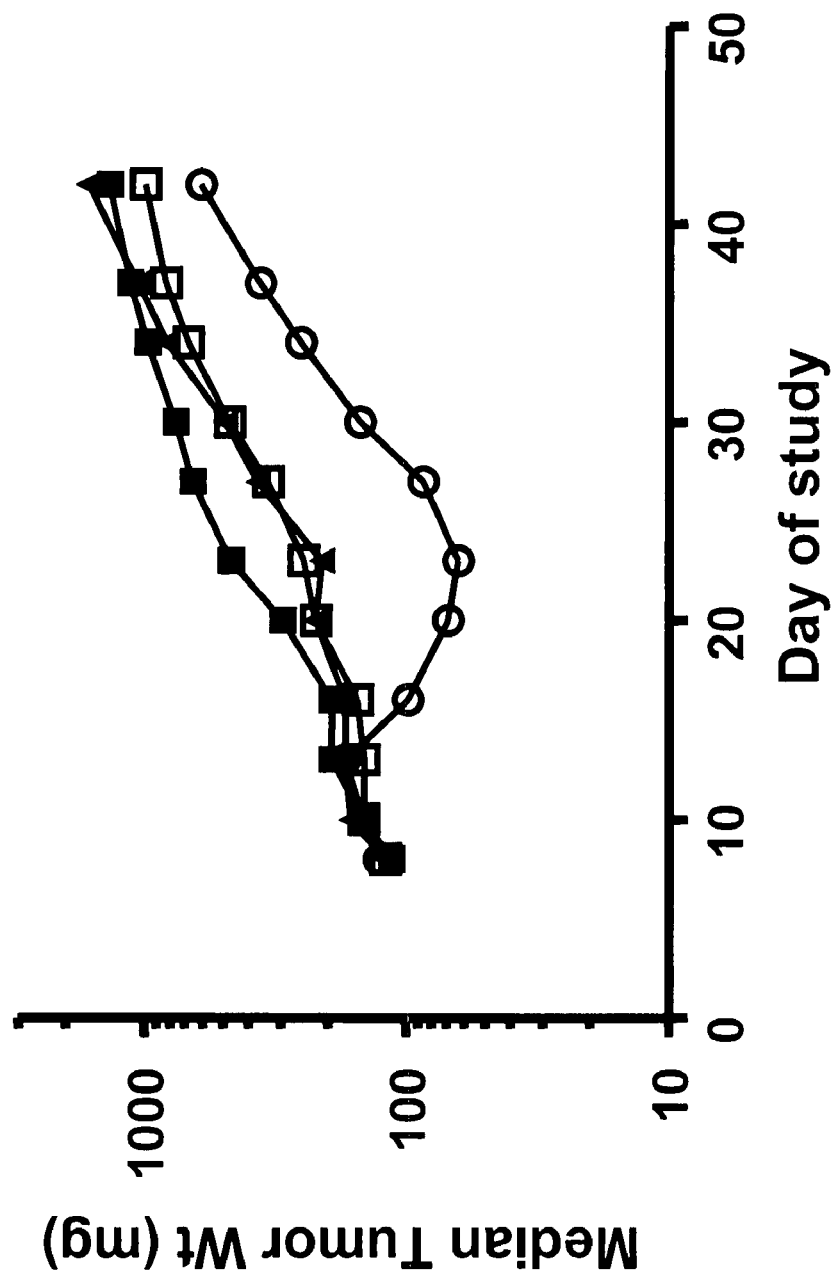

FIG. 2 shows MiaPaCa-2 tumor growth curves, where ■ represents vehicle for Example 88 and gemcitabine; ▲ represents Example 88 at a dose of 10 mg/kg, i.p., b.i.d. daily for 10 days; □ represents gemcitabine at as dose of 120 mg/kg, i.p., q3d×4; and ○ represents Example 88 and gemcitabine.

FIG. 3 shows BT-474 tumor growth curves in athymic SCID mice, where ■ represents vehicle for Example 88; ○ represents trastuzumab at a dose of 10 mg/kg, i.p., twice weekly, for 4 weeks; ▲ represents Example 88 at a dose of 30 mg/kg, i.p., b.i.d. daily for 3 days, then 2 days off, for a total of 5 cycles; and □ represents Example 89 and trastuzumab.

DETAILED DESCRIPTION OF THE INVENTION

The present invention provides compounds that inhibit Aurora kinase. These compounds are useful for inhibiting Aurora kinase in vitro, and may be useful for the treatment of cell proliferative disorders, including cancer in a patient.

In one aspect, the present invention provides a compound of Formula (I):

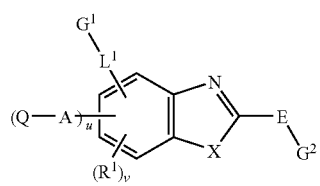

wherein
X is —NH—, —O—, or —S—,
E is —CH$_2$—, —NH—, —O—, or —S—,
$G^1$ and $G^2$ are independently selected from the group consisting of: aryl, heteroaryl, fused arylcycloalkyl, fused cycloalkylaryl, fused cycloalkylheteroaryl, fused heterocyclylaryl, and fused heterocyclylheteroaryl group, wherein $G^1$ and $G^2$ are optionally substituted 1 to 7 times with substituents independently selected from the group consisting of $R^b$;
$L^1$ is selected from the group consisting of: a direct bond, —CH$_2$—, —O—, —O—CH$_2$—, —CH$_2$—O—, —N(R$^6$)—, —C(O)—, —C(O)N(R$^6$)—, —N(R$^6$)C(O)—, —N(R$^6$)C(O)N(R$^7$)—, —N(R$^6$)C(O)O—, —OC(O)N(R$^6$)—, —N(R$^6$)SO$_2$—, —SO$_2$N(R$^6$)—, —C(O)—O—, —O—C(O)—, —S—, —S(O)—, —S(O)$_2$—, —N(R$^6$)SO$_2$N(R$^7$)—, —N=N—, —C(R$^8$)=C(R$^9$)—, and —C≡C—,
wherein
$R^6$ and $R^7$ are independently selected from the group consisting of $R^d$ and $R^e$; and
$R^8$ and $R^9$ are independently selected from the group consisting of $R^e$ and $R^f$;
A is a direct bond or the group -L$^2$-Y-L$^3$-, wherein
$L^2$ and $L^3$ are independently selected from the group consisting of:
a direct bond,
—C$_{1-10}$ alkylene,
—C$_{2-10}$ alkenylene,
—C$_{2-10}$ alkynylene,
-arylene,
-heteroarylene,
-cycloalkylene, and
-heterocyclylene,
wherein the carbon atoms of the alkylene, alkenylene, alkynylene, arylene, heteroarylene, cycloalkylene, and heterocyclylene groups are optionally substituted 1-4 times with a substituent independently selected from R$^c$;
Y is a direct bond, —O—, —N(R$^{10}$), —S—, SO$_2$—, —C(O)N(R$^{10}$)—, —N(R$^{10}$)—C(O)—, —N(R$^{11}$)C(O)N(R$^{10}$)—, —N(R$^{10}$)SO$_2$—, —SO$_2$N(R$^{10}$)—, —C(O)—O—, —N(R$^{11}$)SO$_2$N(R$^{10}$)—, —O—CO—, or —N=N—,
wherein
$R^{10}$ and $R^{11}$ are independently selected from the group consisting of: $R^d$ and $R^e$, and
Q is selected from the group consisting of

1)

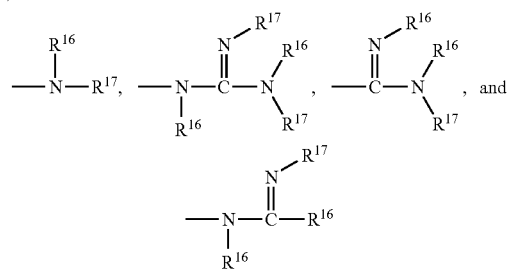

wherein $R^{16}$ and $R^{17}$ are independently selected from the group consisting of: $R^d$ and $R^e$;

2) -heteroaryl;
-heterocyclyl;
-fused cycloalkylheteroaryl;
-fused heterocyclylaryl;
-fused heterocyclylheteroaryl;
-fused arylheterocyclyl;
-fused heteroarylcycloalkyl; and
-fused heteroarylheterocyclyl;
wherein the heteroaryl, heterocyclyl, fused cycloalkylheteroaryl, fused heterocyclylaryl, fused heterocyclylheteroaryl, fused arylheterocyclyl, fused heteroarylcycloalkyl, and fused heteroarylheterocyclyl groups are optionally substituted 1-4 times with a substituent independently selected from R$^c$; and 3) a ring system comprising at least one nitrogen atom selected from the group consisting of:

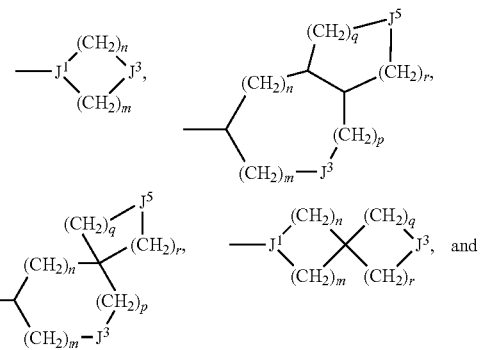

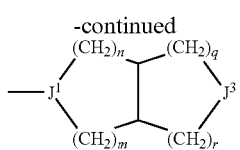

wherein
n, m, p, q and r are independently 0-4 such that n+m+p equals from 2-5 and q+r equals from 2-5, and the cycloalkyl or heterocyclo ring system is optionally substituted on the ($CH_2$) carbon atoms 1-2 with $R^{18}$ or $R^{19}$, wherein $R^{18}$ and $R^{19}$ are independently selected from the group consisting of $R^f$ and $R^g$, $J^1$ is selected from the group consisting of:

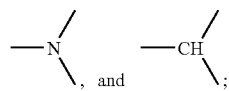

$J^3$ and $J^5$ are independently selected from the group consisting of —$CH_2$—, —O—, —S—, —$S(O)_2$—, —C(O)—, —C(O)N(H)—, —NHC(O)—, —NHC(O)N(H)—, —$NHSO_2$—, —$SO_2N(H)$—, —C(O)—O—, —O—C(O)—, —$NHSO_2NH$—,

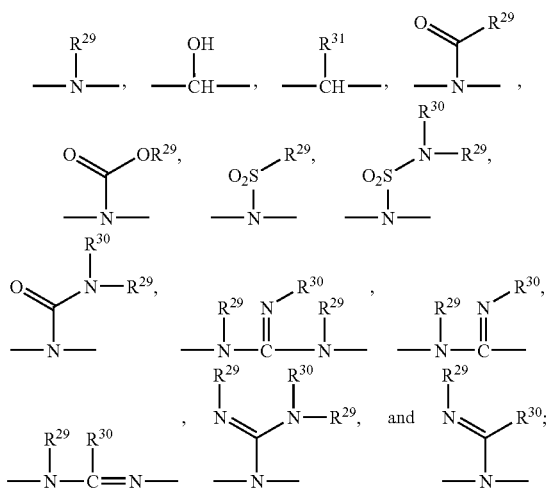

$R^{29}$ and $R^{30}$ are independently selected from the group consisting of $R^d$ and $R^e$;

$R^{31}$ is $R^f$;

$R^1$ is $R^b$;

$R^b$ is
a) -cycloalkyl,
b) -cyano,
c) —$OR^d$,
d) —$NO_2$,
e) -halogen,
f) -haloalkyl,
g) —$S(O)_sR^d$,
h) —$SR^d$,
i) —$S(O)_2OR^d$,
j) —$S(O)_sNR^dR^e$,
k) —$NR^dR^e$,
l) —$O(CR^fR^g)_tNR^dR^e$,
m) —$C(O)R^d$,
n) —$CO_2R^d$,
o) —$CO_2(CR^fR^g)_tC(O)NR^dR^e$,
p) —$OC(O)R^d$,
q) —$C(O)NR^dR^e$,
r) —$NR^dC(O)R^e$,
s) —$OC(O)NR^dR^e$,
t) —$NR^dC(O)OR^e$,
u) —$NR^dC(O)NR^dR^e$,
v) —$CF_3$,
w) —$OCF_3$
x) —$C_{1-10}$ alkyl,
y) —$C_{2-10}$ alkenyl,
z) —$C_{2-10}$ alkynyl,
aa) —$C_{1-10}$ alkylene-aryl,
bb) —$C_{1-10}$ alkylene-heteroaryl, or
cc) -heteroaryl,
wherein alkyl, alkenyl, alkynyl, aryl, heteroaryl, and cycloalkyl groups are optionally substituted 1-4 times with a substituent independently selected from $R^c$;

$R^c$ is
a) -halogen,
b) -amino,
c) -carboxy,
d) —$C_{1-4}$ alkyl,
e) —O—$C_{1-4}$ alkyl,
f) -cycloalkyl,
g) —O-cycloalkyl,
h) -aryl,
i) —$C_{1-4}$ alkylene-aryl,
j) -hydroxy,
k) —$CF_3$,
l) —O-aryl,
m) -heteroaryl,
n) -heteroaryl-$C_{1-10}$ alkyl,
o) heterocyclyl,
p) —$CO_2$—$C_{1-10}$ alkyl, or
q) —$CO_2$—$C_{1-10}$ alkyl-aryl, $R^d$ and $R^e$ are independently selected from hydrogen, $C_{1-10}$ alkyl, $C_{2-10}$ alkenyl, $C_{2-10}$ alkynyl, cycloalkyl, —$C_{1-10}$ alkylene-cycloalkyl, aryl, heterocyclyl, wherein alkyl, alkenyl, alkynyl, cycloalkyl, aryl, heterocyclyl groups are optionally substituted with one to four substituents independently selected from $R^c$; or $R^d$ and $R^e$ together with the atoms to which they are attached form a heterocyclic ring of 5 to 7 members containing 0-2 additional heteroatoms independently selected from oxygen, sulfur and nitrogen and optionally substituted with 1-3 times with $R^c$, $R^f$ and $R^g$ are independently selected from hydrogen, $C_{1-10}$ alkyl, cycloalkyl, —$C_{1-10}$ alkylene-cycloalkyl, and aryl, wherein alkyl, cycloalkyl, and aryl groups are optionally substituted with one to four substituents independently selected from $R^c$; or $R^f$ and $R^g$ together with the carbon to which they are attached form a ring of 5 to 7 members containing 0-2 heteroatoms independently selected from oxygen, sulfur and nitrogen optionally substituted with 1-3 times with $R^c$, s is an integer from 1 to 2,
t is an integer from 1 to 10,
u is an integer from 0 to 1,
v is an integer from 0 to 2, or a pharmaceutically acceptable salt or prodrug thereof.

In an embodiment, X is —NH—.
In another embodiment, X is —NH— and E is —NH—.
In an embodiment of the compound of Formula (I), $G^2$ is selected from the group consisting of: phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, and 4,5,6,7-tetrahydro-thiazolo[5,4-c]-pyridine-2-yl,
wherein $G^2$ is optionally substituted 1-4 times with a substituent selected from the group consisting of $R^b$.

In a further embodiment, $G^2$ is substituted with at least one substituent selected from the group consisting of: halo, phenyl, $C_{1-10}$ alkyl, piperazine-1-yl, 4-($C_{1-10}$ alkyl)-piperazine-1-yl, $C_{1-10}$ alkoxy, haloalkyl, cycloalkyl, and $C_{1-10}$ alkylene-cycloalkyl.

In a further embodiment, $G^2$ is phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, wherein G is unsubstituted or substituted with at least one substituent selected from the group consisting of: chloro, fluoro, methyl, ethyl, propyl, isopropyl, tert-butyl, butyl, phenyl, methoxy, trifluoromethyl, trifluoromethoxy, and cyclopentyl.

In an embodiment of the compound of Formula (I), $L^1$ is —C(O)—NH— or —NH—C(O)—.

In another embodiment of the compound of Formula (I), $L^1$ is —C($R^8$)═C($R^9$)—.

In another embodiment of the compound of Formula (I), $G^1$ is selected from the group consisting of:
phenyl,
pyrazole-3-yl,
benzothiazole-5-yl, benzothiazole-6-yl,
benzimidazole-5-yl, benzimidazole-6-yl,
benzoxazole-5-yl, benzoxazole-6-yl,
benzotriazole-5-yl, benzotriazole-6-yl,
benzoisoxazole-5-yl, benzoisoxazole-6-yl,
indole-5-yl, indole-6-yl,
2H-indazole-6-yl,
1H-indazole-3-yl, 1H-indazole-4-yl, 1H-indazole-5-yl, 1H-indazole-6-yl,
quinoline-6-yl, quinoline-7-yl,
quinazoline-4-yl,
2-oxindole-5-yl, 2-oxindole-6-yl,
2-(1H)-benzimidazolone-5-yl,
3-indazolinone-5-yl, and 3-indazolinone-6-yl,
wherein $G^1$ is optionally substituted 1-4 times with a substituent selected from the group consisting of $R^b$.

In a further embodiment, G1 is unsubstituted or substituted with at least one group selected from the group consisting of: halo, phenyl, $C_{1-10}$ alkyl, piperazine-1-yl, 4-($C_{1-10}$ alkyl)-piperazine-1-yl, —$C_{1-10}$ alkoxy, —$C_{1-10}$ alkylene-OH, -haloalkyl, -cycloalkyl, —$C_{1-10}$ alkylene-cycloalkyl, morpholine-4-yl, —$C_{1-10}$-alkylene-morpholine-4-yl, pyrrole-1-yl, -amino, —NH—($C_{1-10}$ alkyl), —N($C_{1-10}$ alkyl)$_2$, —NHC(O)—$C_{1-10}$ alkyl, —NHC(O)-(1-($C_{1-10}$ alkyl)-piperidine-4-yl), —NHC(O)-phenyl, —NH—$C_{1-10}$ alkylene-morpholine-4-yl, —O—$C_{1-10}$ alkylene-morpholine-4-yl, and —NH—$C_{1-10}$ alkylene-OH.

In a further embodiment, $L^1$ is —NHC(O)— or —C(O)—NH— and $G^1$ is 1H-indazole-5-yl or 1H-indazole-6-yl, wherein $G^1$ is optionally substituted 1-4 times with a substituent selected from the group consisting of $R^b$.

In a further embodiment, $G^1$ is 1H-indazole-5-yl or 1H-indazole-6-yl, wherein $G^1$ is unsubstituted or substituted at the 3-position with a substituent selected from the group consisting of: halo, phenyl, $C_{1-10}$ alkyl, piperazine-1-yl, 4-($C_{1-10}$ alkyl)-piperazine-1-yl, —$C_{1-10}$ alkoxy, —$C_{1-10}$ alkylene-OH, -haloalkyl, -cycloalkyl, —$C_{1-10}$ alkylene-cycloalkyl, morpholine-4-yl, —$C_{1-10}$-alkylene-morpholine-4-yl, pyrrole-1-yl, -amino, —NH—($C_{1-10}$ alkyl), —N($C_{1-10}$ alkyl)$_2$, —NHC(O)—$C_{1-10}$ alkyl, —NHC(O)-(1-($C_{1-10}$ alkyl)-piperidine-4-yl), —NHC(O)-phenyl, —NH—$C_{1-10}$ alkylene-morpholine-4-yl, —O—$C_{1-10}$ alkylene-morpholine-4-yl, and —NH—$C_{1-10}$ alkylene-OH.

In another embodiment, u is 1, A is a direct bond, and Q is selected from the group consisting of:
4-($C_{1-10}$ alkyl)-piperazine-1-yl,
piperadine-1-yl,
morpholine-4-yl,
—NH—$C_{1-10}$ alkyl,
—N—($C_{1-10}$ alkyl)$_2$,
—N—($C_{1-10}$ alkyl)(cycloalkyl), and
—NH-cycloalkyl.

In an embodiment, u is zero and v is zero. In another embodiment, u is 1 and v is zero.

In another embodiment, u is zero and v is one.

In another embodiment, u is zero and v is one, and $R^1$ is selected from the group consisting of:
—$C_{1-10}$ alkyl,
-cycloalkyl,
—$C_{1-10}$ alkylene-cycloalkyl,
—$C_{1-10}$ haloalkyl,
-phenyl,
—O—$C_{1-10}$ alkyl,
—O-cycloalkyl, and
—O—$C_{1-10}$ haloalkyl.

In another embodiment, X is —NH—, E is —NH—, v is zero, $L^1$ is —NHC(O)— or —C(O)NH—, $G^1$ is 1H-indazol-6-yl or 1H-indazol-5-yl, wherein $G^1$ optionally substituted 1-4 times with a substituent selected from the group consisting of $R^b$. In another embodiment, $G^1$ is unsubstituted.

In another embodiment, the compound of Formula (I) has the formula:

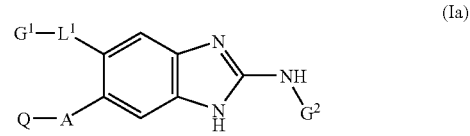

(Ia)

wherein
$G^1$, $G^2$, $L^1$, Q, and A are as defined above.

In another embodiment, the compound of Formula (I) has the formula:

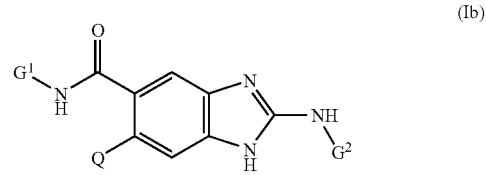

(Ib)

wherein
$G^1$, $G^2$, and Q are as defined above.

In a further embodiment of Formula (Ib), Q is selected from the group consisting of: 4-($C_{1-10}$ alkyl)-piperazine-1-yl, piperadine-1-yl, morpholine-4-yl, —N—($C_{1-10}$ alkyl, —N—($C_{1-10}$ alkyl)$_2$, —N—($C_{1-10}$ alkyl)(cycloalkyl), and —NH-cycloalkyl.

In a further embodiment of Formula (Ib), Q is selected from the group consisting of: morpholine-4-yl, 4-methyl-piperazine-1-yl, diethylamino, 2,6-dimethylmorpholine-4-yl, (2-dimethylaminoethyl)-methylamino, 4-dimethylaminopiperidine-1-yl, dipropylamino, bis-(2-methoxyethyl)amino, 4-hydroxypiperidine-1-yl, ethyl-(2-methoxyethyl)amino, pyrrolidine-1-yl, N-ethyl-N'-(2-methoxyethyl)amino, ethylpropylamino, 4-isopropylpiperazine-1-yl, and ethylmethylamino.

In a further embodiment of Formula (Ib), $G^2$ is selected from the group consisting of: phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, and 4,5,6,7-tetrahydro-thiazolo[5,4-c]-pyridine-2-yl, wherein $G^2$ is optionally substituted 1-4 times with a substituent selected from the group consisting of $R^b$.

In a further embodiment of Formula (Ib), $G^2$ is selected from the group consisting of: phenyl and pyridine-2-yl, wherein $G^2$ is unsubstituted or substituted with at least one substituent selected from the group consisting of: methyl, methoxy, trifluoromethyl, and trifluoromethoxy.

In a further embodiment of Formula (Ib), $G^1$ is selected from the group consisting of: phenyl, pyrazole-3-yl, benzothiazole-5-yl, benzothiazole-6-yl, benzimidazole-5-yl, benzimidazole-6-yl, benzoxazole-5-yl, benzoxazole-6-yl, benzotriazole-5-yl, benzotriazole-6-yl, benzoisoxazole-5-yl, benzoisoxazole-6-yl, indole-5-yl, indole-6-yl, 2H-indazole-6-yl, 1H-indazole-3-yl, 1H-indazole-4-yl, 1H-indazole-5-yl, 1H-indazole-6-yl, quinoline-6-yl, quinoline-7-yl, quinazoline-4-yl, 2-oxindole-5-yl, 2-oxindole-6-yl, 2-(1H)-benzimidazolone-5-yl, 3-indazolinone-5-yl, and 3-indazolinone-6-yl, wherein $G^1$ is optionally substituted 1-4 times with a substituent selected from the group consisting of $R^b$.

In another embodiment, the compound of Formula (I) has the formula:

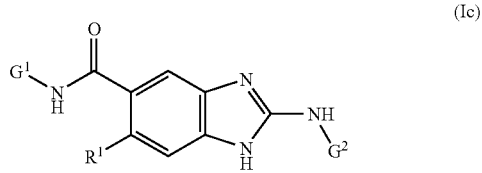

(Ic)

wherein $G^1$, $G^2$, and $R^1$ are as defined above.

In a further embodiment of the compound of Formula (Ic), $R^1$ is selected from the group consisting of: —$C_{1-10}$ alkyl, -cycloalkyl, —$C_{1-10}$ alkylene-cycloalkyl, —$C_{1-10}$ haloalkyl, -phenyl, —O—$C_{1-10}$ alkyl, —O-cycloalkyl, and —O—$C_{1-10}$ haloalkyl.

In a further embodiment of Formula (Ic), $G^2$ is selected from the group consisting of: phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, and 4,5,6,7-tetrahydro-thiazolo[5,4-c]-pyridine-2-yl, wherein G is optionally substituted 1-4 times with a substituent selected from the group consisting of $R^b$.

In a further embodiment of Formula (Id), $G^1$ is selected from the group consisting of: phenyl, pyrazole-3-yl, benzothiazole-5-yl, benzothiazole-6-yl, benzimidazole-5-yl, benzimidazole-6-yl, benzoxazole-5-yl, benzoxazole-6-yl, benzotriazole-5-yl, benzotriazole-6-yl, benzoisoxazole-5-yl, benzoisoxazole-6-yl, indole-5-yl, indole-6-yl, 2H-indazole-6-yl, 1H-indazole-3-yl, 1H-indazole-4-yl, 1H-indazole-5-yl, 1H-indazole-6-yl, quinoline-6-yl, quinoline-7-yl, quinazoline-4-yl, 2-oxindole-5-yl, 2-oxindole-6-yl, 2-(1H)-benzimidazolone-5-yl, 3-indazolinone-5-yl, and 3-indazolinone-6-yl, wherein G1 is optionally substituted 1-4 times with a substituent selected from the group consisting of $R^b$.

In the compounds of Formula (I), the various functional groups represented should be understood to have a point of attachment at the functional group having the hyphen. In other words, in the case of —$C_{1-10}$ alkylene-aryl, it should be understood that the point of attachment is the alkylene group; an example would be benzyl. In the case of a group such as —C(O)—NH—$C_{1-10}$ alkylene-aryl, the point of attachment is the carbonyl carbon.

The term "Aurora kinase inhibitor" or "inhibitor of Aurora kinase" is used to signify a compound having a structure as defined herein, which is capable of interacting with an Aurora kinase and inhibiting its enzymatic activity. Inhibiting Aurora kinase enzymatic activity means reducing the ability of an Aurora kinase to phosphorylate a substrate peptide or protein. In various embodiments, such reduction of Aurora kinase activity is at least about 50%, at least about 75%, at least about 90%, at least about 95%, or at least about 99%. In various embodiments, the concentration of Aurora kinase inhibitor required to reduce an Aurora kinase enzymatic activity is less than about 1 µM, less than about 500 nM, or less than about 100 nM.

In some embodiments, such inhibition is selective, i.e., the Aurora kinase inhibitor reduces the ability of an Aurora kinase to phosphorylate a substrate peptide or protein at a concentration that is lower than the concentration of the inhibitor that is required to produce another, unrelated biological effect, e.g., reduction of the enzymatic activity of a different kinase.

As used herein, the term "comprises" means "includes, but is not limited to."

Also included within the scope of the invention are the individual enantiomers of the compounds represented by Formula (I) above as well as any wholly or partially racemic mixtures thereof. The present invention also covers the individual enantiomers of the compounds represented by Formula (I) above as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C— or $^{14}$C-enriched carbon are within the scope of the invention.

In another aspect, the present invention provides a pharmaceutically acceptable salt, solvate, or prodrug of compounds of Formula (I). In an embodiment, the prodrug comprises a biohydrolyzable ester or biohydrolyzable amide of a compound of Formula (I).

Examples of compounds of Formula (I) of the present invention having potentially useful biological activity are listed by name below in Table 1. The ability of compounds Formula (I) to inhibit Aurora kinase activity was established with representative compounds of Formula (I) listed in Table 1 using the peptide phosphorylation assay described in Example 102. The compounds of Formula (I) in Table 1 may inhibit Aurora Kinase with an IC$_{50}$ of less than or equal to 1 microMolar (µM; $10^{-6}$ M).

Compounds that inhibit Aurora kinase activity are potentially useful in treating cell proliferative disorders. The compounds of Formula (I) of the present invention may therefore be particularly useful in the treatment of cancer.

TABLE 1

| Ex. | Name |
|---|---|
| 1 | 2-(Isoquinolin-3-ylamino)-1H-benzimidazole-5-carboxylic acid benzothiazol-6-ylamide |
| 2 | 2-(Isoquinolin-3-ylamino)-1H-benzimidazole-5-carboxylic acid (1H-indazol-5-yl)-amide |
| 3 | 2-(Pyridin-2-ylamino)-1H-benzimidazole-5-carboxylic acid (1H-indazol-5-yl)-amide |
| 4 | 2-(Pyridin-2-ylamino)-1H-benzimidazole-5-carboxylic acid (2-methyl-benzooxazol-5-yl)-amide |
| 5 | 2-(Pyridin-2-ylamino)-1H-benzimidazole-5-carboxylic acid (1H-indazol-6-yl)-amide |
| 6 | 2-(Pyridin-3-ylamino)-1H-benzimidazole-5-carboxylic acid (1H-indazol-6-yl)-amide |
| 7 | 2-(Pyridin-2-ylamino)-1H-benzimidazole-4-carboxylic acid benzothiazol-6-ylamide |
| 8 | 2-(Pyridin-2-ylamino)-1H-benzimidazole-5-carboxylic acid (1H-benzotriazol-5-yl)-amide |
| 9 | 2-(2,4-Dichlorophenylamino)-3H-benzimidazole-5-carboxylic acid (1-methyl-1H-indazol-5-yl)-amide |
| 10 | 2-(2,4-Dichlorophenylamino)-3H-benzimidazole-5-carboxylic acid (1H-indazol-5-yl)-amide |
| 11 | 2-Phenylamino-1H-benzimidazole-5-carboxylic acid (1H-indazol-5-yl)-amide |
| 12 | 2-Phenylamino-1H-benzimidazole-5-carboxylic acid (1H-indazol-6-yl)-amide |
| 13 | 2-(Pyridin-4-ylamino)-1H-benzimidazole-5-carboxylic acid (1H-indazol-6-yl)-amide |
| 14 | 2-(Thiazol-2-ylamino)-1H-benzimidazole-5-carboxylic acid (1H-indazol-6-yl)-amide |
| 15 | 2-Phenylamino-1H-benzimidazole-5-carboxylic acid (1H-benzotriazol-5-yl)-amide |
| 16 | 2-(Pyridin-2-ylamino)-1H-benzimidazole-5-carboxylic acid (1-methyl-1H-indazol-5-yl)-amide |
| 17 | 2-(2-Chlorophenylamino)-1H-benzimidazole-5-carboxylic acid (1H-indazol-6-yl)-amide |
| 18 | 2-(4,5-Dimethylthiazol-2-ylamino)-1H-benzimidazole-5-carboxylic acid (1H-indazol-6-yl)-amide |
| 19 | 2-(2,4-Dichlorophenylamino)-1H-benzimidazole-5-carboxylic acid (1H-indazol-6-yl)-amide |
| 20 | 2-(Benzothiazol-2-ylamino)-1H-benzimidazole-5-carboxylic acid (1H-indazol-6-yl)-amide |
| 21 | 2-(4-Phenylthiazol-2-ylamino)-1H-benzimidazole-5-carboxylic acid (1H-indazol-6-yl)-amide |
| 22 | 2-(2-Fluorophenylamino)-3H-benzimidazole-5-carboxylic acid (1H-indazol-6-yl)-amide |
| 23 | 2-(2-Ethylphenylamino)-1H-benzimidazole-5-carboxylic acid (1H-indazol-6-yl)-amide |
| 24 | 2-(2,4-Dichlorophenylamino)-3H-benzimidazole-5-carboxylic acid (1H-benzotriazol-5-yl)-amide |
| 25 | 2-(1-Isopropyl-1H-imidazol-2-ylamino)-3H-benzimidazole-5-carboxylic acid (1H-indazol-6-yl)-amide |
| 26 | 2-(2,4-Dimethylphenylamino)-3H-benzimidazole-5-carboxylic acid (1H-indazol-6-yl)-amide |
| 27 | 2-(2-Isopropylphenylamino)-3H-benzimidazole-5-carboxylic acid (1H-indazol-6-yl)-amide |
| 28 | 2-(4-Chlorophenylamino)-3H-benzimidazole-5-carboxylic acid (1H-indazol-6-yl)-amide |
| 29 | 2-(Naphthalen-1-ylamino)-3H-benzimidazole-5-carboxylic acid (1H-indazol-6-yl)-amide |
| 30 | 2-(2-tert-Butylphenylamino)-3H-benzimidazole-5-carboxylic acid (1H-indazol-6-yl)-amide |
| 31 | 2-(Biphenyl-2-ylamino)-3H-benzimidazole-5-carboxylic acid (1H-indazol-6-yl)-amide |
| 32 | 2-(2-Propylphenylamino)-3H-benzimidazole-5-carboxylic acid (1H-indazol-6-yl)-amide |
| 33 | 2-(2,5-Dichlorophenylamino)-3H-benzimidazole-5-carboxylic acid (1H-indazol-6-yl)-amide |
| 34 | 2-(2-Methoxyphenylamino)-3H-benzimidazole-5-carboxylic acid (1H-indazol-6-yl)-amide |
| 35 | 2-(2-Trifluoromethylphenylamino)-3H-benzimidazole-5-carboxylic acid (1H-indazol-6-yl)-amide |
| 36 | 2-(3-Methylpyridin-2-ylamino)-3H-benzimidazole-5-carboxylic acid (1H-indazol-6-yl)-amide |
| 37 | 2-(2-Trifluoromethoxyphenylamino)-3H-benzimidazole-5-carboxylic acid (1H-indazol-6-yl)-amide |
| 38 | 2-(3-Fluorophenylamino)-3H-benzimidazole-5-carboxylic acid (1H-indazol-6-yl)-amide |

TABLE 1-continued

| Ex. | Name |
|---|---|
| 39 | 2-(4-Fluorophenylamino)-3H-benzimidazole-5-carboxylic acid (1H-indazol-6-yl)-amide |
| 40 | 2-(3,5-Difluorophenylamino)-3H-benzimidazole-5-carboxylic acid (1H-indazol-6-yl)-amide |
| 41 | 2-(2-Butylphenylamino)-3H-benzimidazole-5-carboxylic acid (1H-indazol-6-yl)-amide |
| 42 | 2-(3-Ethyl-6-methyl-pyridin-2-ylamino)-3H-benzimidazole-5-carboxylic acid (1H-indazol-6-yl)-amide |
| 43 | 2-(5-Chloro-2-methyl-phenylamino)-3H-benzimidazole-5-carboxylic acid (1H-indazol-6-yl)-amide |
| 44 | 2-(3-Fluoro-2-methyl-phenylamino)-3H-benzimidazole-5-carboxylic acid (1H-indazol-6-yl)-amide |
| 45 | 2-(5-Fluoro-2-methyl-phenylamino)-3H-benzimidazole-5-carboxylic acid (1H-indazol-6-yl)-amide |
| 46 | 2-(3-Chloro-2-methyl-phenylamino)-3H-benzimidazole-5-carboxylic acid (1H-indazol-6-yl)-amide |
| 47 | 2-(1-Cyclopentyl-1H-imidazol-2-ylamino)-3H-benzimidazole-5-carboxylic acid (1H-indazol-6-yl)-amide |
| 48 | 2-(2-Isopropylphenylamino)-6-(4-methyl-piperazin-1-yl)-1H-benzimidazole-5-carboxylic acid (1H-indazol-6-yl)-amide |
| 49 | 2-(2-Isopropylphenylamino)-6-morpholin-4-yl-1H-benzimidazole-5-carboxylic acid (1H-indazol-6-yl)-amide |
| 50 | 6-(4-Methylpiperazin-1-yl)-2-(2-trifluoromethyl-phenylamino)-1H-benzimidazole-5-carboxylic acid (1H-indazol-6-yl)-amide |
| 51 | 2-(3,5-Difluorophenylamino)-6-(4-methyl-piperazin-1-yl)-1H-benzimidazole-5-carboxylic acid (1H-indazol-6-yl)-amide |
| 52 | 2-(2,4-Dichlorophenylamino)-6-(4-methyl-piperazin-1-yl)-1H-benzimidazole-5-carboxylic acid (1H-indazol-6-yl)-amide |
| 53 | 6-(4-Methylpiperazin-1-yl)-2-(thiazol-2-ylamino)-1H-benzimidazole-5-carboxylic acid (1H-indazol-6-yl)-amide |
| 54 | 6-Morpholin-4-yl-2-(2-trifluoromethylphenylamino)-1H-benzimidazole-5-carboxylic acid (1H-indazol-6-yl)-amide |
| 55 | 2-(3,5-Difluorophenylamino)-6-morpholin-4-yl-1H-benzimidazole-5-carboxylic acid (1H-indazol-6-yl)-amide |
| 56 | 2-(2,4-Dichlorophenylamino)-6-morpholin-4-yl-1H-benzimidazole-5-carboxylic acid (1H-indazol-6-yl)-amide |
| 57 | 6-Piperidin-1-yl-2-(2-trifluoromethyl-phenylamino)-1H-benzimidazole-5-carboxylic acid (1H-indazol-6-yl)-amide |
| 58 | 6-(4-Methyl-piperazin-1-yl)-2-(3-methyl-pyridin-2-ylamino)-1H-benzimidazole-5-carboxylic acid (1H-indazol-6-yl)-amide |
| 59 | 6-Morpholin-4-yl-2-(thiazol-2-ylamino)-1H-benzimidazole-5-carboxylic acid (1H-indazol-6-yl)-amide |
| 60 | 2-(3-Methylpyridin-2-ylamino)-6-morpholin-4-yl-1H-benzimidazole-5-carboxylic acid (1H-indazol-6-yl)-amide |
| 61 | 2-(1-Isopropyl-1H-imidazol-2-ylamino)-6-(4-methylpiperazin-1-yl)-1H-benzimidazole-5-carboxylic acid (1H-indazol-6-yl)-amide |
| 62 | 2-(1-Cyclopentyl-1H-imidazol-2-ylamino)-6-(4-methylpiperazin-1-yl)-1H-benzimidazole-5-carboxylic acid (1H-indazol-6-yl)-amide |
| 63 | 2-(1-Isopropyl-1H-imidazol-2-ylamino)-6-morpholin-4-yl-1H-benzimidazole-5-carboxylic acid (1H-indazol-6-yl)-amide |
| 64 | 2-(1-Cyclopentyl-1H-imidazol-2-ylamino)-6-morpholin-4-yl-1H-benzimidazole-5-carboxylic acid (1H-indazol-6-yl)-amide |
| 65 | 2-(2-Ethyl-2H-pyrazol-3-ylamino)-6-morpholin-4-yl-1H-benzimidazole-5-carboxylic acid (1H-indazol-6-yl)-amide |
| 66 | 2-(2-Isopropylphenylamino)-3H-benzimidazole-5-carboxylic acid [3-(2-morpholin-4-yl-ethylamino)-1H-indazol-6-yl]-amide |
| 67 | 2-(2-Isopropylphenylamino)-3H-benzimidazole-5-carboxylic acid [3-(3-morpholin-4-yl-propylamino)-1H-indazol-6-yl]-amide |
| 68 | 2-(2-Isopropylphenylamino)-3H-benzimidazole-5-carboxylic acid (3-methylamino-1H-indazol-6-yl)-amide |
| 69 | 2-(Pyridin-2-ylamino)-1H-benzimidazole-5-carboxylic acid (3-amino-1H-indazol-6-yl)-amide |
| 70 | 2-(2-Isopropylphenylamino)-3H-benzimidazole-5-carboxylic acid {3-[(1-methyl-piperidine-4-carbonyl)-amino]-1H-indazol-6-yl}-amide |
| 71 | 2-(Pyridin-2-ylamino)-1H-benzimidazole-5-carboxylic acid (3-acetylamino-1H-indazol-6-yl)-amide |
| 72 | 2-(2,4-Dichlorophenylamino)-3H-benzimidazole-5-carboxylic acid (3-acetylamino-1H-indazol-6-yl)-amide |
| 73 | 2-(2,4-Dichlorophenylamino)-3H-benzimidazole-5-carboxylic acid (3-benzoylamino-1H-indazol-5-yl)-amide |
| 74 | 2-(2-Isopropylphenylamino)-3H-benzimidazole-5-carboxylic acid (3-methoxy-1H-indazol-6-yl)-amide |
| 75 | 2-(2-Isopropylphenylamino)-3H-benzimidazole-5-carboxylic acid [3-(2-morpholin-4-yl-ethoxy)-1H-indazol-6-yl]-amide |
| 76 | 2-(2,4-Dichlorophenylamino)-3H-benzimidazole-5-carboxylic acid (3-morpholin-4-ylmethyl-1H-indazol-6-yl)-amide |

TABLE 1-continued

| Ex. | Name |
|---|---|
| 77 | 2-(2,4-Dichlorophenylamino)-3H-benzimidazole-5-carboxylic acid (3-methyl-1H-indazol-6-yl)-amide |
| 78 | 2-(2-Ethylphenylamino)-3H-benzimidazole-5-carboxylic acid (3-chloro-1H-indazol-6-yl)-amide |
| 79 | 2-[6-(1H-Indazol-6-ylcarbamoyl)-1H-benzimidazol-2-ylamino]-6,7-dihydro-4H-thiazolo[5,4-c]pyridine-5-carboxylic acid tert-butyl ester |
| 80 | 2-(4,5,6,7-Tetrahydro-thiazolo[5,4-c]pyridin-2-ylamino)-3H-benzimidazole-5-carboxylic acid (1H-indazol-6-yl)-amide |
| 81 | 2-(2-Isopropylphenylamino)-3H-benzimidazole-5-carboxylic acid [1-(2-hydroxy-ethyl)-1H-indazol-5-yl]-amide |
| 82 | 2-(2-Cyclohexylphenylamino)-3H-benzimidazole-5-carboxylic acid (1H-indazol-6-yl)-amide |
| 83 | 2-(3-Methylthiophen-2-ylamino)-3H-benzimidazole-5-carboxylic acid (1H-indazol-6-yl)-amide |
| 84 | 1H-Indazole-6-carboxylic acid [2-(2-isopropyl-phenylamino)-3H-benzimidazol-5-yl]-amide |
| 85 | 6-(4-Methylpiperazin-1-yl)-2-(2-trifluoromethyl-phenylamino)-1H-benzimidazole-5-carboxylic acid (1H-indazol-5-yl)-amide |
| 86 | 6-Morpholin-4-yl-2-(2-trifluoromethylphenylamino)-1H-benzimidazole-5-carboxylic acid (1H-indazol-5-yl)-amide |
| 87 | 4-[6-(1H-Indazol-6-ylcarbamoyl)-2-(2-trifluoromethylphenylamino)-3H-benzimidazol-5-yl]-piperazine-1-carboxylic acid tert-butyl ester |
| 88 | 6-Piperazin-1-yl-2-(2-trifluoromethylphenylamino)-1H-benzimidazole-5-carboxylic acid (1H-indazol-6-yl)-amide |
| 89 | 4-[6-(1H-Indazol-6-ylcarbamoyl)-2-(3-methylpyridin-2-ylamino)-3H-benzimidazol-5-yl]-piperazine-1-carboxylic acid tert-butyl ester |
| 90 | 2-(3-Methylpyridin-2-ylamino)-6-piperazin-1-yl-1H-benzimidazole-5-carboxylic acid (1H-indazol-6-yl)-amide |
| 91 | 2-(2,6-diethylphenylamino)-3H-benzimidazole-5-carboxylic acid (1H-indazol-6-yl)-amide |
| 92 | 6-diisobutylamino-2-(2-trifluoromethylphenylamino)-3H-benzimidazole-5-carboxylic acid (1H-indazol-6-yl)-amide |
| 93 | 6-Diethylamino-2-(3-methylpyridin-2-ylamino)-1H-benzimidazole-5-carboxylic acid (1H-indazol-6-yl)-amide |
| 94 | 6-(2,6-Dimethylmorpholin-4-yl)-2-(2-trifluoromethylphenylamino)-1H-benzimidazole-5-carboxylic acid (1H-indazol-6-yl)-amide |
| 95 | 6-Diethylamino-2-(2-trifluoromethyl-phenylamino)-1H-benzimidazole-5-carboxylic acid (1H-indazol-6-yl)-amide |
| 96 | 6-[(2-dimethylaminoethyl)methylamino]-2-(2-trifluoromethylphenylamino)-1H-benzimidazole-5-carboxylic acid (1H-indazol-6-yl)-amide |
| 97 | 6-(4-Dimethylaminopiperidin-1-yl)-2-(2-trifluoromethylphenylamino)-1H-benzimidazole-5-carboxylic acid (1H-indazol-6-yl)-amide |
| 98 | 6-Dipropylamino-2-(2-trifluoromethylphenylamino)-1H-benzimidazole-5-carboxylic acid (1H-indazol-6-yl)-amide |
| 99 | 6-Dipropylamino-2-(3-methylpyridin-2-ylamino)-1H-benzimidazole-5-carboxylic acid (1H-indazol-6-yl)-amide |
| 100 | 6-[Bis-(2-methoxyethyl)amino]-2-(2-trifluoromethylphenylamino)-1H-benzimidazole-5-carboxylic acid (1H-indazol-6-yl)-amide |
| 101 | 6-(4-Hydroxypiperidin-1-yl)-2-(2-trifluoromethylphenylamino)-1H-benzimidazole-5-carboxylic acid (1H-indazol-6-yl)-amide |
| 102 | 6-[Ethyl-(2-methoxyethyl)amino]-2-(2-trifluoromethylphenylamino)-1H-benzimidazole-5-carboxylic acid (1H-indazol-6-yl)-amide |
| 103 | 6-[Bis-(2-methoxyethyl)amino]-2-(3-methylpyridin-2-ylamino)-1H-benzimidazole-5-carboxylic acid (1H-indazol-6-yl)-amide |
| 104 | 2-(3-Methylpyridin-2-ylamino)-6-pyrrolidin-1-yl-1H-benzimidazole-5-carboxylic acid (1H-indazol-6-yl)-amide |
| 105 | 6-Pyrrolidin-1-yl-2-(2-trifluoromethylphenylamino)-1H-benzimidazole-5-carboxylic acid (1H-indazol-6-yl)-amide |
| 106 | 6-[(2-Dimethylaminoethyl)ethylamino]-2-(2-trifluoromethylphenylamino)-1H-benzimidazole-5-carboxylic acid (1H-indazol-6-yl)-amide |
| 107 | 6-(4-Hydroxypiperidin-1-yl)-2-(3-methylpyridin-2-ylamino)-1H-benzimidazole-5-carboxylic acid (1H-indazol-6-yl)-amide |
| 108 | 6-[Ethyl-(2-methoxyethyl)amino]-2-(3-methylpyridin-2-ylamino)-1H-benzimidazole-5-carboxylic acid (1H-indazol-6-yl)-amide |
| 109 | 6-(Ethylpropylamino)-2-(2-trifluoromethylphenylamino)-1H-benzimidazole-5-carboxylic acid (1H-indazol-6-yl)-amide |
| 110 | 6-(Ethylpropylamino)-2-(3-methylpyridin-2-ylamino)-1H-benzimidazole-5-carboxylic acid (1H-indazol-6-yl)-amide |
| 111 | 6-(4-Isopropylpiperazin-1-yl)-2-(2-trifluoromethylphenylamino)-1H-benzimidazole-5-carboxylic acid (1H-indazol-6-yl)-amide |
| 112 | 6-(Ethylmethylamino)-2-(2-trifluoromethyl-phenylamino)-1H-benzimidazole-5-carboxylic acid (1H-indazol-6-yl)-amide |
| 113 | 6-(Ethylmethylamino)-2-(3-methylpyridin-2-ylamino)-1H-benzimidazole-5-carboxylic acid (1H-indazol-6-yl)-amide |

TABLE 1-continued

| Ex. | Name |
|---|---|
| 114 | 6-(4-Isopropylpiperazin-1-yl)-2-(3-methylpyridin-2-ylamino)-1H-benzimidazole-5-carboxylic acid (1H-indazol-6-yl)-amide |
| 115 | 2-(3-Chloro-pyridin-2-ylamino)-6-diethylamino-1H-benzoimidazole-5-carboxylic acid (1H-indazol-6-yl)-amide |
| 116 | 6-Diethylamino-2-(3-trifluoromethyl-pyridin-2-ylamino)-1H-benzoimidazole-5-carboxylic acid (1H-indazol-6-yl)-amide |
| 117 | 2-(1-Cyclopentyl-1H-imidazol-2-ylamino)-6-diethylamino-1H-benzoimidazole-5-carboxylic acid (1H-indazol-6-yl)-amide |
| 118 | 2-Cyclohexylamino-6-diethylamino-1H-benzoimidazole-5-carboxylic acid (1H-indazol-6-yl)-amide |
| 119 | 2-Cyclopentylamino-6-diethylamino-1H-benzoimidazole-5-carboxylic acid (1H-indazol-6-yl)-amide |
| 120 | 2-(Bicyclo[2.2.1]hept-2-ylamino)-6-diethylamino-1H-benzoimidazole-5-carboxylic acid (1H-indazol-6-yl)-amide |
| 121 | 6-Diethylamino-2-isopropylamino-1H-benzoimidazole-5-carboxylic acid (1H-indazol-6-yl)-amide |
| 122 | 6-Diethylamino-2-(3-ethyl-6-methyl-pyridin-2-ylamino)-3H-benzoimidazole-5-carboxylic acid (1H-indazol-6-yl)-amide |
| 123 | 6-Diethylamino-2-(2,5-difluoro-phenylamino)-1H-benzoimidazole-5-carboxylic acid (1H-indazol-6-yl)-amide |
| 124 | 6-Diethylamino-2-(3,5-difluoro-phenylamino)-1H-benzoimidazole-5-carboxylic acid (1H-indazol-6-yl)-amide |
| 125 | 2-(2-Chloro-5-trifluoromethyl-phenylamino)-6-diethylamino-1H-benzoimidazole-5-carboxylic acid (1H-indazol-6-yl)-amide |
| 126 | 6-Diethylamino-2-(2-trifluoromethoxy-phenylamino)-1H-benzoimidazole-5-carboxylic acid (1H-indazol-6-yl)-amide |
| 127 | 3-[6-Diethylamino-5-(1H-indazol-6-ylcarbamoyl)-1H-benzoimidazol-2-ylamino]-benzoic acid methyl ester |
| 128 | 6-Diethylamino-2-(2-isopropyl-phenylamino)-1H-benzoimidazole-5-carboxylic acid (1H-indazol-6-yl)-amide |
| 129 | 2-(4-Chloro-phenylamino)-6-diethylamino-1H-benzoimidazole-5-carboxylic acid (1H-indazol-6-yl)-amide |
| 130 | 2-(2,4-Dichloro-phenylamino)-6-diethylamino-1H-benzoimidazole-5-carboxylic acid (1H-indazol-6-yl)-amide |
| 131 | 6-Diethylamino-2-(2,6-difluoro-phenylamino)-1H-benzoimidazole-5-carboxylic acid (1H-indazol-6-yl)-amide |
| 132 | 6-Diethylamino-2-(2-methoxy-phenylamino)-1H-benzoimidazole-5-carboxylic acid (1H-indazol-6-yl)-amide |
| 133 | 6-Diethylamino-2-(2-trifluoromethyl-phenylamino)-1H-benzoimidazole-5-carboxylic acid benzothiazol-6-ylamide |
| 134 | 2-(Bicyclo[2.2.1]hept-2-ylamino)-6-diethylamino-1H-benzoimidazole-5-carboxylic acid benzothiazol-6-ylamide |
| 135 | 6-Diethylamino-2-isopropylamino-1H-benzoimidazole-5-carboxylic acid benzothiazol-6-ylamide |
| 136 | 6-Diethylamino-2-(2,5-difluoro-phenylamino)-3H-benzoimidazole-5-carboxylic acid benzothiazol-6-ylamide |
| 137 | 6-Diethylamino-2-(3,5-difluoro-phenylamino)-3H-benzoimidazole-5-carboxylic acid benzothiazol-6-ylamide |
| 138 | 2-(2,4-Dichloro-phenylamino)-6-diethylamino-3H-benzoimidazole-5-carboxylic acid benzothiazol-6-ylamide |
| 139 | 6-Diethylamino-2-(2-trifluoromethoxy-phenylamino)-3H-benzoimidazole-5-carboxylic acid benzothiazol-6-ylamide |
| 140 | 6-Diethylamino-2-(2-isopropyl-phenylamino)-3H-benzoimidazole-5-carboxylic acid benzothiazol-6-ylamide |
| 141 | 6-(4-Methyl-piperazin-1-yl)-2-(2-trifluoromethyl-phenylamino)-1H-benzoimidazole-5-carboxylic acid benzothiazol-6-ylamide |
| 142 | 6-(4-Methyl-piperazin-1-yl)-2-(3-methyl-pyridin-2-ylamino)-1H-benzoimidazole-5-carboxylic acid benzothiazol-6-ylamide |
| 143 | 6-Morpholin-4-yl-2-(2-trifluoromethyl-phenylamino)-1H-benzoimidazole-5-carboxylic acid benzothiazol-6-ylamide |
| 144 | 2-(3-Methyl-pyridin-2-ylamino)-6-morpholin-4-yl-1H-benzoimidazole-5-carboxylic acid benzothiazol-6-ylamide |
| 145 | 6-(3,5-Dimethyl-piperazin-1-yl)-2-(2-trifluoromethyl-phenylamino)-1H-benzoimidazole-5-carboxylic acid (1H-indazol-6-yl)-amide |
| 146 | 6-(2-Methoxyethylamino)-2-(2-trifluoromethylphenylamino)-1H-benzoimidazole-5-carboxylic acid (1H-indazol-6-yl)-amide |
| 147 | 6-(2-Methoxy-ethylamino)-2-(3-methyl-pyridin-2-ylamino)-1H-benzoimidazole-5-carboxylic acid (1H-indazol-6-yl)-amide |
| 148 | 6-(4-Methyl-piperazin-1-yl)-2-(2-trifluoromethyl-benzylamino)-1H-benzoimidazole-5-carboxylic acid (1H-indazol-6-yl)-amide |
| 149 | 2-Benzylamino-6-(4-methyl-piperazin-1-yl)-1H-benzoimidazole-5-carboxylic acid (1H-indazol-6-yl)-amide |
| 150 | 2-(Cyclohexylmethyl-amino)-6-(4-methyl-piperazin-1-yl)-1H-benzoimidazole-5-carboxylic acid (1H-indazol-6-yl)-amide |
| 151 | 2-Cyclopentylamino-6-(4-methyl-piperazin-1-yl)-1H-benzoimidazole-5-carboxylic acid (1H-indazol-6-yl)-amide |

TABLE 1-continued

| Ex. | Name |
|---|---|
| 152 | 2-((1S,2S,4R)-Bicyclo[2.2.1]hept-2-ylamino)-6-(4-methyl-piperazin-1-yl)-1H-benzoimidazole-5-carboxylic acid (1H-indazol-6-yl)-amide |
| 153 | 2-(Adamantan-1-ylamino)-6-(4-methyl-piperazin-1-yl)-1H-benzoimidazole-5-carboxylic acid (1H-indazol-6-yl)-amide |
| 154 | 6-Propylamino-2-(2-trifluoromethyl-phenylamino)-1H-benzoimidazole-5-carboxylic acid (1H-indazol-6-yl)-amide |
| 155 | {1-[6-(1H-Indazol-6-ylcarbamoyl)-2-(2-trifluoromethyl-phenylamino)-3H-benzoimidazol-5-yl]-piperidin-4-yl}-carbamic acid tert-butyl ester |
| 156 | 6-(4-Amino-piperidin-1-yl)-2-(2-trifluoromethyl-phenylamino)-1H-benzoimidazole-5-carboxylic acid (1H-indazol-6-yl)-amide trihydrochloride |
| 157 | {1-[6-(1H-Indazol-6-ylcarbamoyl)-2-(3-methyl-pyridin-2-ylamino)-3H-benzoimidazol-5-yl]-piperidin-4-yl}-carbamic acid tert-butyl ester |
| 158 | 6-(4-Amino-piperidin-1-yl)-2-(3-methyl-pyridin-2-ylamino)-1H-benzoimidazole-5-carboxylic acid (1H-indazol-6-yl)-amide trihydrochloride |
| 159 | [5-(1H-Indazol-6-ylethynyl)-1H-benzoimidazol-2-yl]-(2-trifluoromethyl-phenyl)-amine |
| 160 | 6-Dimethylamino-2-(2-trifluoromethyl-phenylamino)-1H-benzoimidazole-5-carboxylic acid (1H-indazol-6-yl)-amide |
| 161 | 6-Dimethylamino-2-(3-methyl-pyridin-2-ylamino)-1H-benzoimidazole-5-carboxylic acid (1H-indazol-6-yl)-amide |
| 162 | 6-(4-Methyl-piperazin-1-yl)-2-(2-trifluoromethyl-phenylamino)-1H-benzoimidazole-5-carboxylic acid benzothiazol-5-ylamide |
| 163 | 4-[6-(Benzothiazol-6-ylcarbamoyl)-2-(2-trifluoromethyl-phenylamino)-3H-benzoimidazol-5-yl]-piperazine-1-carboxylic acid tert-butyl ester |
| 164 | 6-Piperazin-1-yl-2-(2-trifluoromethyl-phenylamino)-1H-benzoimidazole-5-carboxylic acid benzothiazol-6-ylamide trihydrochloride |
| 165 | 4-[6-(Benzothiazol-6-ylcarbamoyl)-2-(3-methyl-pyridin-2-ylamino)-3H-benzoimidazol-5-yl]-piperazine-1-carboxylic acid tert-butyl ester |
| 166 | 2-(3-Methyl-pyridin-2-ylamino)-6-piperazin-1-yl-1H-benzoimidazole-5-carboxylic acid benzothiazol-6-ylamide trihydrochloride |
| 167 | 2-(2-Trifluoromethyl-phenylamino)-1H-benzoimidazole-5-carboxylic acid benzothiazol-6-ylamide |
| 168 | 6-Piperazin-1-yl-2-(2-trifluoromethyl-phenylamino)-1H-benzoimidazole-5-carboxylic acid (5-methyl-1H-indazol-6-yl)-amide |
| 169 | 4-[2-((1S,2S,4R)Bicyclo[2.2.1]hept-2-ylamino)-6-(1H-indazol-6-ylcarbamoyl)-3H-benzoimidazol-5-yl]-piperazine-1-carboxylic acid tert-butyl ester |
| 170 | 2-((1S,2S,4R)-Bicyclo[2.2.1]hept-2-ylamino)-6-piperazin-1-yl-1H-benzoimidazole-5-carboxylic acid (1H-indazol-6-yl)-amide trihydrochloride |
| 171 | 6-Chloro-2-(2-trifluoromethyl-phenylamino)-1H-benzoimidazole-5-carboxylic acid (1H-indazol-6-yl)-amide |
| 172 | 2-((1S,2S,4R)-Bicyclo[2.2.1]hept-2-ylamino)-6-chloro-1H-benzoimidazole-5-carboxylic acid (1H-indazol-6-yl)-amide |
| 173 | 6-[4-(2-Hydroxy-ethyl)-piperazin-1-yl]-2-(2-trifluoromethyl-phenylamino)-1H-benzoimidazole-5-carboxylic acid (1H-indazol-6-yl)-amide |
| 174 | {4-[6-(1H-Indazol-6-ylcarbamoyl)-2-(2-trifluoromethyl-phenylamino)-3H-benzoimidazol-5-yl]-piperazin-1-yl}-acetic acid |
| 175 | 6-(4-Dimethylsulfamoyl-piperazin-1-yl)-2-(2-trifluoromethyl-phenylamino)-1H-benzoimidazole-5-carboxylic acid (1H-indazol-6-yl)-amide |
| 176 | {6-[5-(1H-Indazol-6-yl)-1H-imidazol-2-yl]-1H-benzoimidazol-2-yl}-(2-trifluoromethyl-phenyl)-amine |
| 177 | 6-(2-Dimethylamino-ethylsulfanyl)-2-(2-trifluoromethyl-phenylamino)-1H-benzoimidazole-5-carboxylic acid (1H-indazol-6-yl)-amide |
| 178 | 5-Ethyl-8-(1H-indazol-6-yl)-2-(2-trifluoromethyl-phenylamino)-5,6,7,8-tetrahydro-3H-1,3,5,8-tetraaza-cyclohepta[f]inden-9-one |
| 179 | 6-Imidazol-1-yl-2-(2-trifluoromethyl-phenylamino)-3H-benzoimidazole-5-carboxylic acid (1H-indazol-6-yl)-amide |
| 180 | 2-(2-Trifluoromethyl-phenylamino)-benzooxazole-5-carboxylic acid (1H-indazol-6-yl)-amide |
| 181 | 2-(1-Benzyl-1H-imidazol-2-ylamino)-6-(4-methyl-piperazin-1-yl)-1H-benzoimidazole-5-carboxylic acid (1H-indazol-6-yl)-amide |
| 182 | 4-[2-(1-Cyclopentyl-1H-imidazol-2-ylamino)-6-(1H-indazol-6-ylcarbamoyl)-3H-benzoimidazol-5-yl]-piperazine-1-carboxylic acid tert-butyl ester |
| 183 | 2-(1-Cyclopentyl-1H-imidazol-2-ylamino)-6-piperazin-1-yl-1H-benzoimidazole-5-carboxylic acid (1H-indazol-6-yl)-amide trihydrochloride |
| 184 | 2-(1-Cyclopentyl-1H-imidazol-2-ylamino)-6-(4-isopropyl-piperazin-1-yl)-1H-benzoimidazole-5-carboxylic acid (1H-indazol-6-yl)-amide |

TABLE 1-continued

| Ex. | Name |
|---|---|
| 185 | 2-(1-Cyclopentyl-1H-imidazol-2-ylamino)-6-(4-ethyl-piperazin-1-yl)-1H-benzoimidazole-5-carboxylic acid (1H-indazol-6-yl)-amide |
| 186 | 2-(1-Cyclopentyl-1H-imidazol-2-ylamino)-6-[(2-dimethylaminoethyl)-methyl-amino]-1H-benzoimidazole-5-carboxylic acid (1H-indazol-6-yl)-amide |
| 187 | 2-(1-Cyclopentyl-1H-imidazol-2-ylamino)-6-(4-methyl-[1,4]diazepan-1-yl)-1H-benzoimidazole-5-carboxylic acid (1H-indazol-6-yl)-amide |
| 188 | 2-(1-Cyclohexyl-1H-imidazol-2-ylamino)-6-(4-methyl-piperazin-1-yl)-1H-benzoimidazole-5-carboxylic acid (1H-indazol-6-yl)-amide |
| 189 | 2-(1-Methyl-1H-imidazol-2-ylamino)-6-(4-methyl-piperazin-1-yl)-1H-benzoimidazole-5-carboxylic acid (1H-indazol-6-yl)-amide |
| 190 | 2-(1-Cyclohexylmethyl-1H-imidazol-2-ylamino)-6-(4-methyl-piperazin-1-yl)-1H-benzoimidazole-5-carboxylic acid (1H-indazol-6-yl)-amide |
| 191 | 2-(1-Isobutyl-1H-imidazol-2-ylamino)-6-(4-methyl-piperazin-1-yl)-1H-benzoimidazole-5-carboxylic acid (1H-indazol-6-yl)-amide |
| 192 | 2-(1-Cyclobutyl-1H-imidazol-2-ylamino)-6-(4-methyl-piperazin-1-yl)-1H-benzoimidazole-5-carboxylic acid (1H-indazol-6-yl)-amide |
| 193 | 2-[1-(1-Ethyl-propyl)-1H-imidazol-2-ylamino]-6-(4-methyl-piperazin-1-yl)-1H-benzoimidazole-5-carboxylic acid (1H-indazol-6-yl)-amide |
| 194 | 2-(1-Butyl-1H-imidazol-2-ylamino)-6-(4-methyl-piperazin-1-yl)-1H-benzoimidazole-5-carboxylic acid (1H-indazol-6-yl)-amide |
| 195 | 2-[1-(2-Methoxy-ethyl)-1H-imidazol-2-ylamino]-6-(4-methyl-piperazin-1-yl)-1H-benzoimidazole-5-carboxylic acid (1H-indazol-6-yl)-amide |
| 196 | 2-(1-Ethyl-1H-imidazol-2-ylamino)-6-(4-methyl-piperazin-1-yl)-1H-benzoimidazole-5-carboxylic acid (1H-indazol-6-yl)-amide |
| 197 | 2-[1-(2-Methoxy-ethyl)-1H-imidazol-2-ylamino]-6-(4-methyl-piperazin-1-yl)-1H-benzoimidazole-5-carboxylic acid benzothiazol-6-ylamide |
| 198 | 2-(1-Ethyl-1H-imidazol-2-ylamino)-6-(4-methyl-piperazin-1-yl)-1H-benzoimidazole-5-carboxylic acid benzothiazol-6-ylamide |
| 199 | 2-(1-Cyclopentyl-1H-imidazol-2-ylamino)-6-(4-methyl-piperazin-1-yl)-1H-benzoimidazole-5-carboxylic acid (1H-indazol-5-yl)-amide |
| 200 | 2-(1-Cyclopentyl-1H-imidazol-2-ylamino)-6-(4-methyl-piperazin-1-yl)-1H-benzoimidazole-5-carboxylic acid (1H-benzotriazol-5-yl)-amide |
| 201 | 2-(1-Cyclopentyl-1H-imidazol-2-ylamino)-6-(4-methyl-piperazin-1-yl)-1H-benzoimidazole-5-carboxylic acid benzothiazol-6-ylamide |
| 202 | 2-(1-Cyclopentyl-1H-imidazol-2-ylamino)-6-(4-methyl-piperazin-1-yl)-1H-benzoimidazole-5-carboxylic acid (2-oxo-2,3-dihydro-1H-indol-5-yl)-amide |
| 203 | 2-(1-Cyclopentyl-1H-imidazol-2-ylamino)-6-(4-methyl-piperazin-1-yl)-1H-benzoimidazole-5-carboxylic acid (1H-indol-6-yl)-amide |
| 204 | 2-(1-Cyclopentyl-1H-imidazol-2-ylamino)-6-(4-methyl-piperazin-1-yl)-1H-benzoimidazole-5-carboxylic acid (3H-benzoimidazol-5-yl)-amide |
| 205 | 2-(1-Cyclopentyl-1H-imidazol-2-ylamino)-6-(4-methyl-piperazin-1-yl)-1H-benzoimidazole-5-carboxylic acid benzothiazol-5-ylamide |
| 206 | 6-(4-Methyl-piperazin-1-yl)-2-(1-thietan-3-yl-1H-imidazol-2-ylamino)-1H-benzoimidazole-5-carboxylic acid (1H-indazol-6-yl)-amide |
| 207 | 2-Amino-6-(4-methylpiperazin-1-yl)-1H-benzimidazole-5-carboxylic acid (1H-indazol-6-yl)-amide trihydrobromide |
| 208 | 2-(3-cyclopentyl-3-ethylureido)-6-(4-methyl-piperazin-1-yl)-1H-benzimidazole-5-carboxylic acid (1H-indazol-6-yl)-amide |
| 209 | 2-Mercapto-6-(4-methylpiperazin-1-yl)-1H-benzimidazole-5-carboxylic acid (1H-indazol-6-yl)-amide |
| 210 | 2-(1-Cyclopentyl-1H-benzimidazol-2-ylamino)-6-(4-methyl-piperazin-1-yl)-1H-benzoimidazole-5-carboxylic acid (1H-indazol-6-yl)-amide |
| 211 | [6-(1H-Indazol-6-yloxy)-1H-benzimidazol-2-yl]-(2-trifluoromethyl-phenyl)-amine |
| 212 | {5-[2-(1H-indazol-6-yl)-ethyl]-1H-benzimidazol-2-yl}-(2-trifluoromethylphenyl)amine |
| 213 | 3-[6-Diethylamino-5-(1H-indazol-6-ylcarbamoyl)-1H-benzimidazol-2-ylamino]-benzoic acid |
| 214 | 3-[5-(Benzothiazol-6-ylcarbamoyl)-6-diethylamino-1H-benzoimidazol-2-ylamino]-benzoic acid methyl ester |
| 215 | 3-[5-(Benzothiazol-6-ylcarbamoyl)-6-diethylamino-1H-benzoimidazol-2-ylamino]-benzoic acid |

In another aspect, the present invention comprises a pharmaceutical composition comprising the compound of Formula (I) and a pharmaceutically acceptable carrier, excipient, diluent, or a mixture thereof. The present invention further provides uses of the compound of Formula (I) for inhibiting Aurora kinase activity and for treating Aurora kinase-mediated disorders.

As used herein, the term "lower" refers to a group having between one and six carbons.

As used herein, the term "alkyl" refers to a straight or branched chain hydrocarbon having from one to ten carbon atoms, optionally substituted and multiple degrees of substitution being allowed. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted and multiple degrees of substitution being allowed. Examples of "alkylene" as used herein include, but are not limited to, methylene, ethylene, and the like.

As used herein, the term "alkyline" refers to a straight or branched chain trivalent hydrocarbon radical having from one to ten carbon atoms, optionally substituted and multiple degrees of substitution being allowed. Examples of "alkyline" as used herein include, but are not limited to, methine, ethyline, and the like.

As used herein, the term "alkenyl" refers to a hydrocarbon radical having from two to ten carbons and at least one carbon-carbon double bond, optionally substituted and multiple degrees of substitution being allowed. Examples of "alkenyl" as used herein include, but are not limited to, 3,3-dimethyl-but-1-phenyl, 4-hex-1-phenyl, and the like.

As used herein, the term "alkenylene" refers to a straight or branched chain divalent hydrocarbon radical having from two to ten carbon atoms and one or more carbon-carbon double bonds, optionally substituted and multiple degrees of substitution being allowed. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted and multiple degrees of substitution being allowed. Examples of "alkynyl" as used herein include, but are not limited to, 4-hex-1 ynyl, 3,3-dimethyl-but-1ynyl, and the like.

As used herein, the term "alkynylene" refers to a straight or branched chain divalent hydrocarbon radical having from two to ten carbon atoms and one or more carbon-carbon triple bonds, optionally substituted and multiple degrees of substitution being allowed. Examples of "alkynylene" as used herein include, but are not limited to, ethyne-1,2-diyl, propyne-1,3-diyl, and the like.

As used herein, the terms "haloaliphatic", "haloalkyl", "haloalkenyl" and "haloalkoxy" refer to an aliphatic, alkyl, alkenyl or alkoxy group, as the case may be, substituted with one or more halogen atoms.

As used herein, "cycloalkyl" refers to a non-aromatic alicyclic hydrocarbon group and optionally possessing one or more degrees of unsaturation, having from three to twelve carbon atoms, optionally substituted and multiple degrees of substitution being allowed. Examples of "cycloalkyl" as used herein include, but are not limited to, cyclopropyl, cyclobutyl, cyclopentyl, cyclohexyl, cycloheptyl, cyclooctyl, and the like.

As used herein, the term "cycloalkylene" refers to an non-aromatic alicyclic divalent hydrocarbon radical having from three to twelve carbon atoms and optionally possessing one or more degrees of unsaturation, optionally substituted with substituents and multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, cyclooctyl-1,5-diyl, and the like.

As used herein, the term "heterocyclic" or the term "heterocyclyl" refers to a non-aromatic three to twelve-membered heterocyclic ring optionally possessing one or more degrees of unsaturation, containing one or more heteroatomic substitutions selected from S, SO, $SO_2$, O, or N, optionally substituted and multiple degrees of substitution being allowed. Such a ring may be optionally fused to from one to three of another "heterocyclic" ring(s) or cycloalkyl ring(s). Examples of "heterocyclyl" include, but are not limited to, tetrahydrofuran, 1,4-dioxane, 1,3-dioxane, piperidine, pyrrolidine, morpholine, piperazine, and the like.

As used herein, the term "heterocyclylene" refers to a non-aromatic three to twelve-membered heterocyclic ring diradical optionally having one or more degrees of unsaturation containing one or more heteroatoms selected from S, SO, $SO_2$, O, or N, optionally substituted and multiple degrees of substitution being allowed. Such a ring may be optionally fused to from one to three benzene rings or to one to three of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to benzene ring fused to one to three benzene rings, optionally substituted and multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one to three optionally substituted benzene rings, optionally substituted and multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic (up to three rings) aromatic ring, containing one or more nitrogen, oxygen, or sulfur heteroatoms, where N-oxides and sulfur monoxides and sulfur dioxides are permissible heteroaromatic substitutions, optionally substituted and multiple degrees of substitution being allowed. For polycyclic heteroaryl aromatic ring systems, one or more of the rings may contain one or more heteroatoms. Examples of "heteroaryl" used herein include, but are not limited to, furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic (up to three rings) heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted and multiple degrees of substitution being allowed. For polycyclic aromatic ring system diradicals, one or more of the rings may contain one or more heteroatoms. Examples of "heteroarylene" used herein include, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to one or two cycloalkyl groups fused to an aryl group, the aryl and cycloalkyl groups having two atoms in common, and wherein the aryl group is the point of substitution. Examples of "fused cycloalkylaryl" used herein include 5-indanyl, 5,6,7,8-tetrahydro-2-naphthyl,

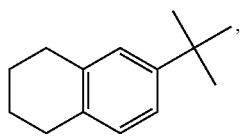

and the like.

As used herein, the term "fused cycloalkylarylene" refers to a fused cycloalkylaryl, wherein the aryl group is divalent. Examples include

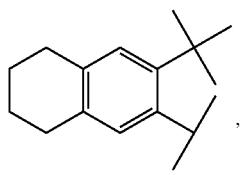

and the like.

As used herein, the term "fused arylcycloalkyl" refers to one or two aryl groups fused to a cycloalkyl group, the cycloalkyl and aryl groups having two atoms in common, and wherein the cycloalkyl group is the point of substitution. Examples of "fused arylcycloalkyl" used herein include 1-indanyl, 2-indanyl, 9-fluorenyl, 1-(1,2,3,4-tetrahydronaphthyl),

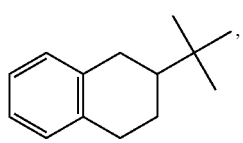

and the like.

As used herein, the term "fused arylcycloalkylene" refers to a fused arylcycloalkyl, wherein the cycloalkyl group is divalent. Examples include 9,1-fluorenylene,

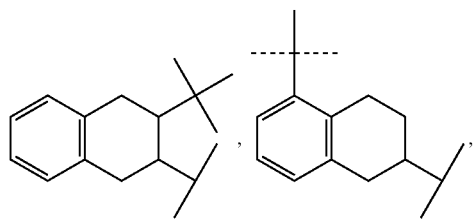

and the like.

As used herein, the term "fused heterocyclylaryl" refers to one or two heterocyclyl groups fused to an aryl group, the aryl and heterocyclyl groups having two atoms in common, and wherein the aryl group is the point of substitution. Examples of "fused heterocyclylaryl" used herein include 3,4-methylenedioxy-1-phenyl,

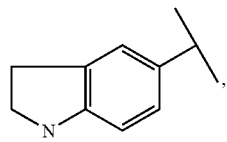

and the like.

As used herein, the term "fused heterocyclylarylene" refers to a fused heterocyclylaryl, wherein the aryl group is divalent. Examples include

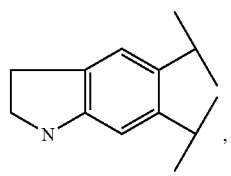

and the like.

As used herein, the term "fused arylheterocyclyl" refers to one or two aryl groups fused to a heterocyclyl group, the heterocyclyl and aryl groups having two atoms in common, and wherein the heterocyclyl group is the point of substitution. Examples of "fused arylheterocyclyl" used herein include 2-(1,3-benzodioxolyl),

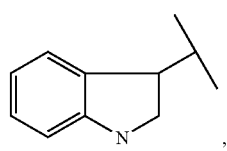

and the like.

As used herein, the term "fused arylheterocyclylene" refers to a fused arylheterocyclyl, wherein the heterocyclyl group is divalent. Examples include

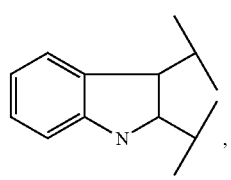

and the like.

As used herein, the term "fused cycloalkylheteroaryl" refers to one or two cycloalkyl groups fused to a heteroaryl group, the heteroaryl and cycloalkyl groups having two atoms in common, and wherein the heteroaryl group is the point of substitution. Examples of "fused cycloalkylheteroaryl" used herein include 5-aza-6-indanyl,

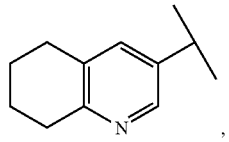

and the like.

As used herein, the term "fused cycloalkylheteroarylene" refers to a fused cycloalkylheteroaryl, wherein the heteroaryl group is divalent. Examples include

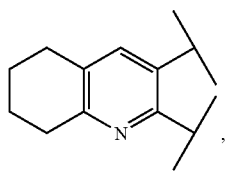

and the like.

As used herein, the term "fused heteroarylcycloalkyl" refers to one or two heteroaryl groups fused to a cycloalkyl group, the cycloalkyl and heteroaryl groups having two atoms in common, and wherein the cycloalkyl group is the point of substitution. Examples of "fused heteroarylcycloalkyl" used herein include 5-aza-1-indanyl,

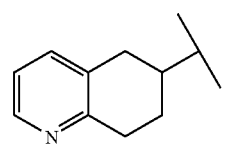

and the like.

As used herein, the term "fused heteroarylcycloalkylene" refers to a fused heteroarylcycloalkyl, wherein the cycloalkyl group is divalent. Examples include

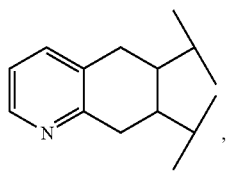

and the like.

As used herein, the term "fused heterocyclylheteroaryl" refers to one or two heterocyclyl groups fused to a heteroaryl group, the heteroaryl and heterocyclyl groups having two atoms in common, and wherein the heteroaryl group is the point of substitution. Examples of "fused heterocyclylheteroaryl" used herein include 1,2,3,4-tetrahydro-beta-carbolin-8-yl,

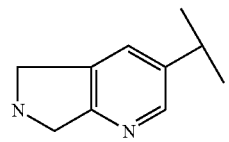

and the like.

As used herein, the term "fused heterocyclylheteroarylene" refers to a fused heterocyclylheteroaryl, wherein the heteroaryl group is divalent. Examples include

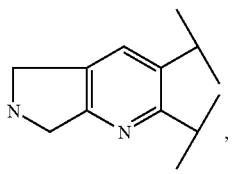

and the like.

As used herein, the term "fused heteroarylheterocyclyl" refers to one or two heteroaryl groups fused to a heterocyclyl group, the heterocyclyl and heteroaryl groups having two atoms in common, and wherein the heterocyclyl group is the point of substitution. Examples of "fused heteroarylheterocyclyl" used herein include -5-aza-2,3-dihydrobenzofuran-2-yl,

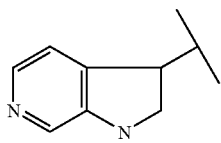

and the like.

As used herein, the term "fused heteroarylheterocyclylene" refers to a fused heteroarylheterocyclyl, wherein the heterocyclyl group is divalent. Examples include

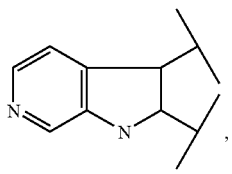

and the like.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO—$, where $R_a$ is alkyl.

As used herein, the term "alkenyloxy" refers to the group $R_aO—$, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfinyl" refers to the group $R_aS(O)$—, where $R_a$ is alkyl.

As used herein, the term "alkenylsulfinyl" refers to the group $R_aS(O)$—, where $R_a$ is alkenyl.

As used herein, the tern "alkynylsulfinyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution of one or more hydrogens of the designated moiety with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" refers iodine, bromine, chlorine or fluorine.

As used herein, the term "mercapto" refers to the substituent —SH.

As used herein, the term "carboxy" refers to the substituent —COOH.

As used herein, the term "cyano" refers to the substituent —CN.

As used herein, the term "aminosulfonyl" refers to the substituent —$SO_2NH_2$.

As used herein, the term "carbamoyl" refers to the substituent —$C(O)NH_2$.

As used herein, the term "sulfanyl" refers to the substituent —S—.

As used herein, the term "sulfinyl" refers to the substituent —S(O)—.

As used herein, the term "sulfonyl" refers to the substituent —$S(O)_2$—.

The compounds can be prepared according to the following reaction Schemes (in which variables are as defined before or are defined) using readily available starting materials, and reagents. In these reactions, it is also possible to make use of variants which are themselves known to those of ordinary skill in this art, but are not mentioned in greater detail.

The present invention also provides a method for the synthesis of compounds useful as intermediates in the preparation of compounds of Formula (I) along with methods for the preparation of compounds of Formula (I). Unless otherwise specified, structural variables are as defined for Formula (I).

As shown in Scheme I, diaminobenzoate (1) is reacted with isothiocyanate (6) by heating in a solvent such as, but not limited to, THF to provide thiourea (2). Isothiocyanate (6) is either commercially available or is prepared from a corresponding amine (5) by reacting with 1,1'-thiocarbonylimidazole in solvent such as, but not limited to, THF. The thiourea (2) is treated with a coupling reagent such as, but not limited to, EDC to furnish aminobenzimidazole, which upon hydrolysis, yields carboxylic acid (3). The carboxylic acid (3) is then coupled with an amine in the presence of a coupling reagent such as, but not limited to, HBTU to form amide (4).

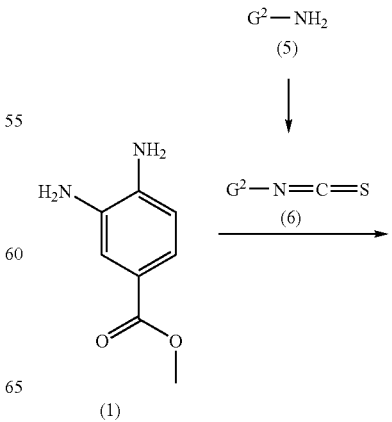

Scheme I

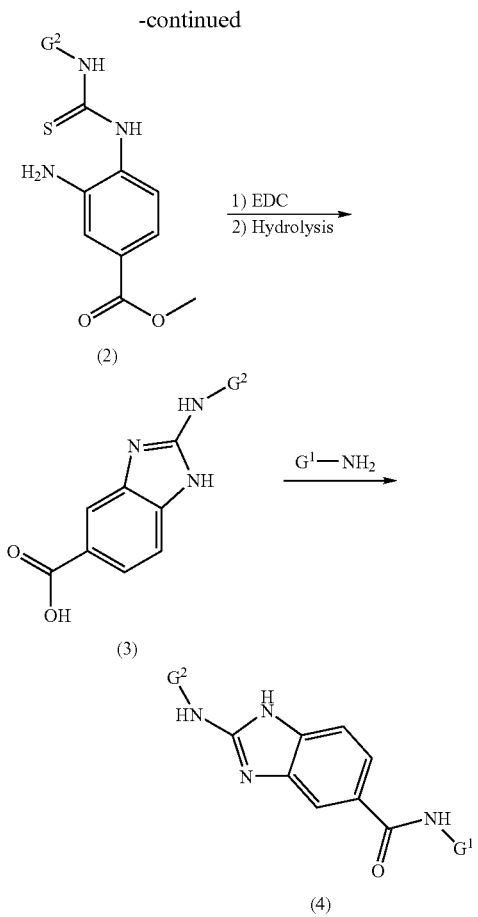

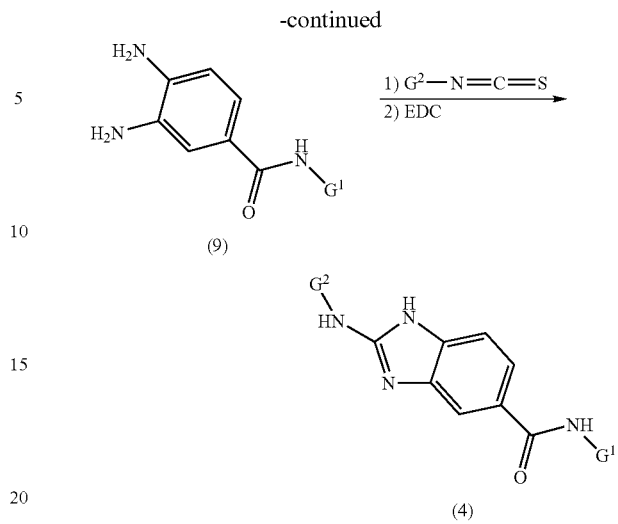

As shown in Scheme III, benzoic acid chloride derivative (10), which is obtained from the corresponding carboxylic acid by heating with a reagent such as, but not limited to, oxalyl chloride, is coupled with an amine in the presence of a base such as, but not limited to, pyridine to form an amide (11). Amide (11) is then converted into nitroaniline (12) by heating with ammonium hydroxide in a solvent such as, but not limited to, DCM. Nitroaniline (12), upon heating with a nucleophile such as, but not limited to, an amine under neat conditions or in the presence of a solvent, is transformed into intermediate (13). The nitro group of intermediate (13) is then reduced under conditions such as, but not limited to, Pd/C under hydrogen atmosphere to provide diamine (14). The diamine (14) is then reacted with an isothiocyanate, as described for Scheme I, to provide thiourea, which upon treatment with coupling reagent such as, but not limited to, EDC to yield aminobenzimidazole (15).

Alternatively, the aminobenzimidazole (4) is also made as shown in Scheme II. Carboxylic acid (7) is coupled with an amine in the presence of a coupling reagent such as, but not limited to HBTU, to form an amide (8). The nitro group of intermediate (8) is then reduced under conditions such as, but not limited to, Pd/C under hydrogen atmosphere to provide diamine (9). The diamine (9) is then reacted with an isothiocyanate, as described for Scheme I, to provide thiourea, which upon treatment with coupling reagent such as, but not limited to, EDC to yield aminobenzimidazole (4).

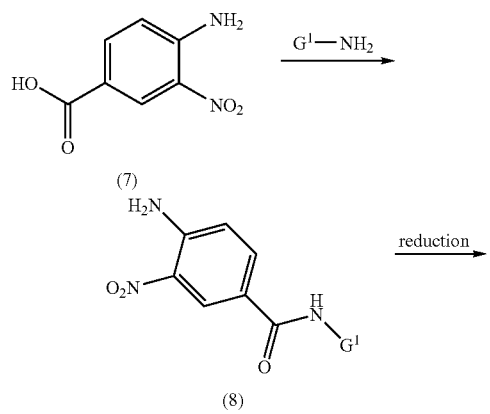

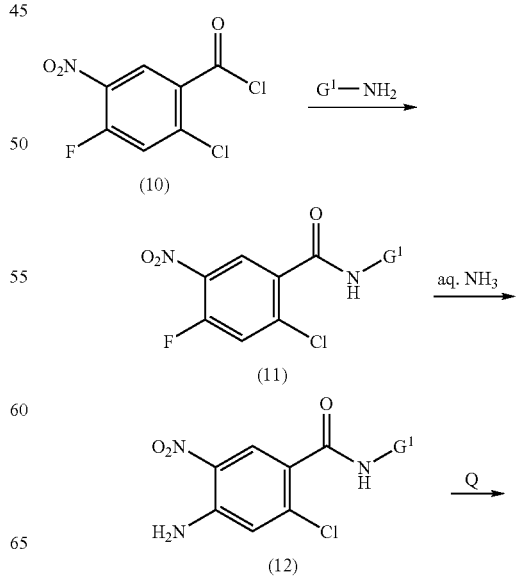

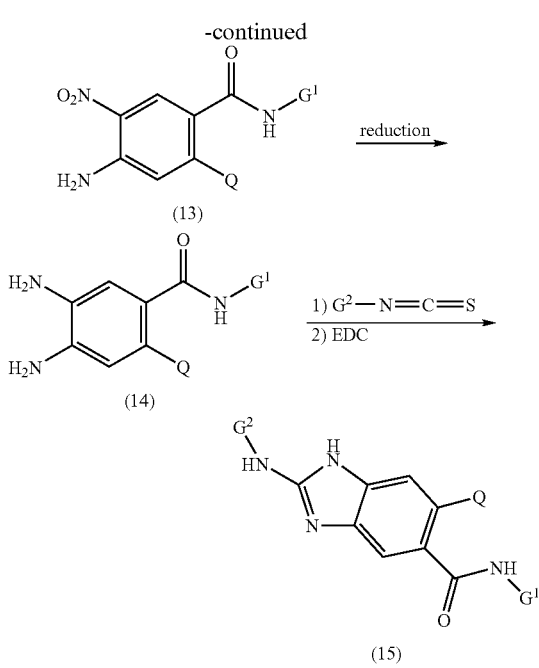

The compounds of this invention are inhibitors of Aurora kinase. The compounds can be assayed in vitro for their ability to inhibit an Aurora kinase. In vitro assays include assays to determine inhibition of the ability of an Aurora kinase to phosphorylate a substrate protein or peptide. Alternate in vitro assays quantitate the ability of the compound to bind to an Aurora kinase. Inhibitor binding may be measured by radiolabelling the inhibitor prior to binding, isolating the inhibitor/Aurora kinase complex and determining the amount of radiolabel bound. Alternatively, inhibitor binding may be determined by running a competition experiment in which new inhibitors are incubated with Aurora kinase bound to a known radioligand. The compounds also can be assayed for their ability to affect cellular or physiological functions mediated by Aurora kinase activity. Assays for each of these activities are described in the Examples and/or are known in the art.

In general, embodiments of the present invention useful for pharmaceutical applications may have inhibitory potencies ($IC_{50}$'s) for a protein of interest of below about 10 µM. In an embodiment, embodiments of the present invention useful for pharmaceutical applications may have an $IC_{50}$ for a protein of interest of below about 1 µM. For particular applications, lower inhibitory potencies may be useful. Thus, in another embodiment, compounds of the present invention may inhibit Aurora kinase with an $IC_{50}$ in a range of less than 100 nM. In another embodiment, compounds of the present invention may inhibit Aurora kinase with inhibitory potencies ($IC_{50}$'s) of between 0.1 nM and 100 nM.

In another embodiment, the present invention provides a pharmaceutical composition comprising a compound of Formula (I) wherein the compound of Formula (I) is administered in a dose of less than 1,000 mg/kg of body weight per day. In another embodiment, the present invention provides a pharmaceutical composition comprising a compound of Formula (I) wherein the compound of Formula (I) is administered in a dose of less than 100 mg/kg of body weight per day. In another embodiment, the present invention provides a pharmaceutical composition comprising a compound of Formula (I) wherein the compound of Formula (I) is administered in a dose of less than 10 mg/kg of body weight per day.

Embodiments of the compounds of the present invention demonstrate utility as inhibitors of Aurora kinase activity or as inhibitors of cell proliferation. Embodiments of the invention described herein are additionally directed to pharmaceutical compositions and methods of inhibiting Aurora kinase in a subject, which methods comprise administering to a subject in need of inhibition of Aurora kinase activity a therapeutically effective amount of a compound of Formula (I), defined above, as a single or polymorphic crystalline form or forms, an amorphous form, a single enantiomer, a racemic mixture, a single stereoisomer, a mixture of stereoisomers, a single diastereoisomer, a mixture of diastereoisomers, a solvate, a pharmaceutically acceptable salt, a solvate, a prodrug, a biohydrolyzable ester, or a biohydrolyzable amide thereof.

In an embodiment, the invention provides a method for inhibiting Aurora kinase activity comprising contacting a cell in which inhibition of Aurora kinase is desired with an Aurora kinase inhibitor of Formula (I). In an embodiment, the Aurora kinase inhibitor interacts with and reduces the activity of fewer than all Aurora kinase enzymes in the cell. Where a compound of the present invention selectively acts as an inhibitor of Aurora kinase in preference to one or more other kinases, treatment of a subject with such a selective compound may possess advantage in the treatment of cancer in the subject over non-specific kinase inhibitors. Thus, in another embodiment, the present invention provides a method for selectively inhibiting Aurora kinase activity in the presence of one or more other kinases comprising contacting a cell in which inhibition of Aurora kinase is desired with an Aurora kinase inhibitor of Formula (I).

The method according to this aspect of the invention causes an inhibition of cell proliferation of the contacted cells. The phrase "inhibiting cell proliferation" is used to denote an ability of an inhibitor of Aurora kinase to inhibit cell number or cell growth in contacted cells as compared to cells not contacted with the inhibitor. An assessment of cell proliferation can be made by counting cells using a cell counter, by measuring uptake of a labeled nucleotide or nucleotide analog, or by an assay of cell viability. Where the cells are in a solid growth (e.g., a solid tumor or organ), such an assessment of cell proliferation can be made by measuring the growth, e.g., with calipers, and comparing the size of the growth of contacted cells with non-contacted cells.

The growth of cells contacted with an inhibitor may be retarded by at least about 50% as compared to growth of non-contacted cells. In various embodiments, cell proliferation of contacted cells is inhibited by at least about 75% as compared to non-contacted cells. In some embodiments, the phrase "inhibiting cell proliferation" includes a reduction in the number of contacted cells, as compared to non-contacted cells. Thus, an inhibitor of Aurora kinase that inhibits cell proliferation in a contacted cell may induce the contacted cell to undergo growth retardation, to undergo growth arrest, to undergo programmed cell death (i.e., apoptosis), or to undergo necrotic cell death.

Subjects may include, but are not limited to, horses, cows, sheep, pigs, mice, dogs, cats, primates such as chimpanzees, gorillas, rhesus monkeys, and, humans. In an embodiment, a subject is a human in need of inhibition of Aurora kinase activity.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising a compound of Formula (I) or a salt thereof.

A solution of the invention may be provided in a sealed container, especially one made of glass, either in a unit dosage form or in a multiple dosage form.

Any pharmaceutically acceptable salt of a compound of Formula (I) may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the compound of Formula (I) is a hydrochloric acid salt including a mono, di, or trihydrochloride.

Any solvent which is pharmaceutically acceptable and which is able to dissolve the compound of Formula (I) or a pharmaceutically acceptable salt thereof may be used. The solution of the invention may also contain one or more additional components such as a co-solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

Suitable solvents and co-solubilizing agents may include, but are not limited to, water; sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise a compound of Formula (I) or a pharmaceutically acceptable salt thereof, SWFI, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the compound of Formula (I) or a pharmaceutically acceptable salt thereof may be less than 100 mg/mL, or less than 50 mg/mL, or less than 10 mg/mL, or less than 10 mg/mL and greater than 0.01 mg/mL, or between 0.5 mg/mL and 5 mg/mL, or between 1 mg/mL and 3 mg/mL.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising a compound of Formula (I) or a pharmaceutically acceptable salt thereof in a physiologically acceptable solvent, and which has a pH of from 2.5 to 3.5. For solution formulations, various compounds of the present invention may be more soluble or stable for longer periods in solutions at a pH lower than 6. Further, acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving a compound of Formula (I) or a pharmaceutically acceptable salt thereof in a pharmaceutically acceptable solvent. Where a pharmaceutically acceptable acid salt of a compound of Formula (I) is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

One or more additional components such as co-solubilizing agents, tonicity adjustment agents, stabilizing agents and preservatives, for instance of the kind previously specified, may be added to the solution prior to passing the solution through the sterilizing filter.

Specific pharmaceutical solution formulations with different pH's and concentrations are illustrated in the Examples which follow.

Thus, according to the invention there is also provided a method of inhibiting the growth of a tumor or cancer, which comprises administering to a host suffering from said tumor or cancer an injectable solution according to the invention containing the active drug substance in an amount sufficient to inhibit the growth of said tumor.

The injectable solutions of the invention may be administered by rapid intravenous injection or infusion according to a variety of possible dose schedules.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention. Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartarate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

Other salts which are not pharmaceutically acceptable may be useful in the preparation of compounds of the invention and these form a further aspect of the invention.

In addition, some of the compounds of the present invention may form solvates with water or common organic solvents. Such solvates are also encompassed within the scope of the invention.

Thus, in a further embodiment, there is provided a pharmaceutical composition comprising a compound of the present invention, or a pharmaceutically acceptable salt, solvate, or prodrug thereof, and a pharmaceutically acceptable carrier, excipient, diluent, or mixtures thereof.

The pharmaceutical compositions of the present invention may be useful in therapeutic applications relating to an Aurora kinase-mediated disorder. As used herein, the term "Aurora kinase-mediated disorder" includes any disorder, disease or condition which is caused or characterized by an increase in Aurora kinase expression or activity, or which requires Aurora kinase activity. The term "Aurora kinase-mediated disorder" also includes any disorder, disease or condition in which inhibition of Aurora kinase activity is beneficial. Aurora kinase-mediated disorders include proliferative disorders. Non-limiting examples of proliferative disorders include chronic inflammatory proliferative disorders, e.g., psoriasis and rheumatoid arthritis and chronic pulmonary disease; proliferative ocular disorders, e.g., diabetic retinopathy; benign proliferative disorders, e.g., hemangiomas; restenosis, artherosclerosis, angiogenisis, and cancer.

In an embodiment, the composition is formulated for administration to a subject having or at risk of developing or experiencing a recurrence of an Aurora kinase-mediated disorder. In an embodiment, the pharmaceutical compositions of the invention are those formulated for oral, intravenous, or subcutaneous administration. However, any of the above dosage forms containing a therapeutically effective amount of a compound of the invention are within the bounds of routine experimentation and therefore, within the scope of the instant invention. In some embodiments, the pharmaceutical composition of the invention may further comprise another therapeutic agent. In an embodiment, such other therapeutic agent is one normally administered to a subject with the disease or condition being treated.

As used herein, "therapeutically effective amount" is an amount of the compound of Formula (I) sufficient to cause a detectable decrease in Aurora kinase activity or the severity of an Aurora kinase-mediated disorder. The amount of Aurora kinase inhibitor needed will depend on the effectiveness of the inhibitor for the given cell type and the length of time required to treat the disorder. It should also be understood that a specific dosage and treatment regimen for any particular subject will depend upon a variety of factors, including the activity of the specific compound employed, the age, body weight, general health, sex, and diet of the patient, time of administration, rate of excretion, drug combinations, the judgment of the treating physician, and the severity of the particular disease being treated.

In another aspect, the invention provides a method for treating a subject having or at risk of developing or experiencing a recurrence of an Aurora kinase-mediated disorder. The method comprises the step of administering to the subject a compound or pharmaceutical composition according to the invention. The compounds and pharmaceutical compositions of the invention may be used to achieve a beneficial therapeutic or prophylactic effect, for example, in a subject with a proliferative disorder, as discussed above, such as cancer.

As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated by the methods of the invention include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some other embodiments, the cancer is a hematologic malignancy. Non-limiting examples of hematologic malignancy include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MN); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

In some embodiments, the compound or composition of the invention is used to treat a cancer in which the activity of an Aurora kinase is amplified. In some embodiments, the compound or composition of the invention is used to treat a patient having or at risk of developing or experiencing a recurrence in a cancer selected from the group consisting of colorectal cancer, ovarian cancer, breast cancer, gastric cancer, prostate cancer, and pancreatic cancer. In certain embodiments, the cancer is selected from the group consisting of breast cancer, colorectal cancer, and pancreatic cancer.

In some embodiments, the Aurora kinase inhibitor of the invention is administered in conjunction with another therapeutic agent. The other therapeutic agent may also inhibit Aurora kinase or may operate by a different mechanism. In some embodiments, the other therapeutic agent is one that is normally administered to subject with the disease or condition being treated. The Aurora kinase inhibitor of the invention may be administered with the other therapeutic agent in a single dosage form or as a separate dosage form. When administered as a separate dosage form, the other therapeutic agent may be administered prior to, at the same time as, or following administration of the Aurora kinase inhibitor of the invention.

In some embodiments, the Aurora kinase inhibitor of the invention is administered in conjunction with a therapeutic agent selected from the group consisting of cytotoxic agents, radiotherapy, immunotherapy, or other kinase inhibitors. Non-limiting examples of cytotoxic agents that may be suitable for use in combination with the Aurora kinase inhibitors of the invention include: antimetabolites, including, e.g., capecitibine, gemcitabine, 5-fluorouracil or 5-fluorouracil/leucovorin, fludarabine, cytarabine, mercaptopurine, thioguanine, pentostatin, and methotrexate; topoisomerase inhibitors, including, e.g., etoposide, teniposide, camptothecin, topotecan, irinotecan, doxorubicin, and daunorubicin; vinca alkaloids, including, e.g., vincristine and vinblastin; taxanes, including, e.g., paclitaxel and docetaxel; platinum agents, including, e.g., cisplatin, carboplatin, and oxaliplatin; antibiotics, including, e.g., actinomycin D, bleomycin, mitomycin C, adriamycin, daunorubicin, idarubicin, doxorubicin and pegylated liposomal doxorubicin; alkylating agents such as melphalan, chlorambucil, busulfan, thiotepa, ifosfamide, carmustine, lomustine, semustine, streptozocin, decarbazine, and cyclophosphamide; thalidomide; protein tyrosine kinase inhibitors, including, e.g., imatinib mesylate, erlotinib, and gefitinib; antibodies, including, e.g., trastuzumab, rituximab, cetuximab, and bevacizumab; mitoxantrone; dexamethasone; prednisone; and temozolomide.

EXAMPLES

The present invention may be further understood by reference to the following non-limiting examples. Examples of compounds of the present invention and procedures that may be used to prepare and identify useful compounds of the present invention are described below.

Abbreviations used in the Examples are as follows:
Boc=tert-butoxycarbonyl
DCE=1,2-dichloroethane
DCM=dichloromethane
DIEA=diisopropylethylamine
DMF=N,N-dimethylformamide
EDC=1-ethyl-3-(3-dimethylaminopropyl)-carbodiimide hydrochloride
EtOAc=ethyl acetate
HBTU=O-benzotriazol-1-yl-N,N,N',N'-tetramethyluronium hexafluorophosphate
NMP=N-methylpyrrolidine
THF=tetrahydrofuran LC-MS data was obtained using gradient elution on a parallel MUX™ system, running four Waters 1525 binary HPLC pumps, equipped with a Mux-UV 2488 multichannel UV-V is detector (recording at 215 and 254 nM) and a Leap Technologies HTS PAL Auto sampler using a Waters Xterra MS C18 4.6×50 mm column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. All MS data was obtained in the positive mode unless otherwise noted. $^1$H NMR data was obtained on a Varian 400 MHz spectrometer.

General Procedure A: Preparation of Isothiocyanate 1,1'-thiocarbonylimidazole (1.1 mmol) was added to a solution of amine (1 mmol) in THF/DMF (2 mL, 1:1) and the reaction mixture was stirred at 65-70° C. for 1 h. The product thus formed, was used for further transformation without isolation.

General Procedure B: Thiourea Formation and its Conversion to Aminobenzimidazole To a solution of an isothiocyanate (1 mmol) in THF/DMF (2 mL, 1:1) at room temperature, a phenylene diamine (1 mmol) was added and the contents were stirred at room temperature for 2 h. EDC (1.2 mmol) was then added to the reaction mixture and the contents were stirred at 65-70° C. for 1 h. The reaction mixture was then cooled to room temperature, poured into ice-cold water (10 mL) and the solid was collected by filtration. The crude product thus obtained was purified by flash column chromatography using DCM/methanol as eluent.

General Procedure C: Hydrolysis of Benzoate Ester

A solution of LiOH (12 mmol) in water (5 mL) was added to a solution of ester (3 mmol) in 1:1 THF/MeOH (10 mL) and the resulting mixture was stirred at reflux for 6 h. The reaction mixture was cooled to room temperature and the organic solvents were removed in vacuo. The pH of the resulting suspension was adjusted by the dropwise addition of 10% aq. HCl to pH ~6 and the precipitate thus formed was collected by filtration, washed with water and dried under vacuum. The desired carboxylic acid thus obtained was used without further purification.

General Procedure D: Amide Formation Using a Coupling Agent

To a solution of carboxylic acid (1.0 mmol) in dry DMF or NMP (2.5 mL), HBTU (1.2 mmol) was added in one portion, the reaction mixture was stirred at room temperature for ~30 min. The reaction mixture was then added with the amine (1.1 mmol) and DIEA (1.5 mmol) and the resulting mixture was stirred at room temperature for 6-12 h or at 70-80° C. for 1-3 h. The contents were diluted with ice-cold water (20 mL) and the product was precipitated. The pure product was either isolated after filtration with subsequent washings with water and ethyl acetate or through silica gel column chromatography using DCM/methanol as eluent.

General Procedure E: Amide Formation from Acid Chloride

Oxalyl chloride (10 mmol) was added to a suspension of a carboxylic acid (2 mmol) in dry DCM (4 mL) containing dry DMF (10 μL) and the mixture was stirred at 50° C. for 6-12 h. The mixture was cooled to room temperature and the solvent was removed in vacuo to afford an acid chloride. Toluene (5 mL) was added to the acid chloride and the solvent is removed to dryness in vacuo. This process was repeated to ensure complete removal of residual oxalyl chloride. The acid chloride thus obtained was dissolved in dry DCM (2 mL) and was added dropwise to a suspension of amine (2 mmol) in dry DCM (5 mL) containing pyridine (0.5 mL) at 0° C. The mixture was allowed to warm to room temperature and stirred for 3-5 h. The organic volatiles were removed in vacuo, the precipitate formed was suspended in water (20 mL) and collected by filtration followed by water wash (20 mL). The amide thus obtained was used without further purification.

General Procedure F: Reduction of Nitro to Amine

10% Pd/C (0.1 g) was added to a solution nitro compound (10 mmol) in THF/MeOH (1:1, 50 mL). The resulting mixture was stirred at room temperature under a $H_2$ atmosphere for ~12 h. The contents were then filtered through a pad of Celite and the solid washed with portions of methanol. The filtrate and the washings were combined and evaporated to afford the corresponding amine, which was not purified further and used directly in the next step.

General Procedure G: Ipso Substitution of o-Nitrohaloarene with Ammonia

To a suspension of an o-nitrohaloarene (10 mmol) in methanol (40 mL) was added concentrated aqueous $NH_4OH$ (10 mL). The mixture was heated at 50-60° C. for 4 h. The reaction mixture was concentrated in vacuo and the precipitate formed was collected by filtration, washed with water (50 mL) and dried under vacuum to afford the corresponding o-nitroaniline, which was used for further transformation without further purification.

General Procedure H: Ipso Substitution of p-Nitrohaloarene with Amines

A mixture of a p-nitrohaloarene (5 mmol) and an amine (in excess) was heated as neat or in dioxane at 90° C. for 1-3 h. The volatiles were removed in vacuo and the resulting residue was suspended in ice-cold water (50 mL) with stirring. The resulting precipitate was collected by filtration, washed with water and dried under vacuum to provide the desired product, which was used for further transformation without further purification.

Example 1

Synthesis of 2-(Isoquinolin-3-ylamino)-1H-benzimidazole-5-carboxylic acid benzothiazol-6-ylamide

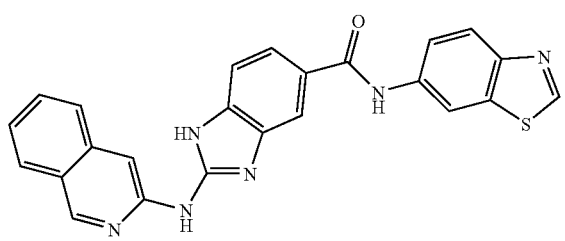

3-Isothiocyanatoisoquinoline was prepared from 3-aminoisoquinoline (5 mmol) as described in general procedure A.

The isothiocyanate from above was reacted with methyl 3,4-diaminobenzoate (5 mmol) followed by cyclization using EDC as described in general procedure B to obtain 2-(Isoquinolin-3-ylamino)-1H-benzimidazole-5-carboxylic acid methyl ester. The ester was hydrolyzed to yield the corresponding carboxylic acid employing general procedure C.

Benzothiazol-6-ylamine (0.25 mmol) was coupled with aforementioned carboxylic acid using HBTU employing general procedure D to provide 2-(Isoquinolin-3-ylamino)-1H-benzimidazole-5-carboxylic acid benzothiazol-6-ylamide. MS: m/z 437 (M+H)$^+$.

Employing the procedure described for Example 1, the following compounds, shown in Table 2, were synthesized.

TABLE 2

| Ex. | Ar | R | MS (m/z) |
|---|---|---|---|
| 2 | Isoquinolin-3-yl | 1H-indazol-5-yl | 420 |
| 3 | Pyridin-2-yl | 1H-indazol-5-yl | 370 |
| 4 | Pyridin-2-yl | 2-Methyl-benzooxazol-5-yl | 385 |
| 5 | Pyridin-2-yl | 1H-indazol-6-yl | 370 |
| 6 | Pyridin-3-yl | 1H-indazol-6-yl | 370 |
| 7 | Pyridin-2-yl | benzothiazol-6-yl | 387 |
| 8 | Pyridin-2-yl | 1H-benzotriazol-5-yl | 371 |
| 9 | 2,4-Dichlorophenyl | 1-Methyl-1H-indazol-5-yl | 452 |
| 10 | 2,4-Dichlorophenyl | 1H-indazol-5-yl | 437 |
| 11 | Phenyl | 1H-indol-5-yl | 369 |
| 12 | Phenyl | 1H-indazol-6-yl | 369 |
| 13 | Pyridin-4-yl | 1H-indazol-6-yl | 370 |
| 14 | Thiazol-2-yl | 1H-indazol-6-yl | 376 |
| 15 | Phenyl | 1H-benzotriazol-5-yl | 370 |
| 16 | Pyridin-2-yl | 1-Methyl-1H-indazol-5-yl | 384 |
| 17 | 2-Chlorophenyl | 1H-indazol-6-yl | 403 |
| 18 | 4,5-Dimethyl-thiazol-2-yl | 1H-indazol-6-yl | 404 |
| 19 | 2,4-Dichlorophenyl | 1H-indazol-6-yl | 437 |
| 20 | Benzothiazol-2-yl | 1H-indazol-6-yl | 426 |
| 21 | 4-phenylthiazol-2-yl | 1H-indazol-6-yl | 452 |
| 22 | 2-Fluorophenyl | 1H-indazol-6-yl | 387 |
| 23 | 2-Ethylphenyl | 1H-indazol-6-yl | 397 |
| 24 | 2,4-Dichlorophenyl | 1H-benzotriazol-5-yl | 439 |

Example 25

Synthesis of 2-(1-Isopropyl-1H-imidazol-2-ylamino)-3H-benzimidazole-5-carboxylic acid (1H-indazol-6-yl)-amide

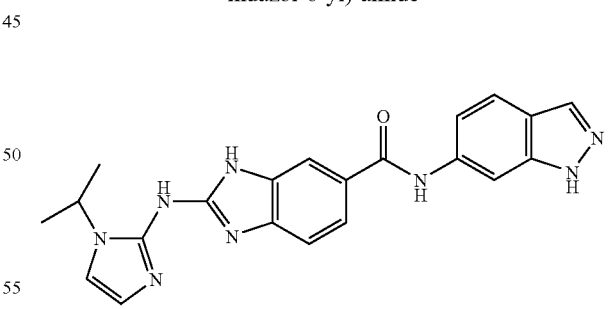

4-Amino-3-nitrobenzoic acid (27 mmol) was coupled with 6-aminoindazole (30 mmol) using HBTU (30 mmol) in dry DMF as the solvent employing the general procedure D to afford 4-amino-N-(1H-indazol-6-yl)-3-nitrobenzamide which was used for further transformation without further purification.

The nitroaniline from above was reduced to 3,4-diamino-N-(1H-indazol-6-yl)-benzamide under hydrogen atmosphere as described in the general procedure F.

2-Bromopropane (7 mmol) and K$_2$CO$_3$ (13 mmol) were added to a solution of 2-nitroimidazole (4 mmol) in DMF (10 mL). The mixture was stirred at 60° C. for 4 h. The contents were cooled to room temperature and water (20 mL) was added and the mixture was extracted with EtOAc (3×10 mL). The combined extracts were dried over MgSO$_4$, filtered and the solvent was removed in vacuo to afford 1-isopropyl-2-nitro-1H-imidazole. The product used for further transformation without further purification.

The nitroimidazole from above was reduced to 1-isopropyl-2-amino-1H-imidazole under hydrogen atmosphere as described in the general procedure F. The aminoimidazole (2 mmol) was converted into 1-isopropyl-2-isothiocyanato-1H-imidazole following the general procedure A.

The isothiocyanate (1 mmol) from above was reacted with 3,4-diamino-N-(1H-indazol-6-yl)-benzamide (1 mmol) followed by cyclization using EDC as described in general procedure B to obtain 2-(1-Isopropyl-1H-imidazol-2-ylamino)-3H-benzimidazole-5-carboxylic acid (1H-indazol-6-yl)-amide. MS: m/z 401 (M+H)$^+$.

Following the procedure in Example 25, 3,4-diamino-N-(1H-indazol-6-yl)-benzamide was utilized to synthesize the compounds listed in Table 3.

TABLE 3

| Ex. | Ar | MS (m/z) |
|---|---|---|
| 26 | 2,4-Dimethylphenyl | 397 |
| 27 | 2-Isopropylphenyl | 411 |
| 28 | 4-Chlorophenyl | 403 |
| 29 | Napthalen-1-yl | 419 |
| 30 | 2-Tert-butylphenyl | 425 |
| 31 | Biphenyl-2-yl | 445 |
| 32 | 2-Propylphenyl | 411 |
| 33 | 2,5-Dichlorophenyl | 438 |
| 34 | 2-Methoxyphenyl | 399 |
| 35 | 2-Trifluoromethylphenyl | 437 |
| 36 | 3-Methylpyridin-2-yl | 384 |
| 37 | 2-Trifluoromethoxyphenyl | 453 |
| 38 | 3-Fluorophenyl | 387 |
| 39 | 4-Fluorophenyl | 387 |
| 40 | 3,5-Difluorophenyl | 405 |
| 41 | 2-Butylphenyl | 425 |
| 42 | 3-Ethyl-6-methylpyridin-2-yl | 412 |
| 43 | 5-Chloro-2-methylphenyl | 417 |
| 44 | 3-Fluoro-2-methylphenyl | 411 |
| 45 | 5-Fluoro-2-methylphenyl | 411 |
| 46 | 3-Chloro-2-methylphenyl | 417 |
| 47 | 1-Cyclopentyl-1H-imidazol-2-yl | 427 |

Example 48

Synthesis of 2-(2-Isopropylphenylamino)-6-(4-methylpiperazin-1-yl)-1H-benzimidazole-5-carboxylic acid (1H-indazol-6-yl)-amide

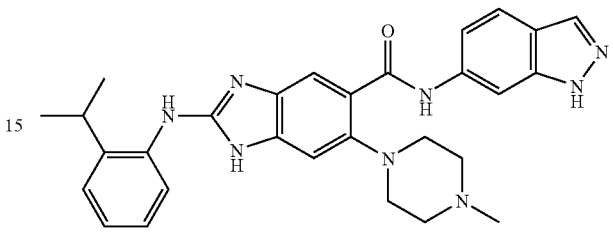

With rapid stirring, solid 2-chloro-4-fluorobenzoic acid (10 mmol) was added in portions in to a flask containing concentrated sulfuric acid (5 mL). The reaction mixture was then cooled to 0° C. and 70% nitric acid (12 mmol) was added dropwise. After the addition was complete the reaction mixture was allowed to warm to room temperature and stirred for 1-2 h. The reaction mixture was poured into 50 g of ice and the solid was collected by filtration, washed with water and dried. The product, 2-chloro-4-fluoro-5-nitrobenzoic acid, was used for further transformation without further purification.

2-chloro-4-fluoro-5-nitrobenzoic acid (5 mmol), obtained as above, was converted to the corresponding acid chloride, which was reacted with 6-aminoindazole (5 mmol) following general procedure E. The product, 2-chloro-4-fluoro-N-(1H-indazol-6-yl)-5-nitrobenzamide, thus obtained as a light orange solid, was used for further transformation without further purification. MS: m/z 335 (M+H)$^+$.

Treatment of 2-chloro-4-fluoro-N-(1H-indazol-6-yl)-5-nitrobenzamide (4 mmol), obtained as above, with ammonium hydroxide (4 mL) as described in general procedure G gave 4-amino-2-chloro-N-(1H-indazol-6-yl)-5-nitrobenzamide as a yellow solid. MS: m/z 332 (M+H)$^+$.

Neat 4-amino-2-chloro-N-(1H-indazol-6-yl)-5-nitrobenzamide (3 mmol) obtained as above was heated with N-methylpiperazine (5 mL), following the general procedure H to afford 4-amino-N-(1H-indazol-6-yl)-2-(4-methylpiperazin-1-yl)-5-nitrobenzamide. The product was reduced to 4,5-diamino-N-(1H-indazol-6-yl)-2-(4-methylpiperazin-1-yl)benzamide under hydrogenation conditions as described in the general procedure F.

The diamine (1 mmol) obtained from above was reacted with 1-isopropyl-2-isothiocyanatobenzene (1 mmol) followed by cyclization using EDC as described in general procedure B to obtain 2-(2-Isopropylphenylamino)-6-(4-methylpiperazin-1-yl)-1H-benzimidazole-5-carboxylic acid (1H-indazol-6-yl)amide. MS: m/z 509 (M+H)$^+$.

Following the procedure in Example 48, 4-amino-2-chloro-N-(1H-indazol-6-yl)-5-nitrobenzamide was utilized to synthesize the compounds listed in Table 4.

TABLE 4

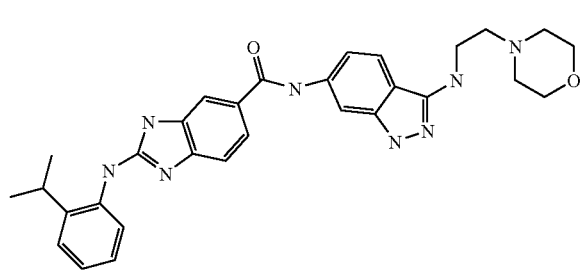

| Ex. | Ar | X | MS (m/z) |
|---|---|---|---|
| 49 | 2-Isopropylphenyl | Morpholin-4-yl | 496 |
| 50 | 2-Trifluoromethylphenyl | 4-Methylpiperazin-1-yl | 535 |
| 51 | 3,5-Difluorophenyl | 4-Methylpiperazin-1-yl | 503 |
| 52 | 2,4-Dichlorophenyl | 4-Methylpiperazin-1-yl | 536 |
| 53 | Thiazol-2-yl | 4-Methylpiperazin-1-yl | 474 |
| 54 | 2-Trifluoromethylphenyl | Morpholin-4-yl | 522 |
| 55 | 3,5-Difluorophenyl | Morpholin-4-yl | 490 |
| 56 | 2,4-Dichlorophenyl | Morpholin-4-yl | 522 |
| 57 | 2-Trifluoromethylphenyl | Piperidin-1-yl | 520 |
| 58 | 3-Methylpyridin-2-yl | 4-Methylpiperazin-1-yl | 482 |
| 59 | Thiazol-2-yl | Morpholin-4-yl | 461 |
| 60 | 3-Methylpyridin-2-yl | Morpholin-4-yl | 469 |
| 61 | 1-Isopropyl-1H-imidazol-2-yl | 4-Methylpiperazin-1-yl | 499 |
| 62 | 1-Cyclopentyl-1H-imidazol-2-yl | 4-Methylpiperazin-1-yl | 525 |
| 63 | 1-Isopropyl-1H-imidazol-2-yl | Morpholin-4-yl | 486 |
| 64 | 1-Cyclopentyl-1H-imidazol-2-yl | Morpholin-4-yl | 512 |
| 65 | 2-Ethyl-2H-pyrazol-3-yl | Morpholin-4-yl | 472 |

Example 66

Synthesis of 2-(2-Isopropylphenylamino)-3H-benzimidazole-5-carboxylic acid [3-(2-morpholin-4-yl-ethylamino)-1H-indazol-6-yl]-amide

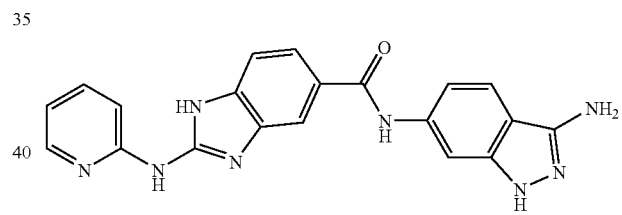

To a solution of 2,6-dinitro-2H-indazole (1 mmol) (prepared by nitration of 6-nitroindazole; Wrzeciono, et al., E. *Pharmazie*, 1980, 35, 593-596) in dry THF (4 mL) at 0° C., 2-morpholin-4-yl-ethylamine (2 mmol) was added dropwise. The reaction mixture was allowed to warm to room temperature and stirred for 12 h. The contents were diluted with ethyl acetate (20 mL), washed with water (2×10 mL), and brine (10 mL) and dried over anhydrous sodium sulfate. The solvent was removed in vacuo to yield 3-(2-morpholin-4-yl-ethylamino)-6-nitro-1H-indazole as a brown solid, which was reduced to 3-(2-morpholin-4-yl-ethylamino)-1H-indazol-6-ylamine by hydrogenation following general procedure F.

1-Isopropyl-2-isothiocyanatobenzene (5 mmol) and methyl 3,4-diaminobenzoate (5 mmol) were reacted, following general procedure B, to yield 2-(2-Isopropylphenylamino)-1H-benzimidazole-5-carboxylic acid methyl ester, which was purified by silica gel chromatography using DCM/ethyl acetate as eluent.

The ester obtained as above was hydrolyzed using general procedure C to yield 2-(2-isopropylphenylamino)-1H-benzimidazole-5-carboxylic acid. The carboxylic acid (0.25 mmol) was coupled with 3-(2-morpholin-4-yl-ethylamino)-1H-indazol-6-ylamine (0.25 mmol) using HBTU employing general procedure D. The product, 2-(2-Isopropylphenylamino)-3H-benzimidazole-5-carboxylic acid [3-(2-morpholin-4-yl-ethylamino)-1H-indazol-6-yl]-amide, was obtained after purification by silica gel chromatography using DCM/methanol as eluent. MS: m/z 539 (M+H)$^+$.

Employing the procedure described for Example 66, the following compounds, shown in Table 5, were synthesized.

TABLE 5

| Ex. | R | MS (m/z) |
|---|---|---|
| 67 | 3-Morpholin-4-yl-propylamino | 553 |
| 68 | Methylamino | 440 |

Example 69

Synthesis of 2-(pyridin-2-ylamino)-1H-benzimidazole-5-carboxylic acid (3-amino-1H-indazol-6-yl)-amide To a solution of 2-fluoro-4-nitrobenzonitrile (10 mmol) in isopropanol (30 mL) was added aqueous hydrazine (4 mL). The resulting solution was heated at 80° C. for 12 h. The reaction mixture was then concentrated, water (30 mL) was added, and the solution was extracted with ethyl acetate (2×25 mL). The combined organics were washed with water (30 mL) and brine (30 mL) and dried over anhydrous sodium sulfate. The volatiles were removed in vacuo yielding 3-amino-6-nitroindazole as an orange solid, which was utilized for further transformation without further purification.

The nitro compound from above was hydrogenated, following general procedure F, to yield 3,6-diaminoindazole.

2-Isothiocyanatopyridine (4 mmol), prepared from 2-aminopyridine employing general procedure A, was reacted with methyl 3,4-diaminobenzoate as described in general procedure B to afford 2-(pyridin-2-ylamino)-1H-benzimidazole-5-carboxylic acid methyl ester. This ester was hydrolyzed, following general procedure C, to obtain 2-(pyridin-2-ylamino)-1H-benzimidazole-5-carboxylic acid.

The carboxylic acid (0.5 mmol) from above was coupled with aforementioned 3,6-diaminoindazole (0.5 mmol) using HBTU as described in general procedure D to afford 2-(pyridin-2-ylamino)-1H-benzimidazole-5-carboxylic acid (3-amino-1H-indazol-6-yl)-amide. MS: m/z 385 (M+H)$^+$.

Example 70

Synthesis of 2-(2-Isopropylphenylamino)-3H-benz-imidazole-5-carboxylic acid {3-[(1-methylpiperidine-4-carbonyl)-amino]-1H-indazol-6-yl}-amide

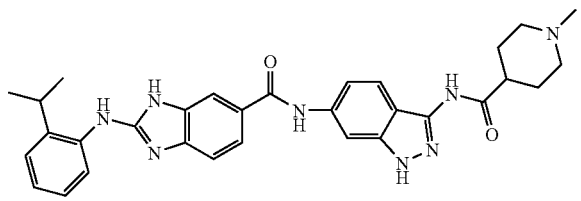

1-Methylpiperidine-4-carbonyl chloride (1 mmol), prepared from its corresponding carboxylic acid using general procedure E, was reacted with 3,6-diaminoindazole (1 mmol) (see Example 69) employing general procedure E to yield 1-methylpiperidine-4-carboxylic acid (6-amino-1H-indazol-3-yl)-amide.

2-(2-Isopropylphenylamino)-3H-benzimidazole-5-carboxylic acid (0.3 mmol; see Example 66) was coupled with aforementioned 1-methylpiperidine-4-carboxylic acid (6-amino-1H-indazol-3-yl)-amide (0.3 mmol) using HBTU as described in general procedure D to afford the desired product, 2-(2-Isopropylphenylamino)-3H-benzimidazole-5-carboxylic acid {3-[(1-methylpiperidine-4-carbonyl)-amino]-1H-indazol-6-yl}-amide. MS: m/z 551 (M+H)$^+$.

Employing the procedure described for Example 70, the following compounds, shown in Table 6, were synthesized.

TABLE 6

| Ex. | Ar | R | MS (m/z) |
|---|---|---|---|
| 71 | Pyridin-2-yl | Methyl | 427 |
| 72 | 2,4-Dichlorophenyl | Methyl | 494 |
| 73 | 2,4-Dichlorophenyl | Phenyl | 556 |

Example 74

Synthesis of 2-(2-isopropylphenylamino)-3H-benzimidazole-5-carboxylic acid (3-methoxy-1H-indazol-6-yl)-amide

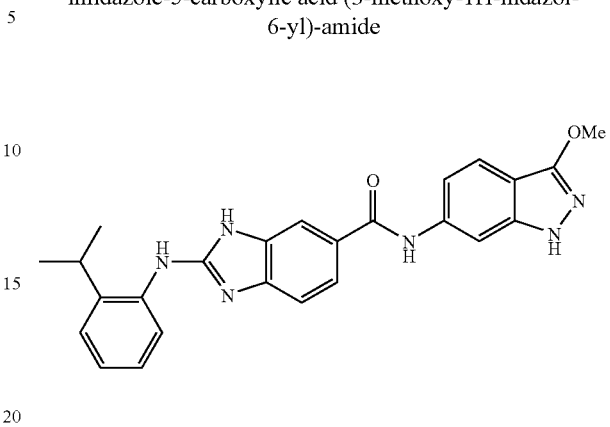

To a solution of 2,6-dinitro-2H-indazole(1 mmol) (prepared by nitration of 6-nitroindazole; Wrzeciono, et al., E. *Pharmazie,* 1980, 35, 593-596) in dry THF (4 mL) at 0° C., solid sodium methoxide (4 mmol) was added in portions. The reaction mixture was allowed to warm to room temperature and stirred for 12 h. The contents were diluted with ethyl acetate (20 mL), washed with water (2×10 mL) and brine (10 mL) and dried over anhydrous sodium sulfate. The solvent was removed in vacuo to yield 3-methoxy-6-nitro-1H-indazole as a brown solid, which was reduced to 3-methoxy-1H-indazol-6-ylamine by hydrogenation following general procedure F.

2-(2-Isopropylphenylamino)-3H-benzimidazole-5-carboxylic acid (0.3 mmol; see Example 66) was coupled with aforementioned 3-methoxy-1H-indazol-6-ylamine (0.3 mmol) using HBTU as described in general procedure D to afford the desired product, 2-(2-isopropylphenylamino)-3H-benzimidazole-5-carboxylic acid (3-methoxy-1H-indazol-6-yl)-amide. MS: m/z 441 (M+H)$^+$.

Example 75

Synthesis of 2-(2 isopropylphenylamino)-3H-benzimidazole-5-carboxylic acid [3-(2-morpholin-4-ylethoxy)-1H-indazol-6-yl]-amide

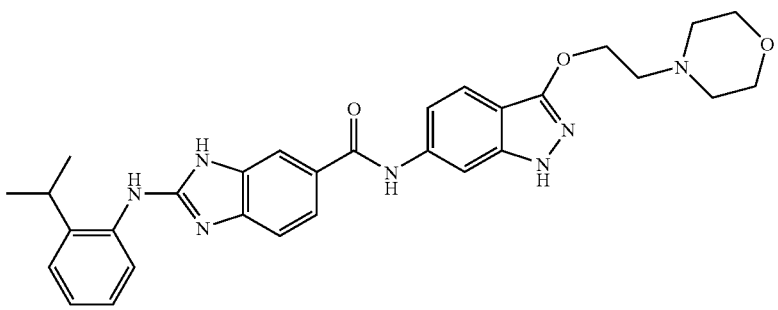

To a solution of 2-morpholin-4-yl-ethanol (3 mmol) in dry THF (6 mL) sodium hydride (4 mmol; 60% dispersion in oil) was added at 0° C. in portions. The alkoxide thus formed, was reacted with 2,6-dinitro-2H-indazole(1 mmol) as described in Example 74 to yield 3-(2-morpholin-4-yletoxy)-6-nitro-1H-indazole as a brown solid which was reduced to 3-(2-morpholin-4-yletoxy)-1H-indazol-6-ylamine by hydrogenation following general procedure F.

2-(2-Isopropylphenylamino)-3H-benzimidazole-5-carboxylic acid (0.3 mmol; see Example 66) was coupled with aforementioned 3-(2-morpholin-4-yletoxy)-1H-indazol-6-ylamine (0.3 mmol) using HBTU as described in general procedure D to afford the desired product, 2-(2 isopropylphenylamino)-3H-benzimidazole-5-carboxylic acid [3-(2-morpholin-4-yletoxy)-1H-indazol-6-yl]-amide. MS: m/z 540 (M+H)$^+$.

Example 76

Synthesis of 2-(2,4-dichlorophenylamino)-3H-benzimidazole-5-carboxylic acid (3-morpholin-4-ylmethyl-1H-indazol-6-yl)-amide

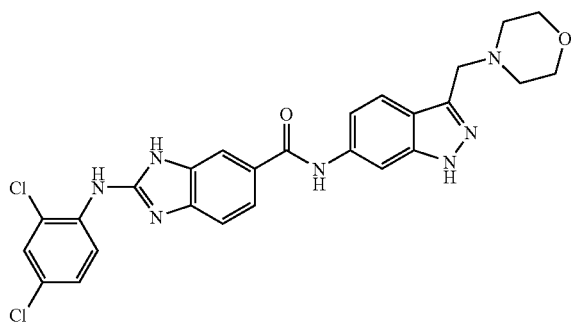

To a solution of 6-nitro-1H-indazole-3-carbaldehyde (0.5 mmol; prepared from 6-nitroindole; Zhang et al., *J. Med. Chem.* 2001, 44, 1021-1024) in dry THF (1 mL), morpholine (1 mmol) and acetic acid (2 drops) were added at room temperature and the mixture was stirred for 1 h. The reaction mixture was treated with solid NaCNBH$_3$ (2 mmol) with stirring continued for additional 4 h. The contents were poured into water and extracted with ethyl acetate (2×10 mL). The combined organics were washed with saturated aqueous NaHCO$_3$ (10 mL) and brine (10 mL) and dried over anhydrous sodium sulfate. Removal of the solvent in vacuo afforded the desired product, 3-(morpholin-4-yl)methyl-6-nitro-1H-indazole.

Hydrogenation of the aforementioned nitro compound, following the general procedure F gave 3-(morpholin-4-y)lmethyl-1H-indazol-6-ylamine.

2,4-Dichloro-1-isothiocyanatobenzene (5 mmol) and methyl 3,4-diaminobenzoate (5 mmol) were reacted, following general procedure B, to yield 2-(2,4-dichlorophenylamino)-3H-benzimidazole-5-carboxylic acid methyl ester, which was purified by silica gel chromatography using DCM/ethyl acetate as eluent.

The ester obtained as above was hydrolyzed using general procedure C to yield 2-(2,4-dichlorophenylamino)-3H-benzimidazole-5-carboxylic acid. The carboxylic acid (0.25 mmol) was coupled with 3-(morpholin-4-y)lmethyl-1H-indazol-6-ylamine (0.25 mmol) using HBTU employing general procedure D. The product, 2-(2,4-dichlorophenylamino)-3H-benzimidazole-5-carboxylic acid (3-morpholin-4-ylmethyl-1H-indazol-6-yl)-amide, was obtained as a light brown solid after purification by silica gel chromatography using DCM/methanol as eluent. MS: m/z 536 (M+H)$^+$.

Example 77

Synthesis of 2-(2,4-dichlorophenylamino)-3H-benzimidazole-5-carboxylic acid (3-methyl-1H-indazol-6-yl)-amide

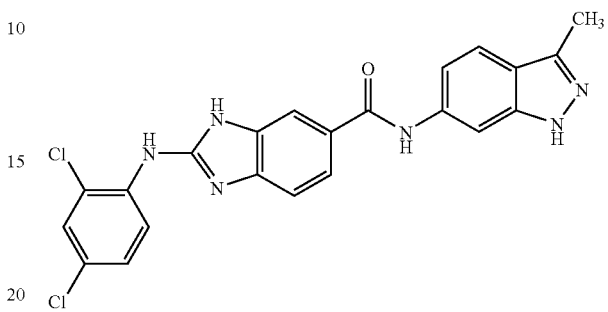

To a solution of 6-nitro-1H-indazole-3-carbaldehyde (0.5 mmol; prepared from 6-nitroindole; Zhang et al., *J. Med. Chem.* 2001, 44, 1021-1024) in ethanol (2 mL), solid KOH (5 mmol) and aqueous hydrazine (0.5 mL) were added and the contents were irradiated under microwave conditions at 80° C. for 10 min. The reaction mixture was neutralized with acetic acid to pH ~7, concentrated in vacuo, diluted with water and extracted with ethyl acetate (3×8 mL). The combined organics were washed with saturated aqueous NaHCO$_3$ (10 mL) and brine (10 mL) and dried over anhydrous sodium sulfate. Removal of the solvent in vacuo afforded the desired product, 3-methyl-1H-indazol-6-ylamine.

The amine (0.25 mmol), obtained as above, was coupled with 2-(2,4-dichloro-phenylamino)-3H-benzimidazole-5-carboxylic acid (0.25 mmol; see Example 76) using HBTU employing general procedure D. The product, 2-(2,4-dichlorophenylamino)-3H-benzimidazole-5-carboxylic acid (3-methyl-1H-indazol-6-yl)-amide, was obtained as a light brown solid after purification by silica gel chromatography using DCM/methanol as eluent. MS: m/z 452 (M+H)$^+$.

Example 78

Synthesis of 2-(2-ethylphenylamino)-3H-benzimidazole-5-carboxylic acid (3-chloro-1H-indazol-6-yl)-amide

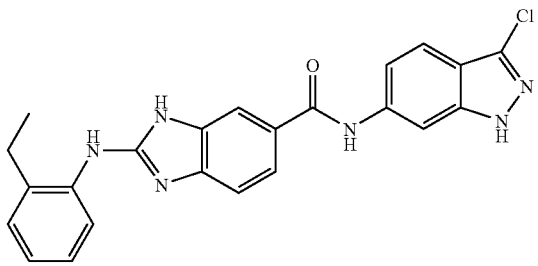

To a solution of 6-nitroindazole (2 mmol) in DCE (5 mL), sulfuryl chloride (10 mmol) was added and the resulting mixture was heated 80° C. for 3-5 h. The reaction mixture was concentrated, added with 5% aqueous Na$_2$CO$_3$ solution (20 mL) and extracted with EtOAc (2×15 mL). The combined organics were then washed with water (20 mL) and brine (20 mL) and dried over anhydrous Na$_2$SO$_4$. Removal of volatiles afforded 3-chloro-6-nitro-1H-indazole as a yellow solid.

To a solution of nitro compound (0.5 mmol) from above in methanol (2 mL), was added solid sodium hydrosulfite (3 mmol) and concentrated ammonium hydroxide (0.25 mL). The resulting mixture was stirred at room temperature for 12 h. The contents were filtered through Celite and the solvent was removed in vacuo. The residue obtained was purified by silica gel chromatography using ethyl acetate/hexane as eluant to yield 3-chloro-1H-indazol-6-ylamine as a light brown solid.

2-Ethyl-1-isothiocyanatobenzene (3 mmol) and methyl 3,4-diaminobenzoate (3 mmol) were reacted, following general procedure B, to yield 2-(2-ethylphenylamino)-3H-benzimidazole-5-carboxylic acid methyl ester, which was purified by silica gel chromatography using DCM/ethyl acetate as eluent.

The ester obtained as above was hydrolyzed using general procedure C to yield 2-(2-ethylphenylamino)-3H-benzimidazole-5-carboxylic acid. The carboxylic acid (0.25 mmol) was coupled with 3-(morpholin-4-y)lmethyl-1H-indazol-6-ylamine (0.25 mmol) using HBTU employing general procedure D. The product, 2-(2-ethylphenylamino)-3H-benzimidazole-5-carboxylic acid (3-chloro-1H-indazol-6-yl)-amide, was obtained as a light brown solid after purification by silica gel chromatography using DCM/methanol as eluent. MS: m/z 431 (M+H)⁺.

Example 79

Synthesis of 2-[6-(1H-indazol-6-ylcarbamoyl)-1H-benzimidazol-2-ylamino]-6,7-dihydro-4H-thiazolo [5,4-c]pyridine-5-carboxylic acid tert-butyl ester

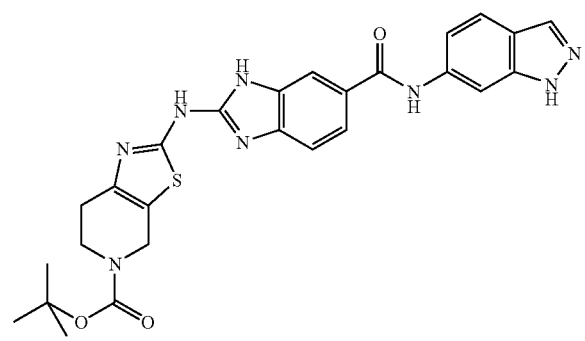

To a solution of 1-Boc-4-piperidone (5 mmol) in dry THF (20 mL) was added solid Ba₂CO₃ (10 mmol). The resulting mixture was stirred vigorously. The reaction mixture was treated with pyrrolidone hydrotribromide (5.5 mmol) in portions at room temperature. After 3h, the contents were filtered and the solvent removed. The crude reaction mixture containing the product, 3-bromo-4-oxo-piperidine-1-carboxylic acid tert-butyl ester, was used for further transformation without further purification.

To a solution of the bromo compound (5 mmol), obtained as above, in acetone (20 mL) was added solid thiourea (6 mmol) and solid K₂CO₃ (10 mmol), and the reaction mixture was stirred at room temperature for 12 h. To the reaction mixture was added BOC anhydride (5 mmol), and the reaction was stirred for 4 h. The contents were then filtered, and the solvent was removed. The residue obtained was purified by silica gel chromatography using DCM/methanol as eluent. The product, 2-amino-6,7-dihydro-4H-thiazolo[5,4-c]pyridine-5-carboxylic acid tert-butyl ester, was obtained a light yellow solid.

The amine (0.5 mmol) from above was converted to corresponding isothiocyanate using general procedure A, which was then reacted with 3,4-diamino-N-(1H-indazol-6-yl)-benzamide (0.5 mmol; see Example 25) according to general procedure B to yield 2-[6-(1H-indazol-6-ylcarbamoyl)-1H-benzimidazol-2-ylamino]-6,7-dihydro-4H-thiazolo[5,4-c]pyridine-5-carboxylic acid tert-butyl ester. MS: m/z 531 (M+H)⁺.

Example 80

Synthesis of 2-(4,5,6,7-tetrahydrothiazolo[5,4-c]pyridin-2-ylamino)-3H-benzimidazole-5-carboxylic acid (1H-indazol-6-yl)-amide

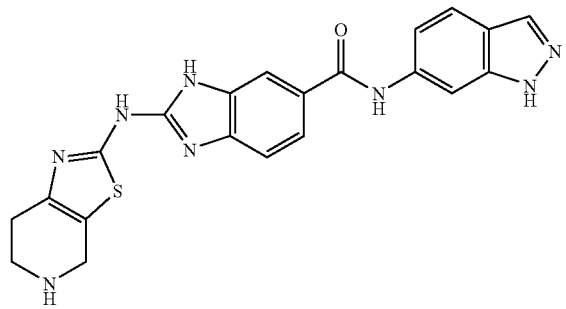

To a solution of 2-[6-(1H-indazol-6-ylcarbamoyl)-1H-benzimidazol-2-ylamino]-6,7-dihydro-4H-thiazolo[5,4-c]pyridine-5-carboxylic acid tert-butyl ester (0.25 mmol; see Example 79) in methanol (1 mL), 4M HCl in dioxane (0.5 mL) was added. The resulting mixture was stirred at room temperature for 5-6 h. The volatiles were removed in vacuo, the residue obtained was suspended in ether. The solid obtained was collected by filtration, washed with ether and dried in vacuo to afford 2-(4,5,6,7-tetrahydro-thiazolo[5,4-c]pyridin-2-ylamino)-3H-benzimidazole-5-carboxylic acid (1H-indazol-6-yl)-amide as a hydrochloride salt. MS: m/z 431 (M+H)⁺.

Example 81

Synthesis of 2-(2-isopropylphenylamino)-3H-benzimidazole-5-carboxylic acid [1-(2-hydroxy-ethyl)-1H-indazol-5-yl]-amide

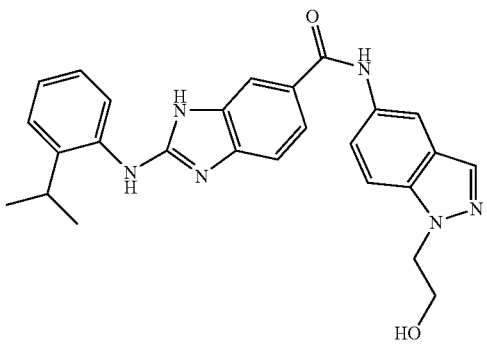

To a solution of 2-chloro-5-nitrobenzaldehyde (4 mmol) in ethanol (10 mL) was added aqueous hydrazine (5 mmol), and the resulting solution was heated at reflux for 2 h to complete hydrazone formation. DIEA (10 mmol) was added to the reaction mixture, and the reaction was subjected to microwave irradiation at 150° C. for 8-10 h. After removal of volatiles in vacuo, the residue obtained was dissolved in EtOAc (30 mL), washed with water (20 mL) and brine (20 mL) and dried over anhydrous sodium sulfate. The solvent was removed in vacuo to yield the product, 2-(5-nitroindazol-1-yl)-ethanol.

The nitro compound from above was reduced under hydrogenation conditions as described in general procedure F to afford 2-(5-aminoindazol-1-yl)-ethanol. The aminoindazole (0.3 mmol) was coupled with 2-(2-Isopropylphenylamino)-1H-benzimidazole-5-carboxylic acid (0.3 mmol; see Example 66) using HBTU as described in general procedure D to provide of 2-(2-isopropylphenylamino)-3H-benzimidazole-5-carboxylic acid [1-(2-hydroxy-ethyl)-1H-indazol-5-yl]-amide. MS: m/z 455 (M+H)$^+$.

Example 82

Synthesis of 2-(2-cyclohexylphenylamino)-3H-benzimidazole-5-carboxylic acid (1H-indazol-6-yl)-amide

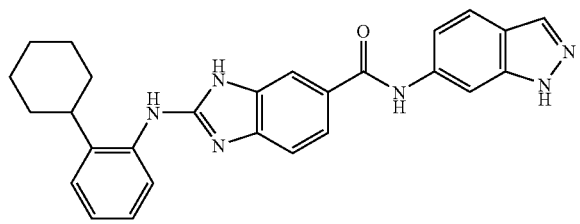

To a solution of 1-bromo-2-cyclohexyl-benzene (5 mmol) in dioxane (20 mL) was added solid Pd(OAc)$_2$ (0.1 g) and solid CsCO$_3$ (10 mmol). tert-Butyl carbamate (7 mmol) was added to the reaction mixture, and the contents were heated at 80° C. for 2 h. The reaction mixture was cooled to room temperature and filtered through Celite. The solvent was removed in vacuo and the residue obtained was purified by flash column chromatography using DCM as eluant to yield (2-cyclohexylphenyl)-carbamic acid tert-butyl ester.

The carbamate obtained as above was treated with 4 M HCl in dioxane following the procedure described in Example 80 to afford 2-cyclohexylphenylamine as a hydrochloride salt.

To a solution of aforementioned amine hydrochloride (1 mmol) in dry DMF (2 mL) was added DIEA (1.5 mmol) and 1,1'-thiocarbonylimidazole (1 mmol). The reaction mixture was heated at 70° C. for 1 h to provide 1-cyclohexyl-2-isothiocyanatobenzene as described in general procedure A.

The isothiocyanate (0.5 mmol) was reacted with 3,4-diamino-N-(1H-indazol-6-yl)-benzamide (0.5 mmol; see Example 25) according to general procedure B to yield 2-(2-cyclohexylphenylamino)-3H-benzimidazole-5-carboxylic acid (1H-indazol-6-yl)-amide. MS: m/z 451 (M+H)$^+$.

Example 83

Synthesis of 2-(3-methylthiophen-2-ylamino)-3H-benzimidazole-5-carboxylic acid (1H-indazol-6-yl)-amide

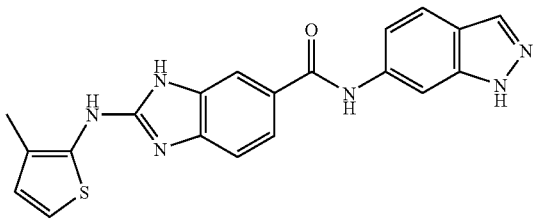

To a solution of 3-methylthiophene-2-carboxylic acid (7 mmol) in anhydrous dioxane (20 mL) was added diphenyl phosphoryl azide (7 mmol), tert-butanol (6 mL) and TEA (1 mL). The resulting mixture was stirred at reflux for 16 h. The reaction mixture was cooled to room temperature, diluted with H$_2$O (40 mL), and was extracted with EtOAc (3×20 mL). The combined extracts were dried (MgSO$_4$) and the solvent was removed in vacuo. The residue obtained was purified by flash column chromatography using hexanes/EtOAc (7:3) as eluent to afford (3-methylthiophen-2-yl)-carbamic acid tert-butyl ester.

To a solution of carbamate (3 mmol), obtained as above, in dry DCM (10 mL) was added with 4M HCl in dioxane (8 mL). The mixture was stirred at room temperature for 2 h. The solvent was removed in vacuo. The solid obtained washed with anhydrous Et$_2$O (3×10 mL) and dried under reduced pressure to afford 3-methylthiophen-2-ylamine as hydrochloride salt.

To a solution of aforementioned amine hydrochloride (1 mmol) in dry DMF (2 mL) was added DIEA (1.5 mmol) and 1,1'-thiocarbonylimidazole (1 mmol). The reaction mixture was heated at 70° C. for 1 h to provide 1-cyclohexyl-2-isothiocyanatobenzene as described in general procedure A.

The isothiocyanate (0.5 mmol) was reacted with 3,4-diamino-N-(1H-indazol-6-yl)-benzamide (0.5 mmol; see Example 25) according to general procedure B to yield 2-(2-cyclohexylphenylamino)-3H-benzimidazole-5-carboxylic acid (1H-indazol-6-yl)-amide. MS: m/z 389 (M+H)$^+$.

Example 84

Synthesis of 1H-indazole-6-carboxylic acid [2-(2-isopropylphenylamino)-3H-benzimidazol-5-yl]-amide

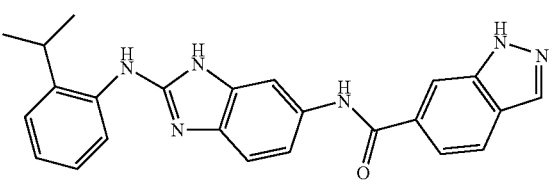

To a solution of 2-chloro-5-nitro-1H-benzimidazole (1.5 mmol; prepared from nitration of 2-chloro-1H-benzimidazole; Galy et al., *J. Heterocycl. Chem.* 1997, 34, 6, 1781-1788) in dry NMP (3 mL) was added 2-isopropylaniline (4 mmol). The resulting solution was subjected to microwave irradiation at 150° C. for 1 h. The contents were cooled to room temperature, diluted with water (20 mL) and extracted with EtOAc (2×15 mL). The combined extracts were then washed with water (20 mL) and brine (20 mL) and dried over anhydrous sodium sulfate. The solvent was removed in vacuo and the residue obtained was purified by silica gel chromatography using EtOAc/hexane as eluent to obtain (2-isopropylphenyl)-(5-nitro-1H-benzimidazol-2-yl)-amine as light yellow solid.

The nitro compound (1 mmol) as above was reduced under hydrogenation conditions as described in general procedure F to afford N$^2$-(2-isopropylphenyl)-1H-benzimidazole-2,5-diamine.

Methyl Indazole-6-carboxylate (4 mmol; Batt et al., *J. Med. Chem.* 2000, 43, 41-58) was hydrolyzed as in general procedure C to obtain 1H-Indazole-6-carboxylic acid. The carboxylic acid (0.5 mmol) was coupled with aforementioned N$^2$-(2-isopropylphenyl)-1H-benzimidazole-2,5-diamine (0.5 mmol) using HBTU as described in general procedure D to yield 1H-indazole-6-carboxylic acid [2-(2-isopropylphenylamino)-3H-benzimidazol-5-yl]-amide as an off-white solid. MS: m/z 411 (M+H)$^+$.

Example 85

Synthesis of 6-(4-methylpiperazin-1-yl)-2-(2-trifluoromethylphenylamino)-1H-benzimidazole-5-carboxylic acid (1H-indazol-5-yl)-amide

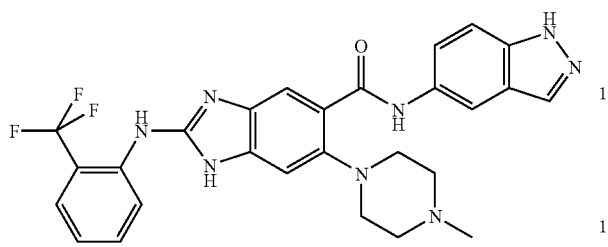

2-Chloro-4-fluoro-N-(1H-indazol-5-yl)-5-nitrobenzamide was obtained from 2-chloro-4-fluoro-5-nitrobenzoic acid (5 mmol) and 5-aminoindazole (5 mmol) following the procedure described in Example 48. The product, obtained as a yellow solid, was used for further transformation without further purification. MS: m/z 335 (M+H)$^+$.

Treatment of 2-Chloro-4-fluoro-N-(1H-indazol-5-yl)-5-nitrobenzamide (4 mmol), obtained as above, with ammonium hydroxide (4 mL) as described in general procedure G gave 4-amino-2-chloro-N-(1H-indazol-5-yl)-5-nitrobenzamide as a yellow solid. MS: m/z 332 (M+H)$^+$.

4-amino-2-chloro-N-(1H-indazol-5-yl)-5-nitrobenzamide (3 mmol) from above was reacted N-methylpiperazine (5 mL), following the procedure in Example 48. The product formed was reduced to 4,5-diamino-N-(1H-indazol-5-yl)-2-(4-methylpiperazin-1-yl)benzamide under hydrogenation conditions as described in the general procedure F.

The diamine (1 mmol) obtained from above was reacted with 1-trifluoromethyl-2-isothiocyanatobenzene (1 mmol) followed by cyclization using EDC as described in general procedure B to obtain 2-(2-trifluoromethylphenylamino)-6-(4-methylpiperazin 1-yl)-1H-benzimidazole-5-carboxylic acid (1H-indazol-5-yl)amide. MS: m/z 535 (M+H)$^+$.

Example 86

Synthesis of 6-morpholin-4-yl-2-(2-trifluoromethylphenylamino)-1H-benzimidazole-5-carboxylic acid (1H-indazol-5-yl)-amide

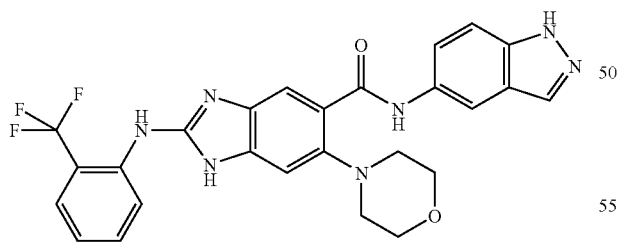

4-Amino-2-chloro-N-(1H-indazol-5-yl)-5-nitrobenzamide (3 mmol; see Example 85) was reacted morpholine (5 mL), following the procedure G. The product formed was reduced to 4,5-diamino-N-(1H-indazol-5-yl)-2-morpholin-4-yl-benzamide under hydrogenation conditions as described in the general procedure F.

The diamine (1 mmol) obtained from above was reacted with 1-trifluoromethyl-2-isothiocyanatobenzene (1 mmol) followed by cyclization using EDC as described in general procedure B to obtain 6-morpholin-4-yl-2-(2-trifluoromethylphenylamino)-1H-benzimidazole-5-carboxylic acid (1H-indazol-5-yl)-amide. MS: m/z 522 (M+H)$^+$.

Example 87

Synthesis of 4-[6-(1H-indazol-6-ylcarbamoyl)-2-(2-trifluoromethylphenylamino)-3H-benzimidazol-5-yl]-piperazine-1-carboxylic acid tert-butyl ester

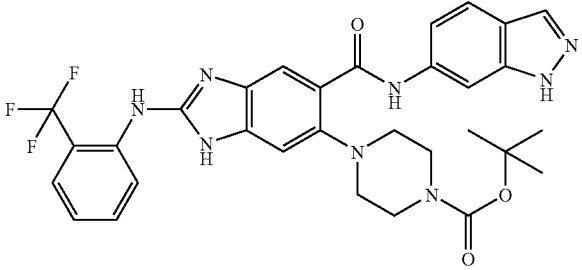

4-amino-2-chloro-N-(1H-indazol-6-yl)-5-nitrobenzamide (3 mmol; see Example 48) in dioxane (5 mL) was reacted with piperazine (9 mmol) following the general procedure H to afford 4-amino-N-(1H-indazol-6-yl)-5-nitro-2-piperazin-1-yl-benzamide. The product was dissolved in dry THF (6 mL) and was treated with BOC anhydride (3.6 mmol) and stirred for 4-6 h. The solvent was removed to dryness, and the residue obtained was suspended in ether (50 mL) with stirring. The solid formed was collected by filtration, washed with ether and dried in vacuo to afford 4-[5-amino-2-(1H-indazol-6-ylcarbamoyl)-4-nitro-phenyl]-piperazine-1-carboxylic acid tert-butyl ester.

To a solution of nitro compound (1 mmol) from above in methanol (4 mL) was added solid sodium hydrosulfite (4 mmol) and concentrated ammonium hydroxide (0.5 mL). The resulting mixture was heated at reflux for 5-8 h. The reaction was concentrated, and the residue was taken up in THF (20 mL) with vigorous stirring. The contents were then filtered through Celite and the solvent was removed in vacuo to provide 4-[4,5-diamino-2-(1H-indazol-6-ylcarbamoyl)-phenyl]piperazine-1-carboxylic acid tert-butyl ester which was used for further transformation without further purification.

The diamine (0.3 mmol) from above was reacted with 1-trifluoromethyl-2-isothiocyanatobenzene (0.3 mmol) followed by cyclization using EDC as described in general procedure B to obtain 4-[6-(1H-indazol-6-ylcarbamoyl)-2-(2-trifluoromethylphenylamino)-3H-benzimidazol-5-yl]-piperazine-1-carboxylic acid tert-butyl ester. MS: m/z 621 (M+H)$^+$.

Example 88

Synthesis of 6-piperazin-1-yl-2-(2-trifluoromethylphenylamino)-1H-benzimidazole-5-carboxylic acid (1H-indazol-6-yl)-amide

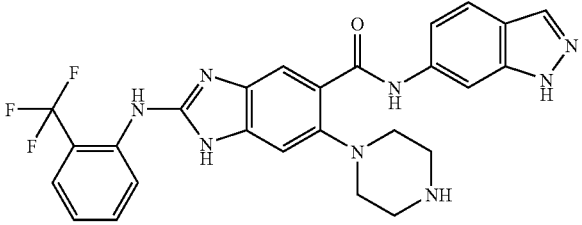

The product from Example 87 was treated with 4M HCl in dioxane employing the procedure described for Example 80 to afford of 6-piperazin-1-yl-2-(2-trifluoromethylphenylamino)-1H-benzimidazole-5-carboxylic acid (1H-indazol-6-yl)-amide as a hydrochloride salt. MS: m/z 521 (M+H)$^+$.

Example 89

Synthesis of 4-[6-(1H-indazol-6-ylcarbamoyl)-2-(3-methylpyridin-2-ylamino)-3H-benzimidazol-5-yl]-piperazine-1-carboxylic acid tert-butyl ester

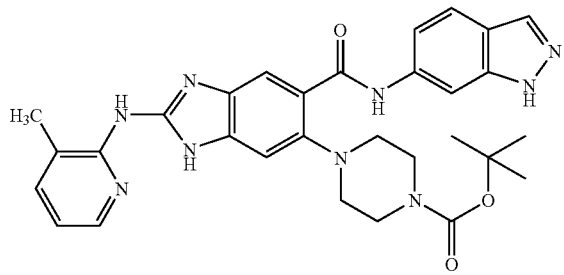

4-[4,5-Diamino-2-(1H-indazol-6-ylcarbamoyl)-phenyl]piperazine-1-carboxylic acid tert-butyl ester (see Example 87) was reacted with 2-isothiocyanato-3-methylpyridine (0.3 mmol; prepared from 3-methylpyridin-2-ylamine following general procedure A) followed by cyclization using EDC as described in general procedure B to obtain 4-[6-(1H-indazol-6-ylcarbamoyl)-2-(3-methylpyridin-2-ylamino)-3H-benzimidazol-5-yl]-piperazine-1-carboxylic acid tert-butyl ester. MS: m/z 568 $(M+H)^+$.

Example 90

Synthesis of 2-(3-methylpyridin-2-ylamino)-6-piperazin-1-yl-1H-benzimidazole-5-carboxylic acid (1H-indazol-6-yl)-amide

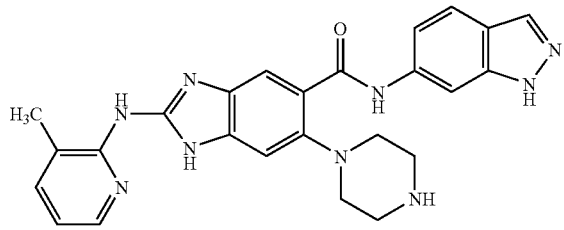

The product from Example 89 was treated with 4M HCl in dioxane employing the procedure described for Example 80 to afford of 2-(3-methylpyridin-2-ylamino)-6-piperazin-1-yl-1H-benzimidazole-5-carboxylic acid (1H-indazol-6-yl)-amide as a hydrochloride salt. MS: m/z 468 $(M+H)^+$.

Example 91

Synthesis 2-(2,6-diethylphenylamino)-3H-benzimidazole-5-carboxylic acid (1H-indazol-6-yl)-amide

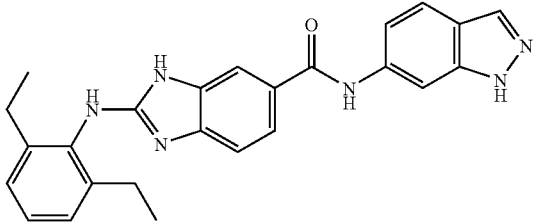

A solution of 1,3-diethyl-2-isothiocyanatobenzene (0.5 mmol) in 1:1 DMF/THF (2 mL) was reacted with 3,4-diamino-N-(1H-indazol-6-yl)-benzamide (0.5 mmol; see Example 25) according to general procedure B to yield 2-(2,6-diethylphenylamino)-3H-benzimidazole-5-carboxylic acid (1H-indazol-6-yl)-amide. MS: m/z 425 $(M+H)^+$.

Example 92

Synthesis 6-diisobutylamino-2-(2-trifluoromethylphenylamino)-3H-benzimidazole-5-carboxylic acid (1H-indazol-6-yl)-amide

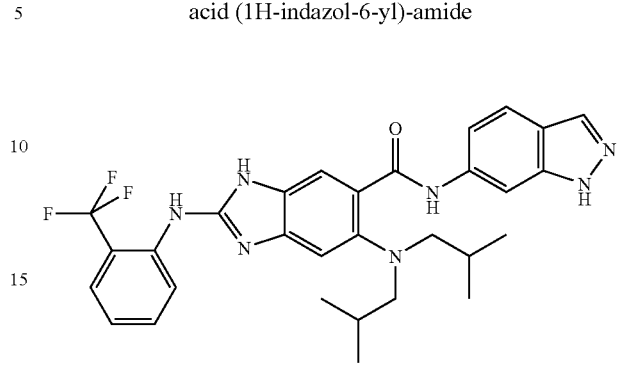

A solution 4-amino-2-chloro-N-(1H-indazol-6-yl)-5-nitrobenzamide (1 mmol; see Example 48) in NMP (2 mL) was added with diisobutylamine (0.5 mL), and the resulting mixture was subjected to microwave irradiation at 140° C. for 1 h. The reaction mixture was cooled to room temperature, diluted with water (20 mL). The solid formed was collected by filtration, washed with water, and dried in vacuo to provide 4-amino-2-diisobutylamino-N-(1H-indazol-6-yl)-5-nitrobenzamide.

The nitro compound (0.5 mmol) as above was reduced under hydrogenation conditions as described in general procedure F to afford 4,5-diamino-2-diisobutylamino-N-(1H-indazol-6-yl)benzamide.

The diamine (0.3 mmol) from above was reacted with 1-trifluoromethyl-2-isothiocyanatobenzene (0.3 mmol) followed by cyclization using EDC as described in general procedure B to obtain 6-diisobutylamino-2-(2-trifluoromethylphenylamino)-3H-benzimidazole-5-carboxylic acid (1H-indazol-6-yl)-amide. MS: m/z 564 $(M+H)^+$.

Example 93

Synthesis of 6-diethylamino-2-(3-methylpyridin-2-ylamino)-1H-benzimidazole-5-carboxylic acid (1H-indazol-6-yl)-amide

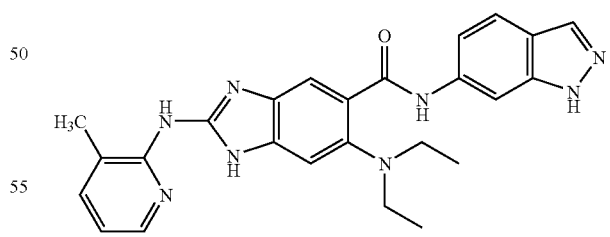

A solution 4-amino-2-chloro-N-(1H-indazol-6-yl)-5-nitrobenzamide (1 mmol; see Example 48) in NMP (2 mL) was added with diethylamine (1.0 mL), and the resulting mixture was subjected to microwave irradiation at 70° C. for 1 h. The reaction mixture was cooled to room temperature, diluted with water (20 mL). The solid formed was collected by filtration, washed with water, and dried in vacuo to provide 4-amino-2-diethylamino-N-(1H-indazol-6-yl)-5-nitrobenzamide.

The nitro compound (0.5 mmol) as above was reduced under hydrogenation conditions as described in general procedure F to afford 4,5-diamino-2-diethylamino-N-(1H-indazol-6-yl)benzamide.

The diamine (0.3 mmol) from above was reacted with 2-isothiocyanato-3-methylpyridine (0.3 mmol; prepared from 3-methylpyridin-2-ylamine following general procedure A) followed by cyclization using EDC as described in general procedure B to obtain 6-diethylamino-2-(3-methylpyridin-2-ylamino)-1H-benzimidazole-5-carboxylic acid (1H-indazol-6-yl)-amide. MS: m/z 455 (M+H)$^+$.

Following the procedure in Example 93, 4-amino-2-chloro-N-(1H-indazol-6-yl)-5-nitrobenzamide was utilized to synthesize the compounds listed in Table 7.

TABLE 7

| Ex. | Ar | X | MS (m/z) |
|---|---|---|---|
| 94 | 2-Trifluoromethylphenyl | 2,6-Dimethylmorpholin-4-yl | 550 |
| 95 | 2-Trifluoromethylphenyl | Diethylamino | 508 |
| 96 | 2-Trifluoromethylphenyl | (2-dimethylaminoethyl)methylamino | 537 |
| 97 | 2-Trifluoromethylphenyl | 4-Dimethylaminopiperidin-1-yl | 563 |
| 98 | 2-Trifluoromethylphenyl | Dipropylamino | 536 |
| 99 | 3-Methylpyridin-2-yl | Dipropylamino | 483 |
| 100 | 2-Trifluoromethylphenyl | Bis-(2-methoxyethyl)amino | 568 |
| 101 | 2-Trifluoromethylphenyl | 4-Hydroxypiperidin-1-yl | 536 |
| 102 | 2-Trifluoromethylphenyl | Ethyl-(2-methoxyethyl)amino | 538 |
| 103 | 3-Methylpyridin-2-yl | Bis-(2-methoxyethyl)amino | 515 |
| 104 | 3-Methylpyridin-2-yl | pyrrolidin-1-yl | 453 |
| 105 | 2-Trifluoromethylphenyl | pyrrolidin-1-yl | 506 |
| 106 | 2-Trifluoromethylphenyl | (2-Dimethylaminoethyl)ethylamino | 551 |
| 107 | 3-Methylpyridin-2-yl | 4-Hydroxypiperidin-1-yl | 483 |
| 108 | 3-Methylpyridin-2-yl | Ethyl-(2-methoxyethyl)amino | 485 |
| 109 | 2-Trifluoromethylphenyl | Ethylpropylamino | 522 |
| 110 | 3-Methylpyridin-2-yl | Ethylpropylamino | 469 |
| 111 | 2-Trifluoromethylphenyl | 4-Isopropylpiperazin-1-yl | 563 |
| 112 | 2-Trifluoromethylphenyl | Ethylmethylamino | 494 |
| 113 | 3-Methylpyridin-2-yl | Ethylmethylamino | 441 |
| 114 | 3-Methylpyridin-2-yl | 4-Isopropylpiperazin-1-yl | 510 |

Example 115

Synthesis of 2-(3-Chloropyridin-2-ylamino)-6-diethylamino-1H-benzoimidazole-5-carboxylic acid (1H-indazol-6-yl)-amide

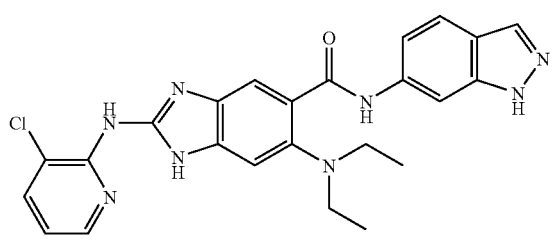

To a suspension of 2-chloro-4-fluoro-5-nitrobenzoic acid (5 mmol), oxalyl chloride (15 mmol) was added in dry DCM (5 mL) containing dry DMF (0.2 mL), and the mixture was stirred at 50° C. After the reaction was complete (~60 min), the solvent was removed in vacuo to afford acid chloride. Toluene (~1 mL) was added to the acid chloride, and the solvent was removed to dryness in vacuo to ensure complete removal of residual oxalyl chloride. The product, 4-chloro-2-fluoro-5-nitrobenzoyl chloride, was obtained as a light yellow solid.

The acid chloride (~5 mmol) obtained as above was dissolved in EtOAc (5 mL) and was added dropwise to a suspension of 6-aminoindazole (4.5 mmol) in EtOAc (15 mL) containing triethylamine (1 mL) at 0-5° C. The mixture was then allowed to warm to room temperature and stirred for 2-3 h. Most of the solvent was removed in vacuo and the residue was added with hexane. The solids were collected on a filter, washed twice with hexane/EtOAc (5:1) and thrice with water. The residue was dried in vacuo to afford the product, 2-chloro-4-fluoro-N-(1H-indazol-6-yl)-5-nitrobenzamide, as a yellow solid, which was used for further transformation without further purification. MS: m/z 335 (M+H)$^+$.

To a solution of 2-chloro-4-fluoro-N-(1H-indazol-6-yl)-5-nitrobenzamide (3 mmol) in dioxane (6 mL) was added concentrated aqueous NH$_4$OH (3 mL). The resulting mixture was heated at 60° C. for 2-3 h. The completed reaction afforded the product, 2-amino-4-fluoro-N-(1H-indazol-6-yl)-5-nitrobenzamide. To the crude reaction mixture was added diethylamine (45 mmol). The mixture then heated at 60° C. for 6 h. After the reaction was complete, the volatiles were removed in vacuo, and the residue was suspended in cold water. The solid was collected by filtration, washed with water, and dried in vacuo to provide 4-amino-2-diethylamino-N-(1H-indazol-6-yl)-5-nitrobenzamide.

The nitro compound (2 mmol) obtained as above was reduced under hydrogenation conditions as described in general procedure F to afford 4,5-diamino-2-diethylamino-N-(1H-indazol-6-yl)benzamide.

To a stirred solution of 2-amino-3-chloropyridine (2 mmol) in CHCl$_3$ (5 mL) was added 0.7 M aqueous sodium bicarbonate solution at 0° C. Thiophosgene (2.2 mmol) was added dropwise at 0° C., and the contents were allowed to warm to RT gradually over a period of 2 h. The reaction mixture was diluted with DCM (20 mL), and the layers were separated. The organic layer washed with water (2×10 mL), followed with brine (10 mL) and dried over anhydrous Na$_2$SO$_4$. The volatiles were removed in vacuo, and the product, 3-chloro-2-isothiocyanatopyridine, was used without any purification.

The diamine (0.3 mmol) from above was reacted with 3-chloro-2-isothiocyanatopyridine (0.3 mmol) followed by cyclization in situ using EDC as described in general procedure B to obtain 2-(3-chloropyridin-2-ylamino)-6-diethylamino-1H-benzoimidazole-5-carboxylic acid(1H-indazol-6-yl)-amide. MS: m/z 475 (M+H)$^+$.

Following the procedure in Example 115, 4,5-diamino-2-diethylamino-N-(1H-indazol-6-yl)benzamide was utilized to synthesize the compounds listed in Table 8.

TABLE 8

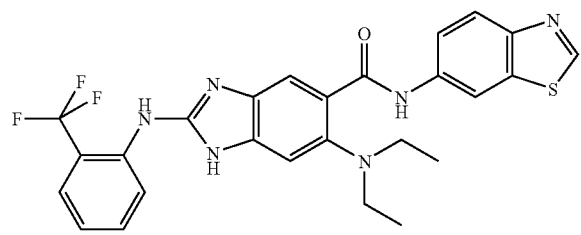

| Ex. | Ar | MS (m/z) |
|---|---|---|
| 116 | 3-Trifluoromethylpyridin-2-yl | 509 |
| 117 | 1-Cyclopentyl-1H-imidazol-2-yl | 498 |
| 118 | Cyclohexyl | 446 |
| 119 | Cyclopentyl | 432 |
| 120 | Bicyclo[2.2.1]hept-2-yl | 458 |
| 121 | Isopropyl | 406 |
| 122 | 3-Ethyl-6-methylpyridin-2-yl | 483 |
| 123 | 2,5-Difluorophenyl | 476 |
| 124 | 3,5-Difluorophenyl | 476 |
| 125 | 2-Chloro-5-trifluoromethylphenyl | 542 |
| 126 | 2-Trifluoromethoxyphenyl | 524 |
| 127 | 3-Methoxycarbonylphenyl | 498 |
| 128 | 2-Isopropylphenyl | 482 |
| 129 | 4-Chlorophenyl | 474 |
| 130 | 2,4-Dichlorophenyl | 508 |
| 131 | 2,6-Difluorophenyl | 476 |
| 132 | 2-Methoxyphenyl | 470 |

Example 133

Synthesis of 6-diethylamino-2-(2-trifluoromethylphenyl amino)-1H-benzoimidazole-5-carboxylic acid benzothiazol-6-ylamide

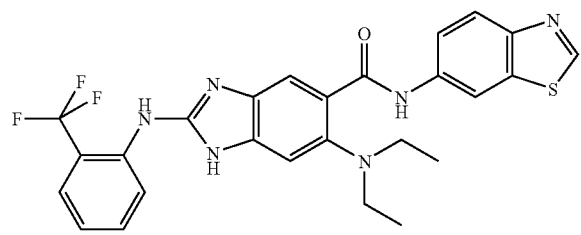

6-aminobenzothioazole (4.5 mmol) was reacted with 4-chloro-2-fluoro-5-nitrobenzoyl chloride (5 mmol) employing the conditions described in Example 115. The reaction mixture was diluted with EtOAc (40 mL) and washed with water (2×40 mL) and brine (40 mL) and dried over anhydrous $Na_2SO_4$. Removal of organics afforded the product, N-benzothiazol-6-yl-2-chloro-4-fluoro-5-nitrobenzamide as a yellow solid. MS: m/z 352 $(M+H)^+$.

A solution of the aforementioned amide (3 mmol) in dioxane was reacted with aqueous $NH_4OH$ and subsequently with diethylamine using the one-pot procedure described for Example 115 to yield 4-amino-N-benzothiazol-6-yl-2-diethylamino-5-nitrobenzamide as a yellow solid.

The nitro compound (2 mmol) obtained as above was reduced under hydrogenation conditions as described in general procedure F to afford 4,5-diamino-N-benzothiazol-6-yl-2-diethylaminobenzamide.

The diamine (0.3 mmol) from above was reacted with 1-isothiocyanato-2-trifluoromethylbenzene (0.3 mmol) followed by cyclization in situ using EDC as described in general procedure B to obtain 6-diethylamino-2-(2-trifluoromethylphenylamino)-1H-benzoimidazole-5-carboxylic acid benzothiazol-6-ylamide. MS: m/z 525 $(M+H)^+$.

Following the procedure in Example 133, 4,5-diamino-N-benzothiazol-6-yl-2-diethylaminobenzamide was utilized to synthesize the compounds listed in Table 9.

TABLE 9

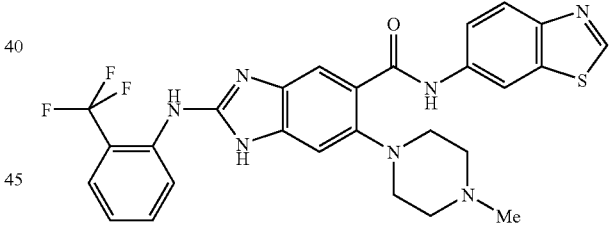

| Ex. | Ar | MS (m/z) |
|---|---|---|
| 134 | Bicyclo[2.2.1]hept-2-yl | 475 |
| 135 | Isopropyl | 423 |
| 136 | 2,5-Difluorophenyl | 493 |
| 137 | 3,5-Difluorophenyl | 493 |
| 138 | 2,4-Dichlorophenyl | 526 |
| 139 | 2-Trifluoromethoxyphenyl | 541 |
| 140 | 2-Isopropylphenyl | 499 |

Example 141

Synthesis of 6-(4-methyl-piperazin-1-yl)-2-(2-trifluoromethyl-phenylamino)-1H-benzoimidazole-5-carboxylic acid benzothiazol-6-ylamide

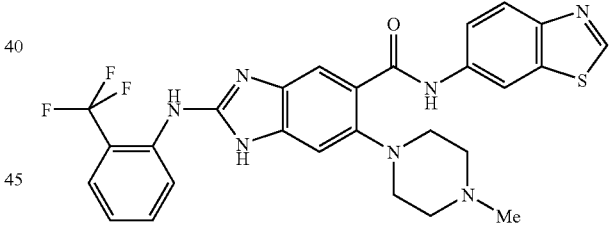

A solution of N-benzothiazol-6-yl-2-chloro-4-fluoro-5-nitrobenzamide (2 mmol) in dioxane (4 mL) was reacted with aqueous $NH_4OH$ using the conditions described in Example 115. After the formation of 4-amino-N-benzothiazol-6-yl-2-chloro-5-nitrobenzamide was complete, the reaction mixture was charged with N-methylpiperazine (12 mmol). The contents were heated at reflux for 10 h, and the reaction mixture was cooled to RT. The contents were poured onto ice cold water with vigorous stirring. The solid formed was collected by filtration, washed with water, and dried in vacuo to provide the product, 4-amino-N-benzothiazol-6-yl-2-(4-methyl-piperazin-1-yl)-5-nitrobenzamide as a yellow solid.

The nitro compound (2 mmol) obtained as above, was reduced under hydrogenation conditions as described in general procedure F to afford 4,5-Diamino-N-benzothiazol-6-yl-2-(4-methyl-piperazin-1-yl)-benzamide.

The diamine (0.3 mmol) from above was reacted with 1-isothiocyanato-2-trifluoromethylbenzene (0.3 mmol) followed by cyclization in situ using EDC as described in general procedure B to obtain 6-(4-methyl-piperazin-1-yl)-2-(2-trifluoromethyl-phenylamino)-1H-benzoimidazole-5-carboxylic acid benzothiazol-6-ylamide. MS: m/z 552 (M+H)⁺.

Following the procedure in Example 141, 4-amino-N-benzothiazol-6-yl-2-chloro-5-nitrobenzamide was utilized to synthesize the compounds listed in Table 10.

TABLE 10

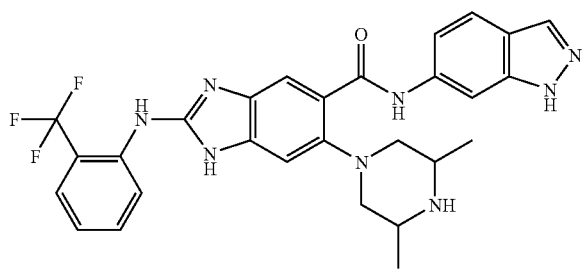

| Ex. | Ar | R | MS (m/z) |
|---|---|---|---|
| 142 | 3-Methylpyridin-2-yl | 4-methylpiperazin-1-yl | 499 |
| 143 | 2-Trifluoromethylphenyl | Morpholino-4-yl | 539 |
| 144 | 3-Methylpyridin-2-yl | Morpholino-4-yl | 486 |

Example 145

Synthesis of 6-(3,5-dimethylpiperazin-1-yl)-2-(2-trifluoromethyl-phenylamino)-1H-benzoimidazole-5-carboxylic acid (1H-indazol-6-yl)-amide A solution of 2-chloro-4-fluoro-N-(1H-indazol-6-yl)-5-nitrobenzamide (1 mmol) in dioxane (2 mL) was reacted with aqueous NH₄OH using the conditions described in Example 115. After the formation of 2-amino-4-fluoro-N-(1H-indazol-6-yl)-5-nitrobenzamide was complete, the reaction mixture was charged with 2,6-dimethylpiperazine (6 mmol). The contents were heated at reflux for 10 h, and the reaction mixture was cooled to RT. The contents were poured onto ice cold water with vigorous stirring. The solid formed was collected by filtration, washed with water, and dried in vacuo to provide the product, 4-amino-2-(3,5-dimethyl-piperazin-1-yl)-N-(1H-indazol-6-yl)-5-nitrobenzamide as a yellow solid.

The nitro compound (0.6 mmol) obtained as above, was reduced under hydrogenation conditions as described in general procedure F to afford 4,5-Diamino-2-(3,5-dimethylpiperazin-1-yl)-N-(1H-indazol-6-yl)-benzamide.

The diamine (0.3 mmol) from above was reacted with 1-isothiocyanato-2-trifluoromethylbenzene (0.3 mmol) followed by cyclization in situ using EDC as described in general procedure B to obtain 6-(3,5-dimethylpiperazin-1-yl)-2-(2-trifluoromethyl-phenylamino)-1H-benzoimidazole-5-carboxylic acid (1H-indazol-6-yl)-amide. MS: m/z 549 (M+H)⁺.

Following the procedure in Example 145, 2-amino-4-fluoro-N-(1H-indazol-6-yl)-5-nitrobenzamide was utilized to synthesize the compounds listed in Table 11.

TABLE 11

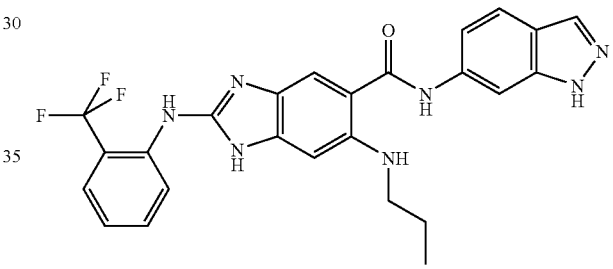

| Ex. | Ar | R | MS (m/z) |
|---|---|---|---|
| 146 | 2-Trifluoromethylphenyl | 2-methoxyethylamino | 510 |
| 147 | 3-Methylpyridin-2-yl | 2-methoxyethylamino | 457 |
| 148 | 2-Trifluoromethylbenzyl | 4-methylpiperazin-1-yl | 549 |
| 149 | Benzyl | 4-methylpiperazin-1-yl | 481 |
| 150 | Cyclohexylmethyl | 4-methylpiperazin-1-yl | 487 |
| 151 | Cyclopentyl | 4-methylpiperazin-1-yl | 459 |
| 152 | (1S,2S,4R)-Bicyclo[2.2.1]hept-2-yl | 4-methylpiperazin-1-yl | 485 |
| 153 | Adamantan-1-yl | 4-methylpiperazin-1-yl | 525 |

Example 154

Synthesis of 6-propylamino-2-(2-trifluoromethylphenylamino)-1H-benzoimidazole-5-carboxylic acid (1H-indazol-6-yl-amide)

A solution of 2-chloro-4-fluoro-N-(1H-indazol-6-yl)-5-nitrobenzamide (2 mmol) in dioxane (4 mL) was reacted with aqueous NH₄OH using the conditions described in Example 115. After the formation of 2-amino-4-fluoro-N-(1H-indazol-6-yl)-5-nitrobenzamide was complete, the volatiles were removed in vacuo. The residue obtained was suspended in cold water with stirring. The solid formed was collected by filtration, washed with water, and dried in vacuo to provide the product, 4-amino-2-chloro-N-(1H-indazol-6-yl)-5-nitrobenzamide as a yellow solid.

A solution product obtained as above (0.5 mmol) in NMP (1 mL) was charged with propylamine (0.5 mL). The contents were subjected to microwave irradiation at 80° C. for 60 min. The reaction mixture was cooled to room temperature, diluted with water (10 mL). The solid formed was collected by filtration, washed with water, and dried in vacuo to provide 4-amino-N-(1H-indazol-6-yl)-5-nitro-2-propylaminobenzamide.

The nitro compound (0.4 mmol) obtained as above was reduced under hydrogenation conditions as described in general procedure F to afford 4,5-diamino-N-(1H-indazol-6-yl)-2-propylamino-benzamide.

The diamine (0.3 mmol) from above was reacted with 1-isothiocyanato-2-trifluoromethylbenzene (0.3 mmol) followed by cyclization in situ using EDC as described in general procedure B to 6-propylamino-2-(2-trifluoromethylphenylamino)-1H-benzoimidazole-5-carboxylic acid (1H-indazol-6-yl)amide. MS: m/z 494 (M+H)⁺.

Example 155

Synthesis of {1-[6-(1H-Indazol-6-ylcarbamoyl)-2-(2-trifluoromethyl-phenylamino)-3H-benzoimidazol-5-yl]-piperidin-4-yl}-carbamic acid tert-butyl ester

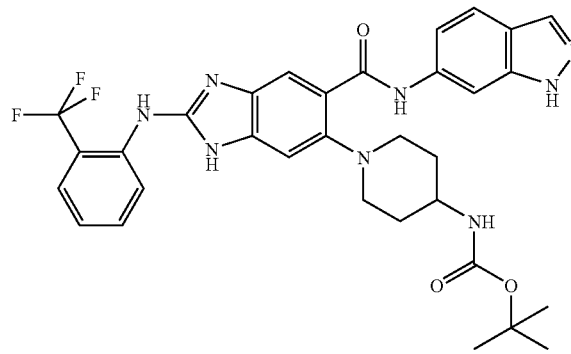

A solution 4-amino-2-chloro-N-(1H-indazol-6-yl)-5-nitrobenzamide (1 mmol; see Example 154) in NMP (2 mL) was added piperidin-4-yl-carbamic acid tert-butyl ester (4 mmol). The resulting mixture was heated at 100° C. for 10 h. The reaction mixture was cooled to room temperature, and diluted with water (20 mL). The solid formed was collected by filtration, washed with water, and dried in vacuo. The crude product was purified on a silica gel column chromatography using EtOAc/hexane as eluent to provide {1-[5-Amino-2-(1H-indazol-6-ylcarbamoyl)-4-nitro-phenyl]-piperidin-4-yl}-carbamic acid tert-butyl ester as a light yellow solid.

The nitro compound (0.5 mmol) as above was reduced under hydrogenation conditions as described in general procedure F to afford {1-[4,5-diamino-2-(1H-indazol-6-ylcarbamoyl)-phenyl]-piperidin-4-yl}-carbamic acid tert-butyl ester.

The diamine (0.3 mmol) from above was reacted with 1-isothiocyanato-2-trifluoromethylbenzene (0.3 mmol) followed by cyclization in situ using EDC as described in general procedure B to provide {1-[6-(1H-Indazol-6-ylcarbamoyl)-2-(2-trifluoromethyl-phenylamino)-3H-benzoimidazol-5-yl]-piperidin-4-yl}-carbamic acid tert-butyl ester. MS: m/z 635 (M+H)$^+$.

Example 156

Synthesis of 6-(4-Aminopiperidin-1-yl)-2-(2-trifluoromethylphenylamino)-1H-benzoimidazole-5-carboxylic acid (1H-indazol-6-yl)-amide trihydrochloride

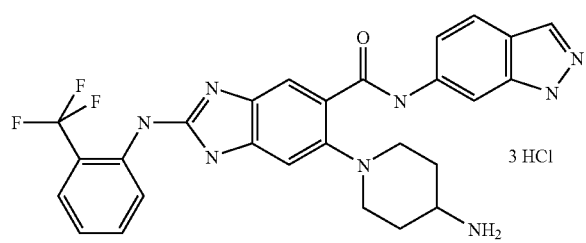

To a solution of {1-[6-(1H-Indazol-6-ylcarbamoyl)-2-(2-trifluoromethyl-phenylamino)-3H-benzoimidazol-5-yl]-piperidin-4-yl}-carbamic acid tert-butyl ester (0.25 mmol; see Example 155) in methanol (1 mL) was 4M HCl in dioxane (0.5 mL) added. The resulting mixture was stirred at room temperature for 5-6 h. The volatiles were removed in vacuo, and the residue obtained was suspended in ether. The solid obtained was collected by filtration, washed with ether and dried in vacuo to afford 6-(4-Amino-piperidin-1-yl)-2-(2-trifluoromethyl-phenylamino)-1H-benzoimidazole-5-carboxylic acid (1H-indazol-6-yl)-amide as a hydrochloride salt. MS: m/z 535 (M+H)$^+$.

Example 157

Synthesis of {1-[6-(1H-Indazol-6-ylcarbamoyl)-2-(3-methylpyridin-2-ylamino)-3H-benzoimidazol-5-yl]-piperidin-4-yl}-carbamic acid tert-butyl ester

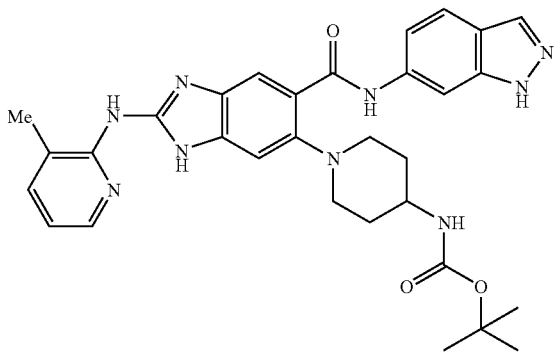

A solution of {1-[4,5-diamino-2-(1H-indazol-6-ylcarbamoyl)-phenyl]-piperidin-4-yl}-carbamic acid tert-butyl ester (0.3 mmol; see Example 155) in DMF (1 mL) was reacted with 1-isothiocyanato-2-trifluoromethylbenzene (0.3 mmol) followed by cyclization in situ using EDC as described in general procedure B to provide {{1-[6-(1H-Indazol-6-ylcarbamoyl)-2-(3-methylpyridin-2-ylamino)-3H-benzoimidazol-5-yl]-piperidin-4-yl}-carbamic acid tert-butyl ester. MS: m/z 582 (M+H)$^+$.

Example 158

Synthesis of 6-(4-Aminopiperidin-1-yl)-2-(3-methylpyridin-2-ylamino)-1H-benzimidazole-5-carboxylic acid (1H-indazol-6-yl)-amide trihydrochloride

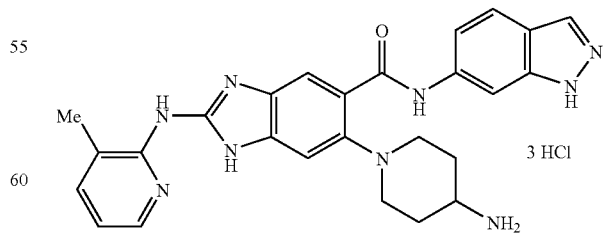

The product from Example 157 was treated with 4M HCl in dioxane employing the procedure described for Example 156 to afford 6-(4-Aminopiperidin-1-yl)-2-(3-methylpyridin-2- ylamino)-1H-benzimidazole-5-carboxylic acid (1H-indazol-6-yl)-amide as a hydrochloride salt. MS: m/z 521 (M+H)$^+$.

Example 159

Synthesis of [5-(1H-Indazol-6-ylethynyl)-1H-benzoimidazol-2-yl]-(2-trifluoromethyl-phenyl)-amine

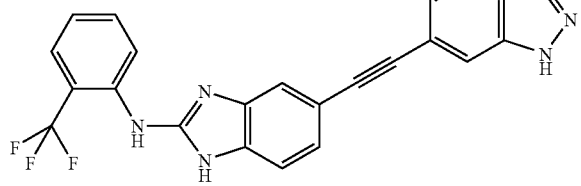

A mixture of 4-bromo-2-nitrophenylamine (2.17 g, 10 mmol), ethynyltrimethylsilane (2.11 mL, 98%, 15 mmol), dichlorobis(triphenylphosphine)palladium(II) (211 mg, 0.3 mmol) and copper(I) chloride (66.5 mg, 0.35 mmol) in THF (10 mL) and triethyl amine (10 mL) was stirred at room temperature for 3 days. The product, 2-nitro-4-trimethylsilanylethynylphenylamine was purified by silica gel column chromatography. LC-MS m/z: 235 (M+1)$^+$.

A mixture of the silyl intermediate from previous above potassium carbonate (2.76 g, 20 mmol) and methanol (30 mL) was stirred for two days. Purification by silica gel column chromatography gave 4-ethynyl-2-nitrophenylamine as red solid (1.306 g, 8.05 mmol, yield 81% for 2 steps). LC-MS m/z: 163 (M+1)$^+$.

A mixture of 4-ethynyl-2-nitro-phenylamine (1.306 g, 8.05 mmol), 6-iodo-1H-indazole (1.965 g, 8.05 mmol), dichlorobis(triphenylphosphine)palladium(II) (122 mg, 0.24 mmol) and copper(I) chloride (54.4 mg, 0.28 mmol) in THF (8 mL) and triethyl amine (8 mL) was stirred at room temperature overnight. Purification by column chromatography on silica gel gave 4-(1H-indazol-6-ylethynyl)-2-nitrophenylamine as red solid (777 mg, 2.79 mmol, yield 35%). LC-MS m/z: 279 (M+1)$^+$.

A mixture of the nitro compound from above (774 mg, 2.78 mmol), iron powder (1.61 g, 97%, 28 mmol) and ammonium chloride (2.25 g, 42 mmol) in ethanol (1.5 mL) and water (1.5 mL) was refluxed for 6 h. Purification by column chromatography on silica gel gave 4-(1H-indazol-6-ylethynyl)-benzene-1,2-diamine as brown solid (284 mg, 1.14 mmol, yield 41%). LC-MS m/z: 249 (M+1)$^+$.

The diamine (0.3 mmol) from above was reacted with 1-isothiocyanato-2-trifluoromethylbenzene (0.3 mmol) followed by cyclization in situ using EDC as described in general procedure B to provide [5-(1H-Indazol-6-ylethynyl)-1H-benzoimidazol-2-yl]-(2-trifluoromethylphenyl)-amine as yellow solid (178 mg, 0.426 mmol, yield 66%). LC-MS m/z: 418 (M+1)$^+$.

Example 160

Synthesis of 6-dimethylamino-2-(2-trifluoromethylphenylamino)-1H-benzoimidazole-5-carboxylic acid (1H-indazol-6-yl)-amide

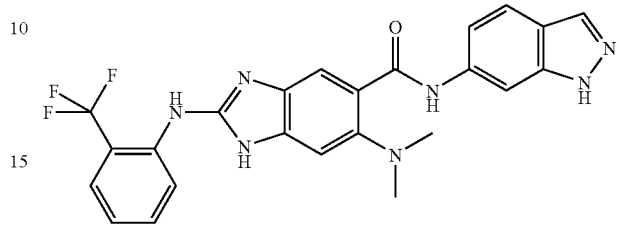

A solution 4-amino-2-chloro-N-(1H-indazol-6-yl)-5-nitrobenzamide (1 mmol; see Example 157) in DMF (1 mL) was added with of 10% aqueous K$_2$CO$_3$ solution (0.25 mL). The mixture was then subjected to microwave at 80° C. for 60 min. The contents were cooled to RT and poured into ice-cold water (20 L). The solid formed was collected by filtration, washed with water, and dried in vacuo to provide 4-amino-2-dimethylamino-N-(1H-indazol-6-yl)-5-nitrobenzamide.

The nitro compound (0.5 mmol) as above was reduced under hydrogenation conditions as described in general procedure F to afford 4,5-diamino-2-dimethylamino-N-(1H-indazol-6-yl)benzamide.

The diamine (0.3 mmol) from above was reacted with 1-isothiocyanato-2-trifluoromethylbenzene (0.3 mmol) followed by cyclization in situ using EDC as described in general procedure B to provide 6-dimethylamino-2-(2-trifluoromethylphenylamino)-1H-benzoimidazole-5-carboxylic acid (1H-indazol-6-yl)-amide. MS: m/z 480 (M+H)$^+$.

Example 161

Synthesis of 6-dimethylamino-2-(3-methylpyridin-2-ylamino)-1H-benzoimidazole-5-carboxylic acid (1H-indazol-6-yl)-amide

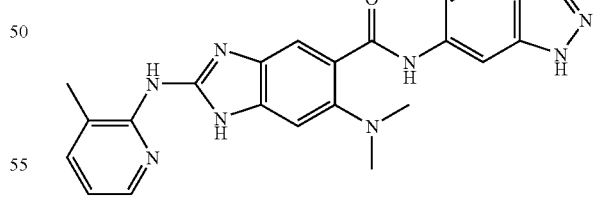

4,5-diamino-2-dimethylamino-N-(1H-indazol-6-yl)benzamide (see Example 160; 0.3 mmol) was reacted with 2-isothiocyanato-3-methylpyridine (0.3 mmol; prepared from 2-amino-3-methylpyridine and thiophosgene employing procedure described in Example 115) followed by cyclization in situ using EDC as described in general procedure B to provide 6-dimethylamino-2-(3-methylpyridin-2-ylamino)-1H-benzoimidazole-5-carboxylic acid (1H-indazol-6-yl)-amide. MS: m/z 427 (M+H)$^+$.

Example 162

Synthesis of 6-(4-methylpiperazin-1-yl)-2-(2-trifluoromethyl-phenylamino)-1H-benzoimidazole-5-carboxylic acid benzothiazol-5-ylamide

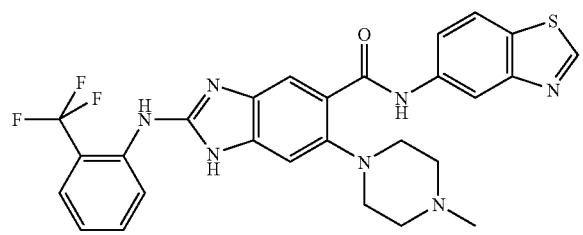

5-aminobenzothioazole (4.5 mmol) was reacted with 4-chloro-2-fluoro-5-nitrobenzoyl chloride (5 mmol) employing the conditions described in Example 133. The product, N-benzothiazol-5-yl-2-chloro-4-fluoro-5-nitrobenzamide, was also isolated similar to Example 133.

A solution of the amide from above (2 mmol) in dioxane (4 mL) was reacted with aqueous NH₄OH using the conditions described in Example 115. After the formation of 4-amino-N-benzothiazol-5-yl-2-chloro-5-nitrobenzamide was complete, the reaction mixture was charged with N-methylpiperazine (12 mmol). The contents were heated at reflux for 10 h, and the reaction mixture was cooled to RT. The contents were poured onto ice cold water with vigorous stirring. The solid formed was collected by filtration, washed with water, and dried in vacuo to provide the product, 4-amino-N-benzothiazol-5-yl-2-(4-methyl-piperazin-1-yl)-5-nitrobenzamide as a yellow solid.

The nitro compound (2 mmol) obtained as above, was reduced under hydrogenation conditions as described in general procedure F to afford 4,5-diamino-N-benzothiazol-5-yl-2-(4-methylpiperazin-1-yl)-benzamide.

The diamine (0.3 mmol) from above was reacted with 1-isothiocyanato-2-trifluoromethylbenzene (0.3 mmol) followed by cyclization in situ using EDC as described in general procedure B to obtain 6-(4-methylpiperazin-1-yl)-2-(2-trifluoromethyl-phenylamino)-1H-benzoimidazole-5-carboxylic acid benzothiazol-5-ylamide. MS: m/z 552 (M+H)⁺.

Example 163

4-[6-(Benzothiazol-6-ylcarbamoyl)-2-(2-trifluoromethyl-phenylamino)-3H-benzoimidazol-5-yl]piperazine-1-carboxylic acid tert-butyl ester

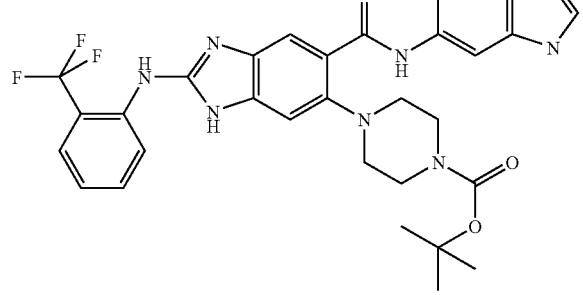

A solution of 4-amino-N-benzothiazol-6-yl-2-chloro-5-nitrobenzamide (2 mmol; prepared as in Example 141) in dioxane (5 mL) was charged with piperazine (10 mmol). The contents were heated at reflux for 10 h and the reaction mixture was cooled to RT. The contents were poured onto ice cold water with vigorous stirring. The solid formed was collected by filtration, washed with water, and dried in vacuo to provide the product, 4-amino-N-benzothiazol-6-yl-5-nitro-2-piperazin-1-yl-benzamide as a yellow solid.

The amide (1 mmol) from above was dissolved in THF (3 mL) and was treated with BOC anhydride (1.2 mmol) and stirred for 2 h at RT. The solvent was removed to dryness, and the residue obtained was suspended in 10% EtOAc/hexane (10 mL) with stirring. The solid formed was collected by filtration, washed with 10% EtOAc/hexane and dried in vacuo to afford 4-[5-amino-2-(benzothiazol-6-ylcarbamoyl)-4-nitrophenyl]piperazine-1-carboxylic acid tert-butyl ester.

The nitro compound (0.8 mmol) as above was reduced under hydrogenation conditions as described in general procedure F to afford 4-[4,5-diamino-2-(benzothiazol-6-ylcarbamoyl)-phenyl]piperazine-1-carboxylic acid tert-butyl ester.

The diamine (0.3 mmol) from above was reacted with 1-isothiocyanato-2-trifluoromethylbenzene (0.3 mmol) followed by cyclization in situ using EDC as described in general procedure B to provide 4-[6-(Benzothiazol-6-ylcarbamoyl)-2-(2-trifluoromethylphenylamino)-3H-benzoimidazol-5-yl]piperazine-1-carboxylic acid tert-butyl ester. MS: m/z 638 (M+H)⁺.

Example 164

Synthesis of afford 6-piperazin-1-yl-2-(2-trifluoromethylphenylamino)-1H-benzoimidazole-5-carboxylic acid benzothiazol-6-ylamide trihydro chloride

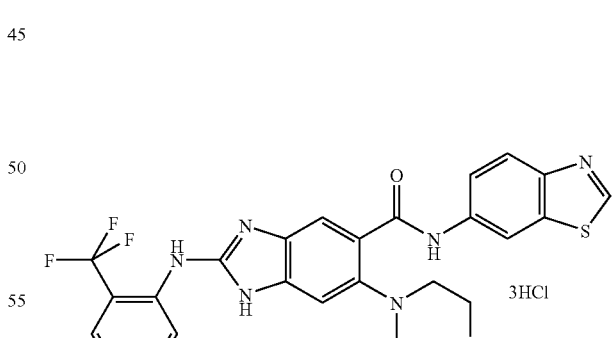

The product from Example 163 was treated with 4M HCl in dioxane employing the procedure described for Example 156 to afford 6-piperazin-1-yl-2-(2-trifluoromethylphenylamino)-1H-benzoimidazole-5-carboxylic acid benzothiazol-6-ylamide as a hydrochloride salt. MS: m/z 538 (M+H)⁺.

Example 165

Synthesis of 4-[6-(Benzothiazol-6-ylcarbamoyl)-2-(3-methylpyridin-2-ylamino)-3H-benzoimidazol-5-yl]piperazine-1-carboxylic acid tert-butyl ester

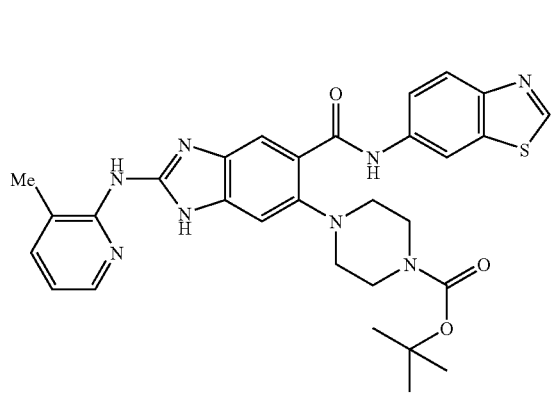

4-[4,5-diamino-2-(benzothiazol-6-ylcarbamoyl)-phenyl]piperazine-1-carboxylic acid tert-butyl ester (see Example 163; 0.3 mmol) was reacted with 2-isothiocyanato-3-methylpyridine (0.3 mmol; prepared from 2-amino-3-methylpyridine and thiophosgene employing procedure described in Example 115) followed by cyclization in situ using EDC as described in general procedure B to provide 4-[6-(Benzothiazol-6-ylcarbamoyl)-2-(3-methyl-pyridin-2-ylamino)-3H-benzoimidazol-5-yl]piperazine-1-carboxylic acid tert-butyl ester. MS: m/z 585 (M+H)$^+$.

Example 166

Synthesis of 2-(3-Methyl-pyridin-2-ylamino)-6-piperazin-1-yl-1H-benzoimidazole-5-carboxylic acid benzothiazol-6-ylamide as a hydrochloride salt

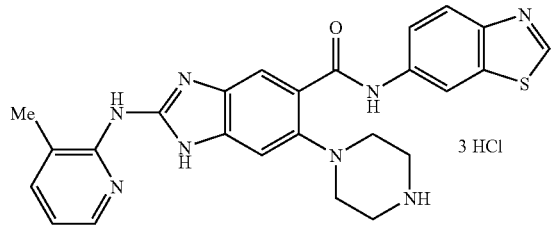

The product from Example 165 was treated with 4M HCl in dioxane employing the procedure described for Example 156 to afford 2-(3-Methyl-pyridin-2-ylamino)-6-piperazin-1-yl-1H-benzoimidazole-5-carboxylic acid benzothiazol-6-ylamide as a hydrochloride salt. MS: m/z 485 (M+H)$^+$.

Example 167

Synthesis of 2-(2-trifluoromethyl-phenylamino)-1H-benzoimidazole-5-carboxylic acid benzothiazol-6-ylamide

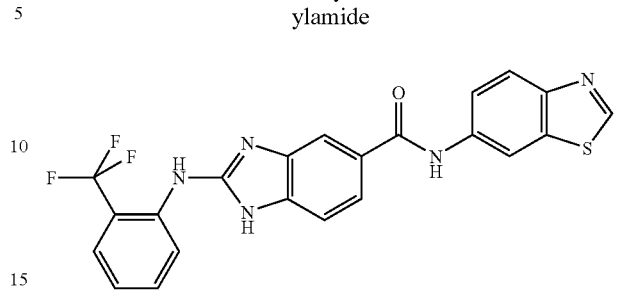

A solution of 3,4-diaminobenzoic acid (3 mmol) in DMF (10 mL) was charged with 1-isothiocyanato-2-trifluoromethylbenzene (3.3 mmol) and the resulting solution was stirred at RT for 4 h. After thiourea formation was complete, solid $K_2CO_3$ (10 mmol) was added to the reaction mixture, and the mixture was heated at 90° C. for 10 h. The reaction mixture was cooled to RT and acidified with 10% aqueous HCl to pH 7. The contents were poured onto ice cold water (30 mL) with vigorous stirring. The solid formed was collected by filtration, washed with water, and dried in vacuo to provide the product, 2-(2-trifluoromethylphenylamino)-1H-benzoimidazole-5-carboxylic acid as a yellow solid.

The carboxylic acid obtained as above (0.25 mmol) was coupled with 6-aminobenzothiazole (0.25 mmol) using HBTU employing general procedure D. The product, 2-(2-Trifluoromethylphenylamino)-1H-benzoimidazole-5-carboxylic acid benzothiazol-6-ylamide, was obtained as a light brown solid after purification by silica gel chromatography using DCM/methanol as eluent. MS: m/z 454 (M+H)$^+$.

Example 168

Synthesis of 6-piperazin-1-yl-2-(2-trifluoromethyl-phenylamino)-1H-benzoimidazole-5-carboxylic acid (5-methyl-1H-indazol-6-yl)amide

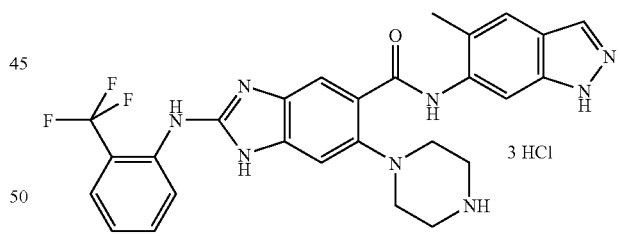

To a mixture of 2,4-dimethylaniline (10 mmol) in 5 mL of conc. $H_2SO_4$, fuming $HNO_3$ (90%; 0.6 mL) was added dropwise at 0° C. The resulting mixture was stirred for 12 h at RT and then slowly poured into ice. The solid was collected by filtration and dried to yield 2,4-dimethyl-5-nitroaniline as a yellow solid.

A solution of nitroaniline (5 mmol) obtained as above in HOAc (5 mL) at RT was added with iso-amyl nitrite (6 mmol) dropwise. The resulting mixture was stirred at RT for 14 h and then slowly poured on to cold saturated aqueous $NaHCO_3$ solution (15 mL). The contents were extracted with ethyl acetate (3×20 mL), and the combined organics washed with 5% aqueous $Na_2CO_3$ solution (30 mL). The volatiles were removed in vacuo to give 6-nitro-5-methylindazole as a brown solid.

The nitro compound (2 mmol) obtained as above was reduced under hydrogenation conditions as described in general procedure F to afford 6-amino-5-methylindazole as a brown solid.

The aminoindazole from above (1.5 mmol) was reacted with 4-chloro-2-fluoro-5-nitrobenzoyl chloride (1.5 mmol) employing the conditions described in Example 115. The product, 2-chloro-4-fluoro-N-(5-methyl-1H-indazol-6-yl)-5-nitrobenzamide, was also isolated similar to Example 115.

A solution of the amide from above (1 mmol) in dioxane (2 mL) was reacted with aqueous NH$_4$OH using the conditions described in Example 115. After the formation of 4-amino-2-chloro-N-(5-methyl-1H-indazol-6-yl)-5-nitrobenzamide was complete, charged with piperazine (5 mmol). The contents were heated at reflux for 10 h and the reaction mixture was cooled to RT. The contents were poured onto ice cold water with vigorous stirring. The solid formed was collected by filtration, washed with water, and dried in vacuo to provide the product, 4-amino-N-(5-methyl-1H-indazol-6-yl)-5-nitro-2-piperazin-1-yl-benzamide as a yellow solid.

The product from above (0.6 mol) was treated with BOC anhydride employing the procedure described for Example 163.

The nitro aniline from above (0.5 mmol) was reduced under hydrogenation conditions as described in general procedure F to afford 4-[4,5-diamino-2-(5-methyl-1H-indazol-6-ylcarbamoyl)-phenyl]piperazine-1-carboxylic acid tert-butyl ester.

The diamine (0.3 mmol) from above was reacted with 1-isothiocyanato-2-trifluoromethylbenzene (0.3 mmol) followed by cyclization in situ using EDC as described in general procedure B to provide 4-[6-(5-Methyl-1H-indazol-6-ylcarbamoyl)-2-(2-trifluoromethyl-phenylamino)-3H-benzoimidazol-5-yl]piperazine-1-carboxylic acid tert-butyl ester. MS: m/z 635 (M+H)$^+$.

The product from above was treated with 4M HCl in dioxane employing the procedure described for Example 156 to afford 6-piperazin-1-yl-2-(2-trifluoromethyl-phenylamino)-1H-benzoimidazole-5-carboxylic acid (5-methyl-1H-indazol-6-yl)amide as a hydrochloride salt. MS: m/z 535 (M+H)$^+$.

Example 169

Synthesis of 4-[2-((1S,2S,4R)-Bicyclo[2.2.1]hept-2-ylamino)-6-(1H-indazol-6-ylcarbamoyl)-3H-benzoimidazol-5-yl]-piperazine-1-carboxylic acid tert-butyl ester

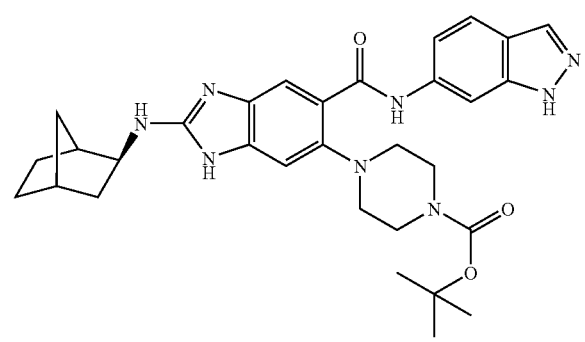

A solution 4-amino-2-chloro-N-(1H-indazol-6-yl)-5-nitrobenzamide (1 mmol; see Example 154) was reacted with piperazine following the procedure described in Example 163 to afford 4-amino-N-(1H-indazol-6-yl)-5-nitro-2-piperazin-1-ylbenzamide. The product thus obtained was treated with BOC anhydride as in Example 163 to obtain 4-[5-amino-2-(1H-indazol-6-ylcarbamoyl)-4-nitro-phenyl]-piperazine-1-carboxylic acid tert-butyl ester.

The nitro compound (0.6 mmol) as above was reduced under hydrogenation conditions as described in general procedure F to 4-[4,5-diamino-2-(1H-indazol-6-ylcarbamoyl)-phenyl]piperazine-1-carboxylic acid tert-butyl ester.

The diamine (0.3 mmol) from above was reacted with (S)-2-Isothiocyanato-bicyclo[2.2.1]heptane (0.3 mmol) followed by cyclization in situ using EDC as described in general procedure B to provide 4-[2-((1S,2S,4R)-Bicyclo[2.2.1]hept-2-ylamino)-6-(1H-indazol-6-ylcarbamoyl)-3H-benzoimidazol-5-yl]-piperazine-1-carboxylic acid tert-butyl ester. MS: m/z 571 (M+H)$^+$.

Example 170

Synthesis of 2-((1S,2S,4R)-Bicyclo[2.2.1]hept-2-ylamino)-6-piperazin-1-yl-1H-benzoimidazole-5-carboxylic acid (1H-indazol-6-yl)amide trihydrochloride

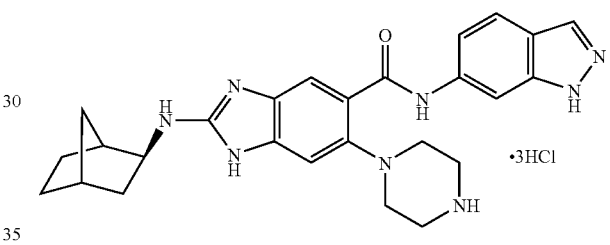

The product from Example 169 was treated with 4M HCl in dioxane employing the procedure described for Example 156 to afford 2-((1S,2S,4R)-bicyclo[2.2.1]hept-2-ylamino)-6-piperazin-1-yl-1H-benzoimidazole-5-carboxylic acid (1H-indazol-6-yl)amide as a hydrochloride salt. MS: m/z 471 (M+H)$^+$.

Example 171

Synthesis of 6-Chloro-2-(2-trifluoromethylphenylamino)-1H-benzoimidazole-5-carboxylic acid (1H-indazol-6-yl)amide

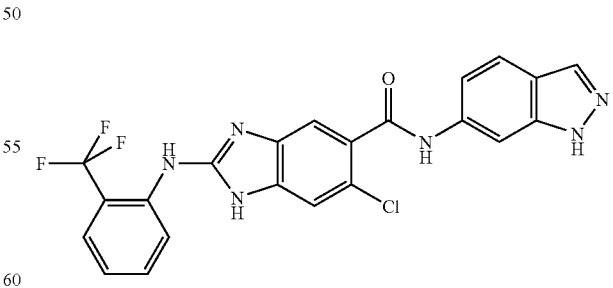

A solution of 4-amino-2-chloro-N-(1H-indazol-6-yl)-5-nitrobenzamide (2 mmol; see Example 154) in ethanol (5 mL) and AcOH (1 mL) was added with iron powder (10 mmol). The reaction mixture was then heated to reflux for 6 h. The contents were cooled to RT, filtered through Celite pad, and the pad washed with ethanol. The filtrates were combined and concentrated in vacuo. The residue obtained was purified on a silica gel column chromatography using MeOH/DCM as eluent to afford 4,5-diamino-2-chloro-N-(1H-indazol-6-yl) benzamide.

The diamine (0.3 mmol) from above was reacted with 1-isothiocyanato-2-trifluoromethylbenzene (0.3 mmol) followed by cyclization in situ using EDC as described in general procedure B to provide 6-chloro-2-(2-trifluoromethylphenylamino)-1H-benzoimidazole-5-carboxylic acid (1H-indazol-6-yl)amide. MS: m/z 471 (M+H)+.

Example 172

Synthesis of 2-((1S,2S,4R)-bicyclo[2,2,1]hept-2-ylamino)-6-chloro-1H-benzoimidazole-5-carboxylic acid (1H-indazol-6-yl)amide

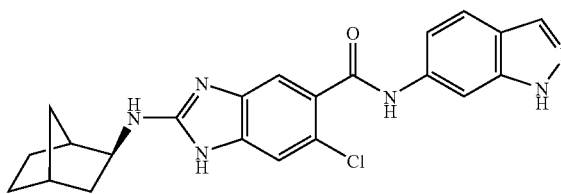

4,5-Diamino-2-chloro-N-(1H-indazol-6-yl)benzamide (0.3 mmol; see Example 171) was reacted with (1S,2S,4R)-2-Isothiocyanato-bicyclo[2.2.1]heptane (0.3 mmol) followed by cyclization in situ using EDC as described in general procedure B to provide 2-((1S,2S,4R))-bicyclo[2.2.1]hept-2-ylamino)-6-chloro-1H-benzoimidazole-5-carboxylic acid (1H-indazol-6-yl)amide. MS: m/z 421 (M+H)+.

Example 173

Synthesis of 6-[4-(2-hydroxyethyl)-piperazin-1-yl]-2-(2-trifluoromethyl-phenylamino)-1H-benzimidazole-5-carboxylic acid (1H-indazol-6-yl)amide

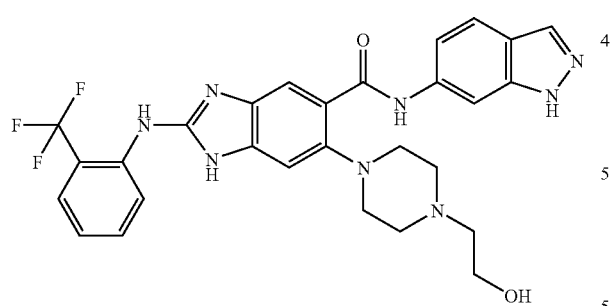

To a solution of 6-piperazin-1-yl-2-(2-trifluoromethylphenylamino)-1H-benzimidazole-5-carboxylic acid (1H-indazol-6-yl)-amide trihydrochloride (0.2 mmol; see Example 88) in methanol (2 mL) was added glyceraldehyde (2 mmol), and the resulting mixture was stirred at RT for 60 min. The reaction mixture was then charged with solid sodium cyanoborohydride (1 mmol), and the stirring was continued at RT for 10h. The reaction mixture was then concentrated in vacuo, and the residue was suspended in water (10 mL) with vigorous stirring. After 30 min, the solid was filtered, washed with water, and dried under vacuum to afford 6-[4-(2-hydroxyethyl)-piperazin-1-yl]-2-(2-trifluoromethyl-phenylamino)-1H-benzimidazole-5-carboxylic acid (1H-indazol-6-yl)amide as a white solid. MS: m/z 565 (M+H)+.

Example 174

Synthesis of {4-[6-(1H-indazol-6-ylcarbamoyl)-2-(2-trifluoromethyl-phenylamino)-3H-benzoimidazol-5-yl]-piperazin-1-yl}acetic acid

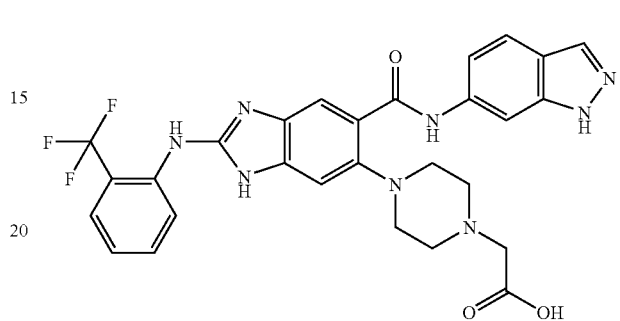

To a solution of 6-piperazin-1-yl-2-(2-trifluoromethylphenylamino)-1H-benzimidazole-5-carboxylic acid (1H-indazol-6-yl)-amide trihydrochloride (0.25 mmol; see Example 88) in methanol (1 mL) was added glyoxylic acid (0.5 mmol), and the resulting mixture was stirred at RT for 60 min. The reaction mixture was then charged with solid sodium cyanoborohydride (0.6 mmol), and the stirring was continued at RT for 10 h. To the reaction mixture was then added a few drops of glacial acetic acid, and the mixture was stirred for 30 min. The volatiles were then removed in vacuo, and the residue was suspended in water (10 mL) with vigorous stirring. After 30 min, the solid was filtered, washed with water, and dried under vacuum to afford {4-[6-(1H-indazol-6-ylcarbamoyl)-2-(2-trifluoromethyl-phenylamino)-3H-benzoimidazol-5-yl]-piperazin-1-yl}acetic acid as a white solid. MS: m/z 579 (M+H)+.

Example 175

Synthesis of 6-(4-Dimethylsulfamoyl-piperazin-1-yl)-2-(2-trifluoromethyl-phenylamino)-1H-benzoimidazole-5-carboxylic acid (1H-indazol-6-yl)-amide

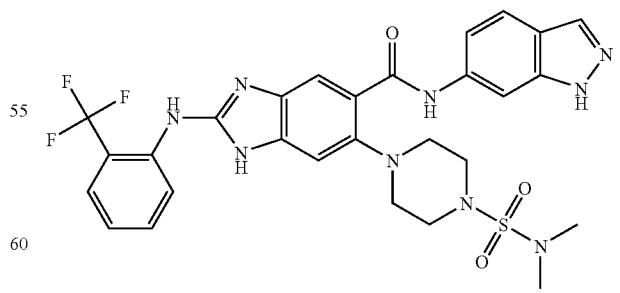

A solution of 6-piperazin-1-yl-2-(2-trifluoromethylphenylamino)-1H-benzimidazole-5-carboxylic acid (1H-indazol-6-yl)-amide trihydrochloride (0.3 mmol; see Example 88) in DMF (1 mL) was added with triethylamine (1.5 mmol) and N,N-dimethylsulfamoyl chloride (0.4 mmol). The resulting mixture was stirred at RT for 4 h and added with hydrazine hydrate (2 mmol). The contents were warmed to 50° C. and stirred vigorously for 60 min. The reaction mixture was then poured into ice cold water, and the solid was filtered, washed with water, and dried under vacuum. The crude product was then purified on a silica gel column chromatography using MeOH/DCM as eluent to afford 6-(4-dimethylsulfamoyl-piperazin-1-yl)-2-(2-trifluoromethylphenylamino)-1H-benzoimidazole-5-carboxylic acid (1H-indazol-6-yl)-amide as a white solid. MS: m/z 628 (M+H)$^+$.

Example 176

Synthesis of {6-[5-(1H-Indazol-6-yl)-1H-imidazol-2-yl]-1H-benzimidazol-2-yl}-(2-trifluoromethylphenyl)-amine

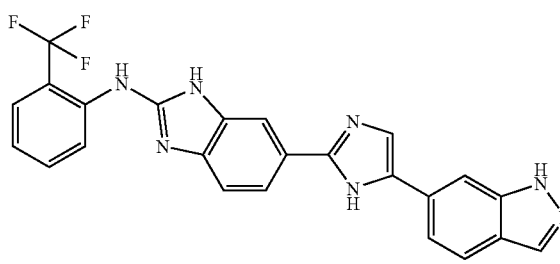

Methyl-3-nitroacetophenone (10 mmol) was reduced under hydrogenation conditions as described in general procedure F to afford 1-(3-amino-4-methylphenyl)ethanone (1.4 g).

Concentrated HCl (2 mL) was added to a mixture of 1-(3-amino-4-methylphenyl)ethanone (8.4 mmol) and NaBF$_4$ (1.2 g, 11 mmol) in H$_2$O (10 mL) and the solution was cooled to 0° C. A solution of NaNO$_2$ (0.58 g, 8.4 mmol) in H$_2$O (1.5 mL) was added dropwise and the mixture was stirred at 0° C. for 30 min. The solid that formed was collected by filtration and washed with H$_2$O (5 mL) followed by Et$_2$O (5 mL) and dried under a reduced pressure. CH$_2$Cl$_2$ (20 mL), KOAc (0.91 g, 9.3 mmol) and 18-crown-6 (50 mg, 0.2 mmol) was added to the solid and the mixture was stirred at room temperature for 4 h. H$_2$O (20 mL) was added and the layers were separated. The organic layer was dried (MgSO$_4$) and the solvent removed at reduced pressure to afford 1-(1H-indazol-6-yl)ethanone (0.52 g).

Pyrrolidone hydrotribromide (1.8 g, 3.6 mmol) was added to a solution of 1-(1H-indazol-6-yl)ethanone (0.5 g, 3 mmol) in THF (10 mL) and the solution was heated at reflux for 2 h. The solution was allowed to cool to room temperature and H$_2$O (30 mL) was added and the mixture was extracted with EtOAc (3×20 mL) and dried (MgSO$_4$). The solvent was removed at reduced pressure to afford 2-bromo-1-(1H-indazol-6-yl)-ethanone, which was used directly in the next step with no purification.

DIEA (0.7 mL, 3.6 mmol) was added to a solution of 2-bromo-1-(1H-indazol-6-yl)ethanone (3 mmol) and 4-amino-3-nitrobenzoic acid (0.643 g, 3.5 mmol) in DMF (10 mL) and the solution was stirred at room temperature for 2 h. NH$_4$OAc (5 g, 65 mmol) was added to the solution, followed by HOAc (10 mL) and the mixture was stirred at 140° C. for 2 h. The mixture was cooled to room temperature and poured into H$_2$O (30 mL). The precipitate was collected by filtration, washed with H$_2$O (10 mL) and dried under reduced pressure to afford 4-[5-(1H-indazol-6-yl)-1H-imidazol-2-yl]-2-nitrophenylamine (0.56 g).

The nitro aniline from above (1 mmol) was reduced under hydrogenation conditions as described in general procedure F to afford 4-[5-(1H-indazol-6-yl)-1H-imidazol-2-yl]-benzene-1,2-diamine.

The diamine (0.5 mmol) from above was reacted with 1-isothiocyanato-2-trifluoromethylbenzene (0.5 mmol) followed by cyclization in situ using EDC as described in general procedure B to provide {6-[5-(1H-Indazol-6-yl)-1H-imidazol-2-yl]-1H-benzimidazol-2-yl}-(2-trifluoromethylphenyl)-amine. MS: m/z 460 (M+H)$^+$.

Example 177

Synthesis of 6-(2-dimethylamino-ethylsulfanyl)-2-(2-trifluoromethylphenylamino)-1H-benzoimidazole-5-carboxylic acid (1H-indazol-6-yl)-amide

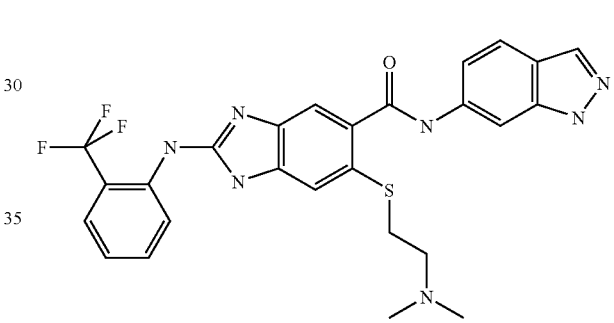

NaH (2 mmol) was added to a solution of 2-dimethylaminoethanethiol (2 mmol) in NMP (2 mL), and the mixture was stirred at room temperature for 10 min. 4-Amino-2-chloro-N-(1H-indazol-6-yl)-5-nitrobenzamide (1 mmol; see Example 154) was added to the mixture, and the mixture was stirred at 60-65° C. for 3 h. Water (4 mL) was added to the mixture, and the mixture was extracted with EtOAc (3×10 mL) and dried over MgSO$_4$. The combined extracts were dried (MgSO$_4$), and the solvent was removed at reduced pressure to afford the desired product, 4-amino-2-(2-dimethylaminoethylsulfanyl)-N-(1H-indazol-6-yl)-5-nitro-benzamide, which was used without further purification.

The nitro aniline from above (1 mmol) was reduced under hydrogenation conditions as described in general procedure F to afford 4,5-diamino-2-(2-dimethylaminoethylsulfanyl)-N-(1H-indazol-6-yl)-benzamide.

The diamine (0.5 mmol) from above was reacted with 1-isothiocyanato-2-trifluoromethylbenzene (0.5 mmol) followed by cyclization in situ using EDC as described in general procedure B to provide 6-(2-dimethylaminoethylsulfanyl)-2-(2-trifluoromethylphenylamino)-1H-benzoimidazole-5-carboxylic acid (1H-indazol-6-yl)-amide. MS: m/z 540 (M+H)$^+$.

Example 178

Synthesis of 5-ethyl-8-(1H-indazol-6-yl)-2-(2-trifluoromethylphenylamino)-5,6,7,8-tetrahydro-3H-1,3,5,8-tetraazacyclohepta[f]inden-9-one

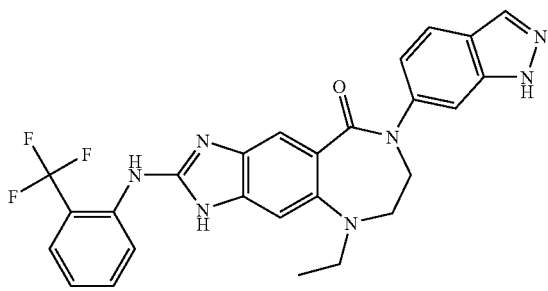

To a solution of 4-amino-2-chloro-N-(1H-indazol-6-yl)-5-nitrobenzamide (5 mmol; see Example 154) in dioxane (10 mL) was added 2-ethylaminoethanol (15 mmol). The resulting mixture was heated at reflux for 10 h. The reaction mixture was cooled to room temperature and diluted with water (20 mL). The solid formed was collected by filtration, washed with water, and dried in vacuo. The product, 4-amino-2-[ethyl(2-hydroxyethyl)amino]-N-(1H-indazol-6-yl)-5-nitrobenzamide, was used without any purification.

MeSO$_2$Cl (0.5 mL, 6.3 mmol) was added dropwise to a solution of the nitroaniline from above (1 g, 3.0 mmol) in THF (10 mL) containing DIEA (1.6 mL) and pyridine (1.5 mL). The solution was stirred at room temperature for 1 h and poured into water (10 mL). The mixture was extracted with EtOAc (3×10 mL), and the combined extracts were dried over MgSO$_4$. The solvent was removed under reduced pressure to afford methanesulfonic acid 2-{[5-amino-2-(1-methanesulfonyl-1H-indazol-6-ylcarbamoyl)-4-nitrophenyl]ethylamino}ethyl ester (1.4 g, 2.6 mmol).

NaH (60%, 266 mg, 6.7 mol) was added to a solution of crude methanesulfonic acid 2-{[5-amino-2-(1-methanesulfonyl-1H-indazol-6-ylcarbamoyl)-4-nitrophenyl]ethylamino}ethyl ester (2.6 mmol) in THF (10 mL) at room temperature. The solution was stirred at reflux for 3 h. The solvent was removed under reduced pressure, and the residue was taken up in EtOAc and washed with water (10 mL). The organic layer was separated, dried over MgSO$_4$, and the solvent was removed under reduced pressure to afford 8-amino-1-ethyl-4-(1-methanesulfonyl-1H-indazol-6-yl)-7-nitro-1,2,3,4-tetrahydro-benzo[e][1,4]diazepin-5-one (1.1 g, 2.5 mmol).

Hydrazine (0.6 mL) was added to a solution of 8-amino-1-ethyl-4-(1-methanesulfonyl-1H-indazol-6-yl)-7-nitro-1,2,3,4-tetrahydro-benzo[e][1,4]diazepin-5-one (1.1 g, 2.5 mmol) in 1:1 THF/MeOH (20 mL). The solution was stirred at room temperature for 16 h. The solvent was removed under reduced pressure to afford 8-amino-1-ethyl-4-(1H-indazol-6-yl)-7-nitro-1,2,3,4-tetrahydrobenzo[e][1,4]diazepin-5-one (815 mg).

The nitro aniline from above (1 mmol) was reduced under hydrogenation conditions as described in general procedure F to afford 7,8-Diamino-1-ethyl-4-(1H-indazol-6-yl)-1,2,3,4-tetrahydrobenzo[e][1,4]diazepin-5-one.

The diamine (0.5 mmol) from above was reacted with 1-isothiocyanato-2-trifluoromethylbenzene (0.5 mmol) followed by cyclization in situ using EDC as described in general procedure B to provide 5-ethyl-8-(1H-indazol-6-yl)-2-(2-trifluoromethylphenylamino)-5,6,7,8-tetrahydro-3H-1,3,5,8-tetraazacyclohepta[f]inden-9-one. MS: m/z 506 (M+H)$^+$.

Example 179

Synthesis of 6-imidazol-1-yl-2-(2-trifluoromethylphenylamino)-3H-benzimidazole-5-carboxylic acid (1H-indazol-6-yl)-amide

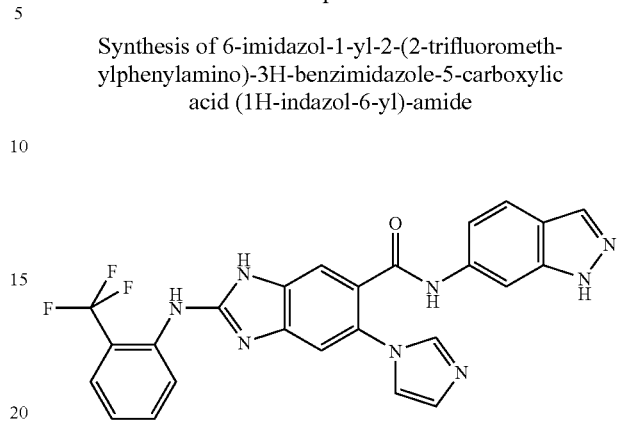

To a solution of 4-amino-2-chloro-N-(1H-indazol-6-yl)-5-nitrobenzamide (1 mmol; see Example 154) in NMP (2 mL) was added with imidazole (5 mmol). The resulting mixture was subjected to microwave irradiation at 120° C. for 2 h. The reaction mixture was cooled to room temperature and diluted with water (30 mL). The solid formed was collected by filtration, washed with water, and dried in vacuo. The product, 4-amino-2-imidazol-1-yl-N-(1H-indazol-6-yl)-5-nitro-benzamide, obtained as a yellow solid was used without any purification.

The nitro compound (0.5 mmol) obtained as above, was reduced under hydrogenation conditions as described in general procedure F to afford 4,5-diamino-2-imidazol-1-yl-N-(1H-indazol-6-yl)-benzamide.

The diamine (0.3 mmol) from above was reacted with 1-isothiocyanato-2-trifluoromethylbenzene (0.3 mmol) followed by cyclization in situ using EDC as described in general procedure B to provide 6-imidazol-1-yl-2-(2-trifluoromethylphenylamino)-3H-benzimidazole-5-carboxylic acid (1H-indazol-6-yl)-amide. MS: m/z 503 (M+H)$^+$.

Example 180

Synthesis of 2-(2-trifluoromethylphenylamino)-benzooxazole-5-carboxylic acid (1H-indazol-6-yl)-amide

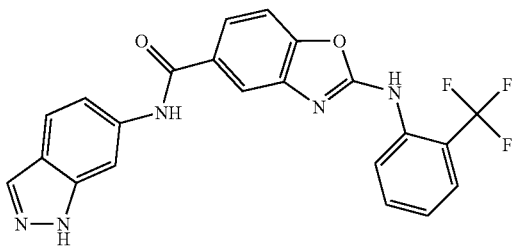

Following the general Procedure E, 4-Hydroxy-3-nitrobenzoic acid (5 mmol) and 6-aminoindazole (5 mmol) were utilized to prepare 4-hydroxy-N-(1H-indazol-6-yl)-3-nitrobenzamide as a yellow solid.

The nitrophenol (3 mmol) obtained as above, was reduced under hydrogenation conditions as described in general procedure F to afford 3-amino-4-hydroxy-N-(1H-indazol-6-yl)-benzamide.

A solution of the aminophenol (0.5 mmol) from above in DMF (2 mL) was added with 1-isothiocyanato-2-trifluoromethylbenzene (0.6 mmol) and DIEA (1 mmol). The reaction mixture was subjected to microwave irradiation at 120° C. for 1 h. The reaction mixture was cooled to room temperature, diluted with water (20 mL). The solid formed was collected by filtration, washed with water, and dried in vacuo. The crude product was purified on a silica gel column chromatography using MeOH/DCM as eluent to provide 2-(2-trifluoromethylphenylamino)-benzooxazole-5-carboxylic acid (1H-indazol-6-yl)-amide, obtained as a yellow solid. MS: m/z 438 (M+H)$^+$.

Example 181

Synthesis of 2-(1-benzyl-1H-imidazol-2-ylamino)-6-(4-methylpiperazin-1-yl)-1H-benzimidazole-5-carboxylic acid (1H-indazol-6-yl)-amide

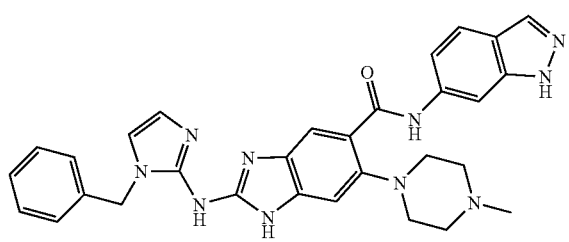

A solution of 2-chloro-4-fluoro-N-(1H-indazol-6-yl)-5-nitrobenzamide (10 mmol) in dioxane (20 mL) was reacted with aqueous NH$_4$OH using the conditions described in Example 115. After the formation of 2-amino-4-fluoro-N-(1H-indazol-6-yl)-5-nitrobenzamide was complete, the reaction mixture was charged with N-methylpiperazine (40 mmol) (NMP). The contents were heated at reflux for 10 h, and the reaction mixture was cooled to RT. The contents were poured onto ice cold water with vigorous stirring. The solid formed was collected by filtration, washed with water, and dried in vacuo to provide the product, 4-amino-N-(1H-indazol-6-yl)-2-(4-methylpiperazin-1-yl)-5-nitrobenzamide as a yellow solid.

The nitro compound (6 mmol) obtained as above, was reduced under hydrogenation conditions as described in general procedure F to afford 4,5-diamino-2-(4-methylpiperazin-1-yl)-N-(1H-indazol-6-yl)-benzamide.

Benzylbromide (3 mmol) and K$_2$CO$_3$ (6 mmol) were added to a solution of 2-nitroimidazole (2 mmol) in DMF (6 mL). The mixture was stirred at 60-70° C. for 4 h or overnight. The contents were cooled to room temperature, and water (30 mL) was added. The mixture was extracted with EtOAc (3×15 mL). The combined extracts were dried over MgSO$_4$, filtered, and the solvent was removed in vacuo to afford 1-benzyl-2-nitro-1H-imidazole. The product used for further transformation without further purification.

The nitroimidazole (1.5 mmol) from above reduced using iron powder and ammonium chloride employing the procedure described in Example 159 to yield 1-benzyl-2-amino-1H-imidazole which was used without any purification.

The aforementioned aminoimidazole derivative was converted to 1-benzyl-2-isothiocyanato-1H-imidazole following the general procedure A.

The isothiocyanate (1 mmol) from above was reacted with 3,4-diamino-N-(1H-indazol-6-yl)-benzamide (1 mmol) followed by cyclization using EDC as described in general procedure B to 2-(1-benzyl-1H-imidazol-2-ylamino)-6-(4-methylpiperazin-1-yl)-1H-benzimidazole-5-carboxylic acid (1H-indazol-6-yl)-amide. MS: m/z 547 (M+H)$^+$.

Example 182

Synthesis of 4-[2-(1-cyclopentyl-1H-imidazol-2-ylamino)-6-(1H-indazol-6-ylcarbamoyl)-3H-benzoimidazol-5-yl]-piperazine-1-carboxylic acid tert-butyl ester

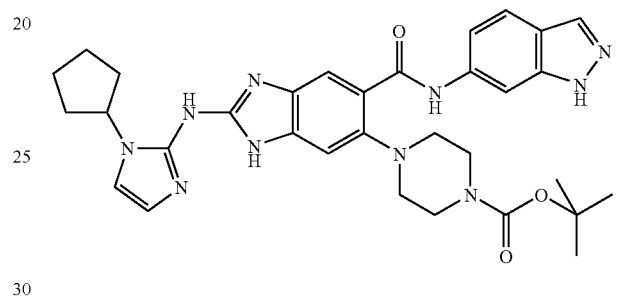

Bromocyclopentane (14 mmol) and 2-nitroimidazole (10 mmol) were used to prepare 1-cyclopentyl-2-nitro-1H-imidazole following the alkylation procedure described for Example 181. The product, thus obtained was reduced under hydrogenation conditions as described in general procedure F to afford 1-cyclopentyl-2-amino-1H-imidazole. This aminoimidazole derivative was converted to 1-cyclopentyl-2-isothiocyanato-1H-imidazole following the general procedure A.

The isothiocyanate (1 mmol) from above was reacted with 4-[4,5-diamino-2-(1H-indazol-6-ylcarbamoyl)-phenyl]piperazine-1-carboxylic acid tert-butyl ester (1 mmol; see Example 169) followed by cyclization using EDC as described in general procedure B to 4-[2-(1-cyclopentyl-1H-imidazol-2-ylamino)-6-(1H-indazol-6-ylcarbamoyl)-3H-benzoimidazol-5-yl]-piperazine-1-carboxylic acid tert-butyl ester. MS: m/z 611 (M+H)$^+$.

Example 183

Synthesis of 2-(1-cyclopentyl-1H-imidazol-2-ylamino)-6-piperazin-1-yl-1H-benzoimidazole-5-carboxylic acid (1H-indazol-6-yl)amide trihydrochloride

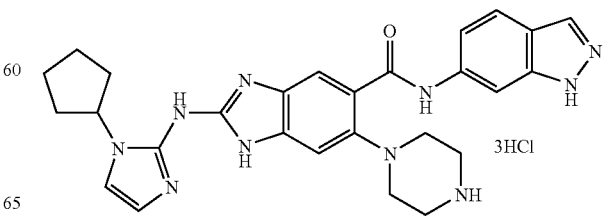

The product from Example 182 was treated with 4M HCl in dioxane employing the procedure described for Example 156 to afford 2-(1-cyclopentyl-1H-imidazol-2-ylamino)-6-piperazin-1-yl-1H-benzoimidazole-5-carboxylic acid (1H-indazol-6-yl)amide as a hydrochloride salt. MS: m/z 511 (M+H)⁺.

Example 184

Synthesis of 2-(1-cyclopentyl-1H-imidazol-2-ylamino)-6-(4-isopropylpiperazin-1-yl)-1H-benzimidazole-5-carboxylic acid (1H-indazol-6-yl)amide

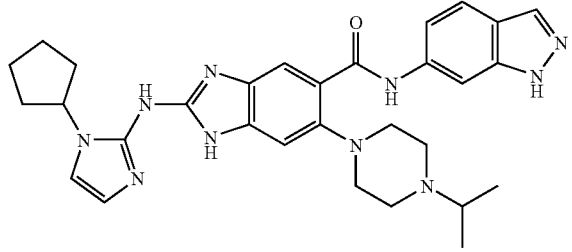

To a solution of 4-amino-2-chloro-N-(1H-indazol-6-yl)-5-nitrobenzamide (1 mmol; see Example 154) in dioxane (2 mL) was added with N-isopropylpiperazine (4 mmol). The resulting mixture was heated at reflux for 10 h. The reaction mixture was cooled to room temperature and diluted with water (20 mL) with vigorous stirring. The solid formed was collected by filtration, washed with water, and dried in vacuo to provide the product, 4-amino-N-(1H-indazol-6-yl)-2-(4-isopropyl-piperazin-1-yl)-5-nitro-benzamide as a yellow solid.

The nitro compound (0.5 mmol) as above was reduced under hydrogenation conditions as described in general procedure F to afford 4,5-diamino-N-(1H-indazol-6-yl)-2-(4-isopropylpiperazin-1-yl)-benzamide.

The diamine (0.3 mmol) from above was reacted with to 1-cyclopentyl-2-isothiocyanato-1H-imidazole (0.3 mmol; see Example 182) followed by cyclization in situ using EDC as described in general procedure B to provide 2-(1-cyclopentyl-1H-imidazol-2-ylamino)-6-(4-isopropylpiperazin-1-yl)-1H-benzimidazole-5-carboxylic acid (1H-indazol-6-yl)amide. MS: m/z 553 (M+H)⁺.

Following the procedure in Example 184, 4-amino-2-chloro-N-(1H-indazol-6-yl)-5-nitrobenzamide was utilized to synthesize the compounds listed in Table 13.

TABLE 13

| Ex. | R | MS (m/z) |
|---|---|---|
| 185 | 4-ethylpiperazin-1-yl | 539 |
| 186 | (2-dimethylaminoethyl)-methylamino | 527 |
| 187 | 4-methyl[1,4]diazepan-1-yl | 539 |

Using 1-alkyl-2-isothiocyanato-1H-imidazole (prepared using the procedure in Example 182) and 4,5-diamino-2-(4-methylpiperazin-1-yl)-N-(1H-indazol-6-yl)-benzamide (see Example 181), following compounds (Table 14) were synthesized employing the general procedure B:

TABLE 14

| Ex. | R | MS (m/z) |
|---|---|---|
| 188 | Cyclohexyl | 539 |
| 189 | Methyl | 471 |
| 190 | Cyclohexylmethyl | 553 |
| 191 | Isobutyl | 513 |
| 192 | Cyclobutyl | 511 |
| 193 | 1-Ethylpropyl | 527 |
| 194 | n-Butyl | 513 |
| 195 | 2-Methoxyethyl | 515 |
| 196 | Ethyl | 485 |

Using 1-alkyl-2-isothiocyanato-1H-imidazole (prepared using the procedure in Example 182) and 4,5-Diamino-N-benzothiazol-6-yl-2-(4-methylpiperazin-1-yl)-benzamide (see Example 141), following compounds (Table 15) were synthesized employing the general procedure B:

TABLE 15

| Ex. | R | MS (m/z) |
|---|---|---|
| 197 | 2-Methoxyethyl | 532 |
| 198 | Ethyl | 502 |

Example 199

Synthesis of 2-(1-cyclopentyl-1H-imidazol-2-ylamino)-6-(4-methylpiperazin-1-yl)-1H-benzoimidazole-5-carboxylic acid (1H-indazol-5-yl)-amide

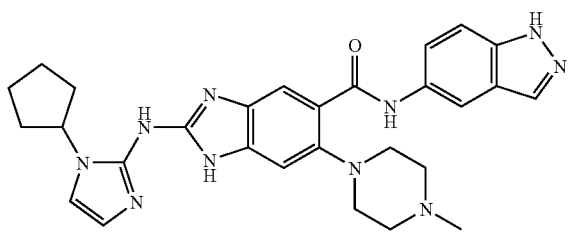

5-aminobenzothioazole (5 mmol) was reacted with 4-chloro-2-fluoro-5-nitrobenzoyl chloride (5 mmol) employing the procedure described in Example 115. The product, 2-chloro-4-fluoro-N-(1H-indazol-5-yl)-5-nitrobenzamide, was used for further transformation without any purification.

A solution of 2-chloro-4-fluoro-N-(1H-indazol-5-yl)-5-nitrobenzamide (2 mmol) in dioxane (4 mL) was reacted with aqueous NH₄OH using the conditions described in Example 115. After the formation of 2-amino-4-fluoro-N-(1H-indazol-6-yl)-5-nitrobenzamide was complete, the reaction mixture was charged with N-methylpiperazine (8 mmol). The contents were heated at reflux for 10 h, and the reaction mixture was cooled to RT. The contents were poured onto ice cold water with vigorous stirring. The solid formed was collected by filtration, washed with water, and dried in vacuo to provide the product, 4-amino-N-(1H-indazol-5-yl)-2-(4-methylpiperazin-1-yl)-5-nitrobenzamide as a yellow solid.

The nitro compound (1 mmol) obtained as above, was reduced under hydrogenation conditions as described in general procedure F to afford 4,5-diamino-2-(4-methylpiperazin-1-yl)-N-(1H-indazol-5-yl)-benzamide.

The diamine (0.3 mmol) from above was reacted with to 1-cyclopentyl-2-isothiocyanato-1H-imidazole (0.3 mmol; see Example 182) followed by cyclization in situ using EDC as described in general procedure B to provide 2-(1-cyclopentyl-1H-imidazol-2-ylamino)-6-(4-methyl-piperazin-1-yl)-1H-benzoimidazole-5-carboxylic acid (1H-indazol-5-yl)-amide. MS: m/z 525 (M+H)⁺.

The procedure described in Example 199 was adapted to synthesize the following compounds in Table 16

TABLE 16

| Ex. | Ar | MS (m/z) |
|---|---|---|
| 200 | 1H-benzotriazol-5-yl | 526 |
| 201 | Benzothiazol-6-yl | 542 |

TABLE 16-continued

| Ex. | Ar | MS (m/z) |
|---|---|---|
| 202 | 2-Oxo-2,3-dihydro-1H-indol-5-yl | 540 |
| 203 | 1H-indol-6-yl | 524 |
| 204 | 3H-benzoimidazol-5-yl | 525 |
| 205 | Benzothiazol-5-yl | 542 |

Example 206

Synthesis of 2-(1-thietan-3-yl-1H-imidazol-2-ylamino)-6-(4-methylpiperazin-1-yl)-1H-benzoimidazole-5-carboxylic acid (1H-indazol-5-yl)-amide

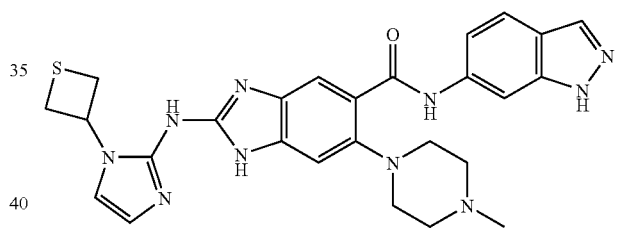

2-Nitroimidazole (0.5 g, 4.4 mmol) was added to a solution of KOH (6.6 mmol) in water (10 mL). 2-(Chloromethyl) thiirane (0.72 g, 6.6 mmol) was added to the solution and the solution was stirred at 65-70° C. for 1 h. The solvent was removed by distillation and the residue was purified by flash column chromatography with CH₂Cl₂ as eluent to afford 0.43 g of desired product 2-nitro-1-thietan-3-yl-1H-imidazole (52%).

The nitro compound (2 mmol) obtained as above, was reduced under hydrogenation conditions as described in general procedure F to 2-amino-1-thietan-3-yl-1H-imidazole.

The aforementioned aminoimidazole derivative was converted to 1-thietan-3-yl-2-isothiocyanato-1H-imidazole following the general procedure A.

4,5-diamino-2-(4-methylpiperazin-1-yl)-N-(1H-indazol-6-yl)-benzamide (0.5 mmol; see Example 181) was reacted with 1-thietan-3-yl-2-isothiocyanato-1H-imidazole (0.5 mmol) followed by cyclization in situ using EDC as described in general procedure B to provide 2-(1-thietan-3-yl-1H-imidazol-2-ylamino)-6-(4-methylpiperazin-1-yl)-1H-benzoimidazole-5-carboxylic acid (1H-indazol-5-yl)-amide. MS: m/z 529 (M+H)⁺.

Example 207

Synthesis of 2-amino-6-(4-methylpiperazin-1-yl)-1H-benzimidazole-5-carboxylic acid (1H-indazol-6-yl)-amide hydrobromide

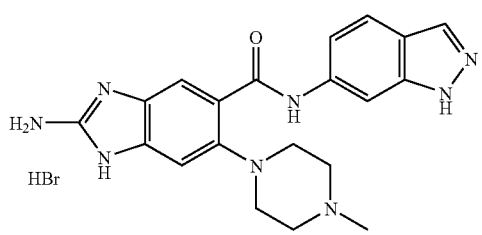

To a solution of 4,5-diamino-2-(4-methylpiperazin-1-yl)-N-(1H-indazol-6-yl)-benzamide (2 mmol; see Example 181) in 10% aqueous EtOH (6 mL) was added cyanogen bromide (2.2 mmol), and the mixture was heated at reflux for 4 h. The reaction mixture was then concentrated in vacuo, and the residue obtained was suspended in diethyl ether with vigorous stirring. The solid obtained was collected by filtration, washed with diethyl ether, and dried in vacuo to afford 2-amino-6-(4-methylpiperazin-1-yl)-1H-benzimidazole-5-carboxylic acid (1H-indazol-6-yl)-amide as a hydrobromide salt. MS: m/z 391 (M+H)$^+$.

Example 208

Synthesis of 2-(3-cyclopentyl-3-ethylureido)-6-(4-methyl-piperazin-1-yl)-1H-benzimidazole-5-carboxylic acid (1H-indazol-6-yl)-amide

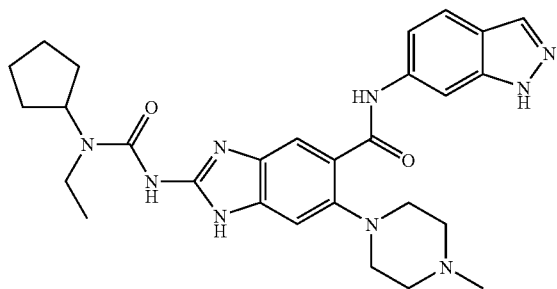

A solution of cyclopentylethylamine (3 mmol) in anhydrous THF (3 mL) was added dropwise to a solution of phosgene (4 mmol) at 0° C. After the addition was complete, the reaction mixture was stirred for 30 min at 0° C. The volatiles were removed in vacuo, and the residue obtained was dried under vacuum. The crude product, cyclopentylethylcarbamoyl chloride was used for further transformation without any purification.

A solution of afford 2-amino-6-(4-methylpiperazin-1-yl)-1H-benzimidazole-5-carboxylic acid (1H-indazol-6-yl)-amide hydrobromide (0.5 mmol) in DMF (2 mL) was added with DIEA (2 mmol) followed by the carbamoyl chloride (0.6 mmol), obtained as above, at RT. The resulting mixture was stirred for 4 h. Hydrazine hydrate (0.25 mL) was added to the reaction mixture. The contents were warmed to 50° C. and stirred for 60 min. The reaction mixture was then cooled to RT, diluted with ice cold water (10 mL) and extracted with EtOAc (2×10 mL). The combined extracts were washed with water (10 mL) and brine (10 mL). After removal of the solvent, the residue obtained was purified on a silica gel column chromatography to yield 2-(3-cyclopentyl-3-ethylureido)-6-(4-methyl-piperazin-1-yl)-1H-benzimidazole-5-carboxylic acid (1H-indazol-6-yl)-amide. MS: m/z 530 (M+H)$^+$.

Example 209

Synthesis of 2-mercapto-6-(4-methylpiperazin-1-yl)-1H-benzimidazole-5-carboxylic acid (1H-indazol-6-yl)-amide

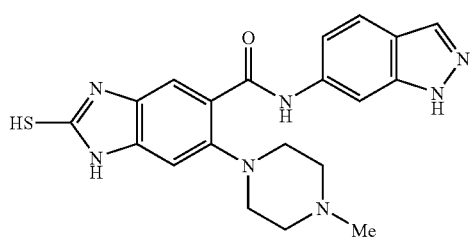

To a solution of 4,5-diamino-2-(4-methylpiperazin-1-yl)-N-(1H-indazol-6-yl)-benzamide (0.5 mmol; see Example 181) in DMF (1 mL) was added thiocarbonyl diimidazole (0.55 mmol). Following the addition, the mixture was warmed at 45° C. for 1 h. The reaction mixture was cooled to RT, and the contents were poured onto ice cold water with vigorous stirring. The solid formed was collected by filtration, washed with water, and dried in vacuo to provide the product, 2-mercapto-6-(4-methylpiperazin-1-yl)-1H-benzimidazole-5-carboxylic acid (1H-indazol-6-yl)-amide as a yellow solid.

Example 210

Synthesis of 2-(1-cyclopentyl-1H-benzimidazol-2-ylamino)-6-(4-methylpiperazin-1-yl)-1H-benzimidazole-5-carboxylic acid (1H-indazol-6-yl)-amide

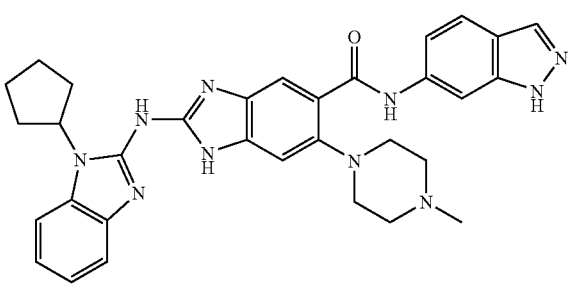

A solution of 2-fluoro-1-nitrobenzene (2 mmol) in THF was added with cyclopentylamine (2.5 mmol) and K$_2$CO$_3$ (3 mmol). The resulting mixture was heated at 60° C. for 4 h. The contents were cooled to RT, and the solid was filtered off. The filtrate was concentrated in vacuo, and the residue was dried under vacuum. The product, 2-cyclopentylamino-1-nitrobenzene, was used for further transformation without any purification.

The nitroaniline (2 mmol) obtained as above was reduced under hydrogenation conditions as described in general procedure F to N-cyclopentylbenzene-1,2-diamine.

A solution of the diamine (1.5 mmol) obtained as above in 10% aqueous EtOH (4 mL) was added with cyanogen bromide (1.7 mmol) and was heated at reflux for 4 h. The reaction mixture was then cooled to RT, added with solid K₂CO₃ (2 mmol) and stirred vigorously for 30 min. The solid was then filtered off, and the filtrate was concentrated under vacuum to afford 1-cyclopentyl-1H-benzoimidazol-2-ylamine which was used for further transformation without any purification.

The aforementioned aminobenzimidazole (1 mmol) derivative was converted to 1-cyclopentyl-2-isothiocyanato-1H-benzimidazole following the general procedure A.

4,5-diamino-2-(4-methylpiperazin-1-yl)-N-(1H-indazol-6-yl)-benzamide (0.5 mmol; see Example 181) was reacted with 1-cyclopentyl-2-isothiocyanato-1H-benzimidazole (0.5 mmol) followed by cyclization in situ using EDC as described in general procedure B to 2-(1-cyclopentyl-1H-benzimidazol-2-ylamino)-6-(4-methylpiperazin-1-yl)-1H-benzimidazole-5-carboxylic acid (1H-indazol-6-yl)-amide. MS: m/z 575 (M+H)⁺.

Example 211

Synthesis of [6-(1H-indazol-6-yloxy)-1H-benzimidazol-2-yl]-(2-trifluoromethylphenyl)-amine

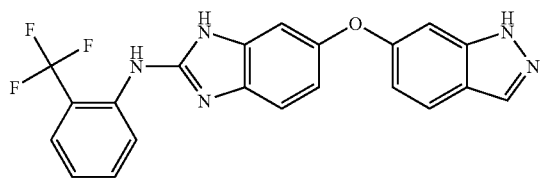

To a stirred suspension of 6-aminoindazole (20 mmol) in concentrated HCl (6 mL) at 0° C. was added a solution of NaNO₂ (22 mmol) in water (12 mL) in portions. During the addition, the temperature of the reaction mixture was maintained at 0-5° C., and the stirring continued for additional 45 min. The contents were then added into a flask containing 1% aqueous HCl (200 mL), and heated at 100° C. The reaction mixture was then stirred at 100° C. for 5 h. The contents were cooled to RT, neutralized to pH 7 using 5% aqueous Na₂CO₃, and extracted with EtOAc (2×70 mL). Combined organic layers were washed with brine and dried over anhydrous Na₂SO₄. Removal of solvent under vacuum provided 6-hydroxyindazole as dark brown solid, which was used for further transformation without any purification.

To a stirred solution of 2-chloro-4-fluoro-1-nitrobenzene (3 mmol) in DMF (5 mL) was added 6-hydroxyindazole (3 mmol) and K₂CO₃ (6 mmol). The contents were heated at 90° C. for 6 h. The reaction mixture was cooled to RT, and the contents were poured onto ice cold water with vigorous stirring. The solid formed was collected by filtration, washed with water, and dried in vacuo to provide the product, 6-(3-chloro-4-nitrophenoxy)-1H-indazole as a yellow solid, which was used for further transformation without any purification.

A stirred solution of the nitro compound (2 mmol) in DMF (4 mL) was added with benzylamine (4 mmol) and contents were heated at 100° C. for 6 h. The reaction mixture was cooled to RT and the contents were poured onto ice cold water with vigorous stirring. The solid formed was collected by filtration, washed with water, and dried in vacuo. The residue obtained was purified on silica gel column chromatography using hexane/EtOAC as eluent to provide the product, benzyl-[5-(1H-indazol-6-yloxy)-2-nitrophenyl]-amine as a yellow solid.

The nitroaniline (1 mmol) obtained as above was reduced under hydrogenation conditions as described in general procedure F to 4-(1H-Indazol-6-yloxy)-benzene-1,2-diamine.

The diamine (0.3 mmol) from above was reacted with 1-isothiocyanato-2-trifluoromethylbenzene (0.3 mmol) followed by cyclization in situ using EDC as described in general procedure B to provide [6-(1H-indazol-6-yloxy)-1H-benzimidazol-2-yl]-(2-trifluoromethylphenyl)-amine. MS: m/z 410 (M+H)⁺.

Example 212

Synthesis of {5-[2-(1H-indazol-6-yl)-ethyl]-1H-benzimidazol-2-yl}-(2-trifluoromethylphenyl)amine

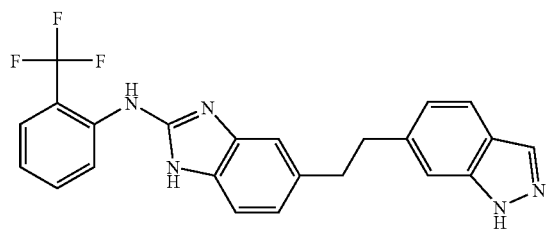

A solution of [5-(1H-Indazol-6-ylethynyl)-1H-benzoimidazol-2-yl]-(2-trifluoromethylphenyl)-amine (0.3 mmol; see Example 159) in ethanol (3 mL) was reduced under hydrogenation conditions at 50 psi as described in general procedure to yield {5-[2-(1H-indazol-6-yl)-ethyl]-1H-benzimidazol-2-yl}-(2-trifluoromethylphenyl)amine. MS: m/z 422 (M+H)⁺.

Example 213

Synthesis of 3-[6-Diethylamino-5-(1H-indazol-6-ylcarbamoyl)-1H-benzimidazol-2-ylamino]-benzoic acid

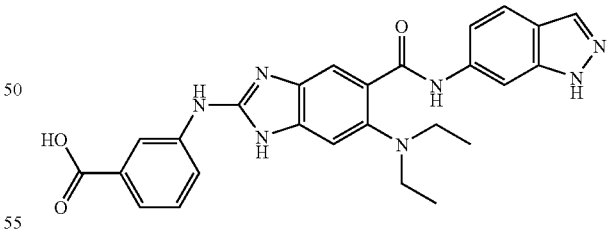

To a solution of 3-[6-diethylamino-5-(1H-indazol-6-ylcarbamoyl)-1H-benzimidazol-2-ylamino]-benzoic acid methyl ester (0.2 mmol; see Example 115) in methanol (2 mL) and THF (2 mL) was added 1M aqueous LiOH solution (2 mL). The resulting solution was then stirred at RT until the reaction was complete. The pH of the reaction mixture was adjusted with 5% aqueous citric acid solution to bring its pH to 4-5. The solid obtained was filtered, washed with ice-cold water, and dried under vacuum to afford 3-[6-diethylamino-5-(1H-indazol-6-ylcarbamoyl)-1H-benzimidazol-2-ylamino]-benzoic acid as a white solid. MS: m/z 484 (M+H)⁺.

Example 214

Synthesis of 3-[5-(Benzothiazol-6-ylcarbamoyl)-6-diethylamino-1H-benzoimidazol-2-ylamino]-benzoic acid methyl ester

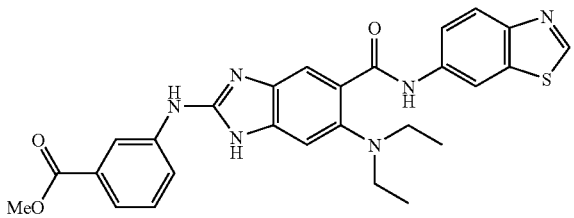

4,5-Diamino-N-benzothiazol-6-yl-2-diethylaminobenzamide (0.3 mmol; see Example 133) from above was reacted with 3-isothiocyanatobenzoic acid methyl ester (0.3 mmol) followed by cyclization in situ using EDC as described in general procedure B to obtain 3-[5-(benzothiazol-6-ylcarbamoyl)-6-diethylamino-1H-benzoimidazol-2-ylamino]-benzoic acid methyl ester. MS: m/z 515 (M+H)$^+$.

Example 215

Synthesis of 3-[5-(Benzothiazol-6-ylcarbamoyl)-6-diethylamino-1H-benzoimidazol-2-ylamino]-benzoic acid

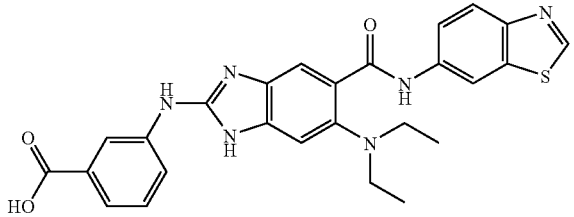

The methyl ester (0.2 mmol) from Example 214 was hydrolyzed employing the conditions described for Example 216 to yield 3-[5-(benzothiazol-6-ylcarbamoyl)-6-diethylamino-1H-benzoimidazol-2-ylamino]-benzoic acid as a white solid. MS: m/z 501 (M+H)$^+$.

Biological Data

The compounds of the present invention elicit measurable pharmacological responses. The compounds of the present invention in Table 1 have a binding affinity (IC$_{50}$<1 µM) for aurora kinases and may be selective for aurora kinases as compared to other kinases In addition to the binding to aurora kinases, compounds of the present invention may also measurably inhibit the proliferation of tumor cells.

Example 216

Aurora A, B, C Enzyme Assays

Aurora kinase assays utilize the peptide substrate biotin-ahx-LRRWSLGLRRWSLG as a phosphoryl group acceptor.

Assays are performed in 96-well U-bottom plates. Aurora A and Aurora C enzymes are purchased from PanVera. Aurora B enzyme is purchased from BPS Bioscience. Compounds are diluted in DMSO prior to addition in the assay. Typically, assays are performed by incubating enzyme (0.2-10 nM) with or without inhibitor, 0.1-1 µCi γ$^{33}$P-ATP (Perkin Elmer), 0.1-100 µM ATP, 0.1-10 mM MnCl$_2$, 1-10 µM sodium orthovanadate, 1-10 mM DTT, and 1-100 µM peptide together for the time range of 5-120 min at 37° C. in a final assay volume of 60 µL. The buffer used to bring the final assay volume up to 60 µL is 50 mM MOPS, pH 7.0, containing 1-5% DMSO and 0.05% BSA. Reactions are terminated by addition of 0.2-2 volumes of 0.75% phosphoric acid.

Detection of peptide phosphorylation is accomplished by scintillation counting using a beta counter (TopCount) following collection of peptide onto P81 96-well filter plates (Whatman). Total control cpm (C$^+$) and background control cpm (C$^-$) wells contain DMSO instead of compound. Background control (C$^-$) wells lack peptide. Total (C$^+$) minus background (C$^-$) counts are assumed to be proportional to initial reaction velocity. Percent enzyme inhibition is calculated as 1−[(cpm$_{sample}$−C$^-$)/(C$^+$−C$^-$)]×100%. IC$_{50}$ values are determined from % enzyme inhibition versus compound concentration curve plots using GraphPad Prism™ according to the 4 parameter logistic equation Y=Bottom+(Top−Bottom)/1+10^((LogEC50−X)*HillSlope)) where X is the logarithm of compound concentration and Y is percent inhibition.

Each of the compounds in Table 1 exhibited an IC$_{50}$ value of less than or equal to 1.0 µM for at least one of Aurora kinase A, B or C in the above assay.

Example 217

EGF RTK Enzyme Assay

EGF receptor tyrosine kinase assay utilizes the peptide substrate biotin-ahx-EEEEYFELVAKKK-C(O)NH$_2$ (Advanced Chemtech, # PX9197) as phosphoryl group acceptor.

Assays are performed in 96-well U-bottom plates. The tyrosine kinase domain of the EGF receptor is purchased from Upstate (#14-531). Compounds are diluted in DMSO prior to addition in the assay. Typically, assays are performed by incubating enzyme (0.2-10 nM) with or without inhibitor, 0.1-1 µCi γ$^{33}$P-ATP (Perkin Elmer), 0.1-100 µM ATP, 0.1-10 mM MnCl$_2$, 1-10 µM sodium orthovanadate, 1-10 mM DTT, and 1-100 µM peptide together for the time range of 5-120 min at 37° C. in a final assay volume of 60 µL. The buffer used to bring the final assay volume up to 60 µL is 50 mM MOPS, pH 7.0, containing 1-5% DMSO. Reactions are terminated by addition of 0.2-2 volumes of 0.75% phosphoric acid. Compounds are diluted in DMSO prior to addition in the assay.

Detection of peptide phosphorylation is accomplished by scintillation counting using a beta counter (TopCount) following collection of peptide onto P81 96-well filter plates (Whatman). Total control cpm (C$^+$) and background control cpm (C$^-$) wells contain DMSO instead of compound. Background control (C$^-$) wells lack peptide. Total (C$^+$) minus background (C$^-$) counts are assumed to be proportional to initial reaction velocity. Percent enzyme inhibition are calculated as 1−[(cpm$_{sample}$−C$^-$)/(C$^+$−C$^-$)]×100%. IC$_{50}$ values are determined from % enzyme inhibition vs compound conc. curve plots using GraphPad Prism according to the 4 parameter logistic equation Y=Bottom+(Top−Bottom)/1+10^((LogEC50−X)*HillSlope)) where X is the logarithm of compound concentration and Y is percent inhibition.

Each of the Examples 1-92 in Table 1 exhibited an IC$_{50}$ value of greater than or equal to 3.0 µM this assay.

Example 218

IGF-1 RTK Enzyme Assay

IGF-1 receptor tyrosine kinase assay utilizes the peptide substrate biotin-ahx-EQEDEPEGDYFEWLE-C(O)NH$_2$ (Synpep) as phosphoryl group acceptor.

Assays are performed in 384-well black plates (Nunc). The kinase domain of IGF-1 receptor is purchased from Upstate (cat. no. 14-465M). The enzyme is preactivated on ice for 15 min in the presence of 100 μM ATP and 20 mM MgCl$_2$. Compounds are diluted in DMSO prior to addition in the assay. Typically, assays are performed by incubating enzyme (0.2-10 nM) with or without inhibitor, 30 μM ATP, 5 mM MgCl$_2$, 400 nM peptide and incubated for 40 min at 25° C. in a final assay volume of 20 μL. The assay buffer used is 50 mM Tris-HCl, pH 7.5. Reactions are terminated by addition of 10 μL of 0.15 M EDTA.

Detection of peptide phosphorylation is accomplished by homogenous time-resolved fluorescence (HTRF) following addition of 25 μL Eu-W1024 labeled anti-phosphotyrosine pTyr-100 (Perkin Elmer) antibody (final conc. 20 nM) and 25 μL streptavidin-APC (Perkin Elmer, final conc. 20 nM) in a total volume of 80 μL. Both HTRF detection reagents are diluted in 50 mM Tris-HCl, pH 7.5 buffer containing 0.5% BSA. The assay plate is incubated for 15 min at 25° C. and read in the Envision in time-resolved fluorescence mode with instrument settings for excitation at 340 nm and emission at 665 nM. Total control fluorescence units (C$^+$) and background control rfu (C$^-$) wells contain DMSO instead of compound. Background control (C$^-$) wells lack peptide. Percent enzyme inhibition is calculated as $1-[(cpm_{sample}-C^-)/(C^+-C^-)]\times 100\%$. IC$_{50}$ values are determined from % enzyme inhibition vs compound conc. curve plots using GraphPad Prism™ according to the 4 parameter logistic equation Y=Bottom+(Top−Bottom)/1+10^((LogEC50−X)*HillSlope)) where X is the logarithm of compound concentration and Y is percent inhibition.

Each of the Examples 1-92 in Table 1 exhibited an IC$_{50}$ value of greater than or equal to 3.0 μM this assay.

Example 219

CDK2 Enzyme Assay

CDK2 kinase assay utilizes the peptide substrate Biotin-ahx-ARRPMSPKKKA as phosphoryl group acceptor.

Assays are performed in 96-well U-bottom plates. CDK2 enzyme is purchased from PanVera. Typically, assays are performed by incubating enzyme (0.2-10 nM) with or without inhibitor, 0.1-1 μCi γ$^{33}$P-ATP (Perkin Elmer), 0.1-100 μM ATP, 0.1-10 mM MgCl$_2$, 1-100 μM sodium orthovanadate, 1-10 mM DTT, and 1-100 μM peptide together for the time range of 5-120 min at 25° C. in a final assay volume of 60 μL. The buffer used to bring the final assay volume up to 60 μL is 50 mM Tris-HCl, pH 7.5, containing 1-5% DMSO and 0.1% BSA. Reactions are terminated by addition of 0.2-2 volumes of 0.75% phosphoric acid. Compounds are diluted in DMSO prior to addition in the assay.

Detection of peptide phosphorylation is accomplished by scintillation counting using a beta counter (TopCount) following collection of peptide onto P81 96-well filter plates (Whatman). Total control cpm (C$^+$) and background control cpm (C$^-$) wells contain DMSO instead of compound. Background control (C$^-$) wells lack peptide. Total (C$^+$) minus background (C$^-$) counts are assumed to be proportional to initial reaction velocity. Percent enzyme inhibition is calculated as $1-[(cpm_{sample}-C^-)/(C^+-C^-)]\times 100\%$. IC$_{50}$ values were determined from % enzyme inhibition vs compound conc. curve plots using GraphPad Prism™ according to the 4 parameter logistic equation Y=Bottom+(Top−Bottom)/1+10^((LogEC50-X)*HillSlope)) where X is the logarithm of compound concentration and Y is percent inhibition.

Each of the Examples 1-92 in Table 1 exhibited an IC$_{50}$ value of greater than or equal to 3.0 μM this assay.

Example 220

VEGFR-2 TK Enzyme Assay

VEGFR-2 tyrosine kinase assay utilizes the peptide substrate biotin-ahx-EQEDEPEGDYFEWLE-C(O)NH$_2$ as phosphoryl group acceptor.

The kinase domain of VEGFR-2 is purchased from ProQuinase. The enzyme is preactivated on ice for 15 min in the presence of 100 μM ATP and 20 mM MgCl$_2$. Assays are performed in 96-well U-bottom plates. Typically, assays are performed by incubating enzyme (0.2-10 nM) with or without inhibitor, 30 μM ATP, 5 mM MgCl$_2$, and 400 nM peptide together for 30 min at 25° C. in a final assay volume of 20 μL. The buffer used to bring the final assay volume up to 20 μL is 50 mM Tris-HCl, pH 7.5. Reactions are terminated by addition of 10 μL of 0.15 M EDTA.

Detection of peptide phosphorylation is accomplished by homogenous time-resolved fluorescence (HTRF) following addition of 25 μL Eu-W1024 labeled anti-phosphotyrosine pTyr-100 (Perkin Elmer) antibody (final conc. 20 nM) and 25 μL streptavidin-APC ((Perkin Elmer, final conc. 20 nM) in a total volume of 80 μL. Both HTRF detection reagents are diluted in 50 mM Tris-HCl, pH 7.5 buffer containing 0.5% BSA. The assay plate is incubated for 15 min at 25° C. and read in the Envision in time-resolved fluorescence mode with instrument settings for excitation at 340 nm and emission at 665 nM. Positive control (C$^+$) and negative control (C$^-$) wells contain DMSO instead of compound. Negative control (C$^-$) wells lack peptide. Percent enzyme inhibition is calculated as $1-[(RFU_{sample}-C^-)/(C^+-C^-)]\times 100\%$. IC$_{50}$ values are determined from the % enzyme inhibition vs compound conc. curve plots using GraphPad Prism™ according to the 4 parameter logistic equation Y=Bottom+(Top−Bottom)/1+10^((LogEC50-X)*HillSlope)) where X is the logarithm of compound concentration and Y is percent inhibition.

Each of the Examples 1-92 in Table 1 exhibited an IC$_{50}$ value of greater than or equal to 3.0 μM this assay.

Example 221

In Vitro Cell Proliferation

Compounds are tested for their ability to inhibit cell proliferation and viability. The metabolic reduction of alamarBlue™ (Biosource cat. no. DAL1100) was used to measure cell viability.

The anti-proliferative activity of compounds is studied using a panel of tumor cells: HCT-116 (human colorectal carcinoma cell line), BxPC-3 (human pancreatic adenocarcinoma cell line), A549 (human lung carcinoma cell line), BT-549 (human breast carcinoma cell line), LNCaP (human prostate carcinoma cell line), and MIA Paca-2 (human pancreatic carcinoma cell line). These adherent cells (1,000-20,000) are plated in complete media (RPMI-1640, DMEM, F12K, or McCoy's 5A) containing 10% fetal bovine serum (Gibco) in tissue culture treated 96-well plates (Costar) and placed in a humidified incubator at 37° C., 95% O$_2$, 5% CO$_2$ for 18-24 hr. Media was removed and replaced with 90 μL fresh media. Compound is diluted in media containing 3%

DMSO and added to cells. Background (C⁻) relative fluorescent units are determined by incubating alamarBlue™ reagent for 6 hr using untreated cells plated 18 hr earlier. Untreated cells or cells containing compound are incubated for 96 hr. During the last 6 hr of the incubation period, alamarBlue™ reagent (10 μL) was added to each well and incubated in a humidified incubator at 37° C., 95% $O_2$, 5% $CO_2$.

AlamarBlue™ reduction is measured in a fluorescence plate reader with instrument settings for excitation at 530 nm and emission at 590 nm. Percent inhibition of cell growth was calculated as $1-[(RFU_{sample}-C^-)/(RFU_{untreated}-C^-)] \times 100\%$. Compound $IC_{50}$ values are determined from % inhibition versus compound concentration curve plots using GraphPad Prism™ according to the 4 parameter logistic equation $Y=Bottom+(Top-Bottom)/1+10^{\wedge}((LogEC50-X)*HillSlope))$.

Various compounds in Table 1 exhibited an $IC_{50}$ value of less than or equal to 3.0 μM against one or more of the panel of tumor cells. In particular, Examples 27, 35, 36, 48, 50, 54, 57, 58, and 60 had an $IC_{50}$ value of less than or equal to 3 μM against at least one of HCT-116, MIA Paca-2, or LNCaP cells in using the assay conditions described above.

Drug Combination Pharmacology Studies

While the compounds of the present invention may be used as a single agent, they may also be used as part of a combination therapy. For example, Example 88 when administered as a single agent demonstrated antitumor activity in established human tumor xenografts in athymic mice including tumors derived from pancreas and breast tissues (See single agent dose curves for Example 88 in Examples 222-224 below). To evaluate the therapeutic efficacy of Example 88 in combination with other therapeutic agents and to identify potential synergistic interactions, various studies in animals were performed using Example 88 in combination with Gemcitabine (Gemzar™), erlotinib (Tarceva™), or trastuzumab (Herceptin™).

Gemcitabine, erlotinib, and trastuzumab are therapeutic agents that can treat a spectrum of solid tumors. Each of gemcitabine, erlotinib, and trastuzumab have different proposed mechanisms of action from each other and from the compounds of the present invention. Gemcitabine is an inhibitor of DNA synthesis via inhibition of the enzyme ribonucleotide reductase. Erlotinib is an EGF receptor tyrosine kinase inhibitor that blocks EGF growth factor function. Gemcitabine and erlotinib are currently used for the treatment of advanced pancreatic cancer. Trastuzumab is a recombinant humanized monoclonal antibody that binds and blocks $p185^{HER2}$ receptor function. Trastuzumab is first line treatment for patients with metastatic breast carcinoma whose tumors overexpress the HER2 protein.

Example 222

The antitumor activity of Example 88 administered alone and in combination with erlotinib was evaluated against established human MiaPaCa-2 pancreatic xenografts in athymic mice (a preclinical model of pancreatic cancer). Compounds were dosed on the following schedules:

1) Example 88 was dosed i.p., b.i.d. daily for 10 days (days 1-10).

2) Erlotinib was dosed 50 mg/kg, p.o., daily for 14 days (days 1-14).

The anti-tumor activity was evaluated by inhibition of tumor growth and by assessment of the regression of individual tumors characterized by either partial (greater than 50% reduction in tumor size) or complete responses (100% reduction in tumor size).

Drug treatment started when mean tumor sizes reached approximately 120 mg (day 8). Mice-bearing sc tumors were randomized, and treatment groups consisted of 8 mice. The median tumor size for each group at various points in the study are listed below in Table A.

TABLE A

MiaPaCa-2 Xenograft Model

| Day of Study | Vehicle Median Tumor Size (mg) | Example 88 alone Median Tumor Size (mg) | Erlotinib alone Median Tumor Size (mg) | Example 88 and Erlotinib Median Tumor Size (mg) |
| --- | --- | --- | --- | --- |
| 8 | 113 | 120 | 120 | 120 |
| 10 | 171 | 162 | 144 | 162 |
| 13 | 192 | 170 | 192 | 162 |
| 16 | 241 | 170 | 267 | 108 |
| 20 | 435 | 221 | 363 | 82 |
| 23 | 609 | 209 | 507 | 69 |
| 27 | 988 | 368 | 700 | 88 |
| 30 | 1282 | 486 | 908 | 101 |
| 34 | 1521 | 817 | 1224 | 148 |
| 37 | 1770 | 1055 | 1296 | 225 |
| 42 | 2058 | 1629 | 1368 | 398 |

Figure 1:
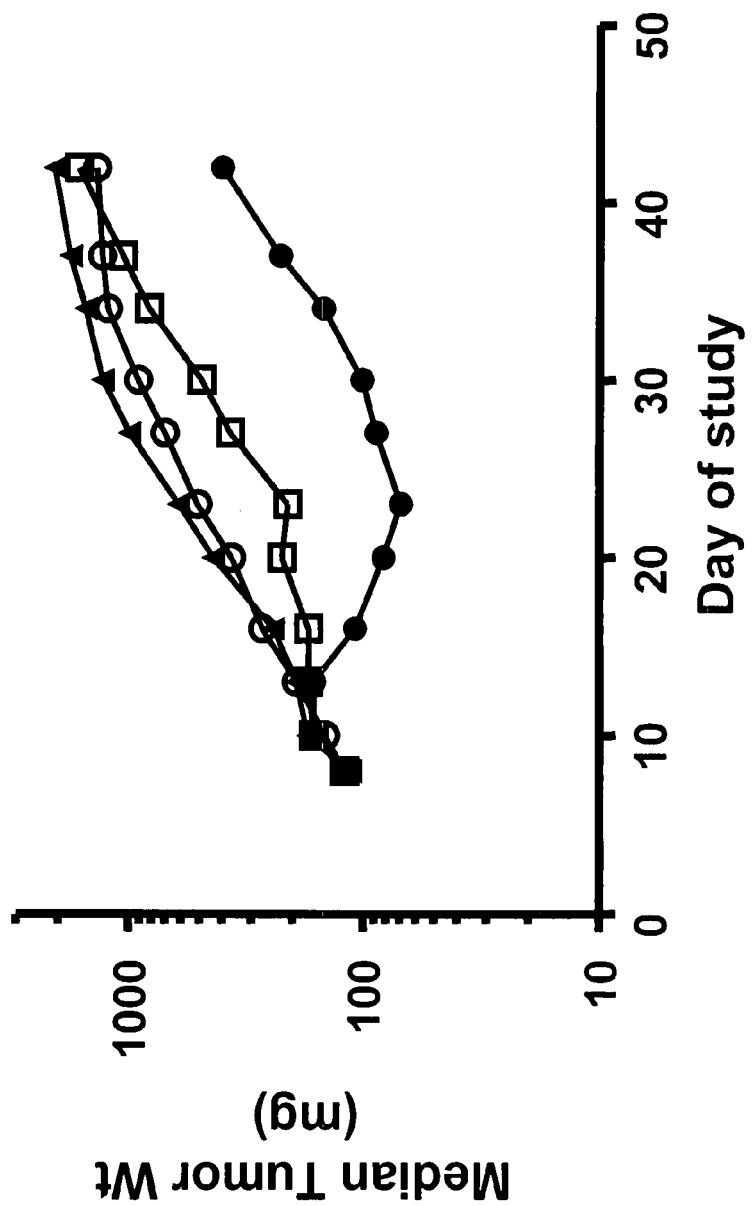
FIG. 1 shows MiaPaCa-2 tumor growth curves, where ▲ represents vehicle for Example 88 and erlotinib; ○ represents erlotinib at a dose of 50 mg/kg, p.o., daily for 14 days; □ represents Example 88 at a dose of 10 mg/kg, i.p., b.i.d. daily for 10 days; and ● represents Example 88 and erlotinib.

The MiaPaCa-2 tumor growth curves are shown in FIG. 1, where

▲—represents vehicle for Example 88 and erlotinib;

○—represents erlotinib at a dose of 50 mg/kg, p.o., daily for 14 days;

☐—represents Example 88 at a dose of 10 mg/kg, i.p., b.i.d. daily for 10 days; and ●—represents Example 88 and erlotinib.

Previous dose response studies in this model found Example 88 (10 mg/kg) was a moderately effective dose for inhibition of tumor growth in this model. Example 88 (10 mg/kg) produced 67% inhibition of tumor growth relative to vehicle-treated tumors on day 23. Erlotinib (50 mg/kg) produced 16% inhibition of tumor growth on day 23. In contrast, the Example 88/erlotinib combination produced 89% inhibition of tumor growth on day 23. Analysis of the individual tumor regression profile on day 42 revealed the Example 88/erlotinib combination therapy produced I partial responder and 2 complete responders out a total of 8 mice (Table AA); however, neither single agent produced a response.

TABLE AA

Example 88 response summary for MIAPaCa-2 xenografts

| Responder Type | Vehicle | Example 91 10 mg/kg | Erlotinib 50 mg/kg | Example 91 + erlotinib |
| --- | --- | --- | --- | --- |
| PR | 0/8 | 0/8 | 0/8 | 1/8 |
| CR | 0/8 | 0/8 | 0/8 | 2/8 |

In summary, Example 88 (10 mg/kg) produced higher antitumor response rates in the MiaPaCa-2 model when combined with erlotinib (50 mg/kg) than when either Example 88 or erlotinib was dosed as a single agent.

Example 223

The antitumor activity of Example 88 administered alone and in combination with gemcitabine was evaluated against established human MiaPaCa-2 pancreatic xenografts in athymic mice (a preclinical model of pancreatic cancer). Compounds were dosed on the following schedules:

1) Example 88 was dosed i.p., b.i.d. daily for 10 days (days 1-10).

2) Gemcitabine was dosed 120 mg/kg, i.p., q3d×4 (days 1, 4, 7, 10).

The anti-tumor activity was evaluated by inhibition of tumor growth, and by assessment of the regression of individual tumors characterized by either partial (greater than 50% reduction in tumor size) or complete responses (100% reduction in tumor size).

Drug treatment started when mean tumor sizes reached approximately 120 mg (day 8). Mice-bearing sc tumors were randomized, and treatment groups consisted of 8 mice. The median tumor size for each group at various points in the study are listed below in Table B.

TABLE B

MiaPaCa-2 Xenograft Model

| Day of Study | Vehicle Median Tumor Size (mg) | Example 88 alone Median Tumor Size (mg) | Gemcitabine alone Median Tumor Size (mg) | Example 88 and gemcitabine Median Tumor Size (mg) |
|---|---|---|---|---|
| 8 | 113 | 120 | 120 | 126 |
| 10 | 144 | 162 | 144 | 144 |
| 13 | 192 | 170 | 144 | 170 |
| 16 | 192 | 170 | 153 | 98 |
| 20 | 295 | 221 | 221 | 69 |
| 23 | 466 | 209 | 246 | 63 |
| 27 | 650 | 368 | 336 | 86 |
| 30 | 757 | 486 | 472 | 149 |
| 34 | 972 | 817 | 675 | 251 |
| 37 | 1132 | 1055 | 824 | 359 |
| 42 | 1353 | 1629 | 988 | 606 |

The MiaPaCa-2 tumor growth curves are shown in FIG. 2, where
- ■—represents vehicle for Example 88 and gemcitabine;
- ▲—represents Example 88 at a dose of 10 mg/kg, i.p., b.i.d. daily for 10 days;
- □—represents gemcitabine at as dose of 120 mg/kg, i.p., q3d×4; and
- ○—represents Example 88 and gemcitabine.

Previous dose response studies in this model found Example 88 (10 mg/kg) was a moderately effective dose for inhibition of tumor growth in this model. Example 88 (10 mg/kg) produced 67% inhibition of tumor growth relative to vehicle-treated tumors on day 23. Gemcitabine (120 mg/kg) produced 60% inhibition of tumor growth on day 23. In contrast, the Example 88/gemcitabine combination produced 90% inhibition of tumor growth on day 23. Analysis of individual tumor regressions on day 42 revealed the Example 88/gemcitabine combination therapy produced 1 partial responder and 1 complete responder out a total of 8 mice; neither single agent produced a response (Table BB).

TABLE BB

Example 88 response summary for MIAPaCa-2 xenografts

| Responder Type | Vehicle | Example 88 10 mg/kg | gemcitabine 120 mg/kg | Example 88 + gemcitabine |
|---|---|---|---|---|
| PR | 0/8 | 0/8 | 0/8 | 1/8 |
| CR | 0/8 | 0/8 | 0/8 | 1/8 |

In summary, Example 88 (10 mg/kg) produced higher anti-tumor response rates in the MiaPaCa-2 model when combined with gemcitabine (120 mg/kg) than when either Example 88 or gemcitabine was dosed as a single agent.

Example 224

Trastuzumab is first line treatment for patients with metastatic breast carcinoma whose tumors overexpress the HER2 protein. Example 88 in combination with trastuzumab was tested in the BT-474 breast xenograft model. The drug treatment started when mean tumor sizes reached approximately 110 mg (day 35 post implantation). Mice-bearing sc tumors were randomized, and treatment groups consisted of 10 mice. Compounds were dosed on the following schedules:

1) Example 88 was dosed 30 mg/kg, i.p., b.i.d. daily for 3 days, then 2 days off, for a total of 5 cycles;

2) Trastuzumab was dosed 10 mg/kg, i.p., twice weekly, for 4 weeks.

The medium tumor size for each group at various points in the study are listed below in Table C.

TABLE C

BT-474 Xenograft Model

| Day of Study | Vehicle Median Tumor Size (mg) | Example 88 alone Median Tumor Size (mg) | Trastuzumab alone Median Tumor Size (mg) | Example 88 and trastuzumab Median Tumor Size (mg) |
|---|---|---|---|---|
| 1 | 113 | 113 | 113 | 113 |
| 4 | 170 | 120 | 133 | 152 |
| 7 | 190 | 152 | 132 | 189 |
| 10 | 259 | 153 | 124 | 225 |
| 14 | 342 | 179 | 106 | 266 |
| 17 | 394 | 149 | 80 | 284 |
| 21 | 504 | 142 | 54 | 384 |
| 24 | 617 | 138 | 36 | 416 |
| 28 | | 104 | 18 | 416 |

The BT-474 tumor growth curves in athymic SCID mice are shown in FIG. 3 where day 1 is when treatment started and where
- ■—represents vehicle for Example 88;
- ○—represents trastuzumab at a dose of 10 mg/kg, i.p., twice weekly, for 4 weeks;
- ▲—represents Example 88 at a dose of 30 mg/kg, i.p., b.i.d. daily for 3 days, then 2 days off, for a total of 5 cycles;
- □—represents Example 88 and trastuzumab.

Example 88 (30 mg/kg) produced 77% inhibition of tumor growth relative to vehicle-treated tumors on day 24. Trastuzumab (10 mg/kg) produced 33% inhibition of tumor growth on day 24. In contrast, the Example 88/trastuzumab combination produced 94% inhibition of tumor growth on day 24. Analysis of the individual tumor regression profile on day 24 revealed the Example 88/trastuzumab combination therapy produced 4 partial responders and 6 complete responders out of a total of 10 mice (Table CC); however, neither single agent produced a response.

TABLE CC

Example 88 response summary for BT-474 xenografts

| Responder Type | Vehicle | Example 88 10 mg/kg | Trastuzumab 10 mg/kg | Example 88 + trastuzumab |
|---|---|---|---|---|
| PR | 0/10 | 0/10 | 0/10 | 4/10 |
| CR | 0/10 | 0/10 | 0/10 | 6/10 |

In summary, the combination of Example 88 (30 mg/kg) and trastuzumab (10 mg/kg) produced a superior complete tumor regression rate when compared with either Example 88 or trastuzumab alone in the BT-474 xenograft model.

The following procedures are for preparing pharmaceutical formulation containing a compound of the present invention.

Example 225

A pharmaceutical formulation containing 2.0 mg/mL of Example 88 (which is equivalent to 2.7 mg/mL of Example 88 as a trihydrochloride salt) was prepared as follows.

Example 88 as a trihydrochloride salt (1.350 gr) was dissolved with stirring in Sterile Water For Injection (SWFI). The SWFI may be degassed with sterile nitrogen gas prior to use. The amount of SWFI into which Example 88 is dissolved is an amount into which the compound will dissolve. In one embodiment, the amount of SWFI into which the compound is dissolved is above 50% of the final volume and may be 75% of the final volume.

D-Mannitol was added to the solution and dissolved with stirring. Prior to the addition of mannitol or after dissolving the mannitol, the pH of the mixture is adjusted to between 3.0 and 3.6±0.1 with gradual addition of small amounts of a basic solution such as 1 N NaOH. SWFI was then added to the final required volume of 500 mL.

The solution was filtered through a 0.22 μm PVDF filter into a container. A 0.45 μm PVDF may be used to pre-filter the solution. Finally, 10.25 mL of the filtered solution was transferred into 20 mL vials (Type I boro-silicate glass vials) that had been flushed with sterile nitrogen gas prior to use. The filled vials were then stoppered using Fluorotec B2-40 stoppers. The vials may be stored at or below 8° C. and above freezing.

Example 226

Using a procedure similar to the one in Example 225, a 7 mg/mL ±0.3 solution of Example 88 may be prepared where the pH of the final solution is pH 2.5 to 3.0±0.1 and the final volume in each vial is 35 mL. The vials may be stored at or below 8° C. and above freezing.

Example 227

A diluent for use in combination with a formulation of Examples 225 or with other formulations containing a compound of the present invention may be prepared as follows.

SWFI (490 mL) that was degassed with sterile nitrogen gas was transferred into a container and the pH was adjusted to pH 11.0 to 11.4+0.1. SWFI was then added to the final required volume of 500 mL. The solution was then filtered through a 0.22 μm PVDF filter into a 0.22 μm PVDF filter into a container. Finally, 10.25 mL of the filtered solution was transferred into 20 mL vials (Type I boro-silicate glass vials) that had been flushed with sterile nitrogen gas prior to use.

Example 228

Using a procedure similar to the one in Example 227, a diluent was prepared having a pH 11.0 to 11.4 ±0.1 and where 65 mL of filtered solution was transferred into 100 mL vials.

Example 229

Prior to administration, the formulation in Example 225 was diluted with the diluent in Example 227 where the contents the diluent (10.25 mL) were transferred in small amounts into the vial containing Example 225 such that the final concentration of Example 88 was 1 mg/mL and the final pH was 5.5±0.1. The combined solution showed no precipitate and was stabile at between 15 to 30° C. for a sufficient period to enable dose preparation and dosing. Such a period was at least 1 to 6 hours.

Example 230

Prior to administration, the formulation in Example 226 was diluted with the diluent in Example 228 where the contents the diluent (65 mL) were transferred in small amounts into the vial containing Example 226 such that the final concentration of Example 88 was 2 mg/mL and the final pH was 4.5±0.1. The combined solution showed no precipitate and was stabile at between 15 to 30° C. for a sufficient period to enable dose preparation and dosing. Such a period was at least 1 to 6 hours and may be as long as 24 hours.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated for an Aurora kinase mediated disorder. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

We claim:
1. A compound of Formula (I):

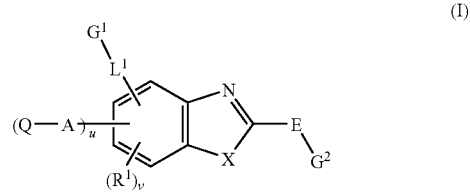

wherein
 X is —NH—,
 E is —NH—,
 $G^1$ is selected from the group consisting of: 1H-indazole-5-yl and 1H-indazole-6-yl,
  wherein $G^1$ is optionally substituted 1-4 times with a substituent selected from the group consisting of $R^b$, 4-($C_{1-10}$alkyl)-piperazine-1-yl, and —NHC(O)-(1-($C_{1-10}$alkyl)-piperidine-4-yl;
 $G^2$ is selected from the group consisting of: phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, and 4,5,6,7-tetrahydro-thiazolo[5,4-c]-pyridine-2-yl,
  wherein $G^2$ is optionally substituted 1-4 times with a substituent selected from the group consisting of $R^b$ and 4-($C_{1-10}$alkyl)-piperazine-1-yl;
 $L^1$ is —C(O)—NH— or —NH—C(O)—
 A is a direct bond or the group -$L^2$-Y-$L^3$-, wherein $L^2$ and $L^3$ are independently selected from the group consisting of:
  a direct bond,
  —$C_{1-10}$ alkylene,
  —$C_{2-10}$ alkenylene,
  —$C_{2-10}$ alkynylene,
  -arylene,
  -heteroarylene,
  -cycloalkylene, and
  -heterocyclylene,
  wherein the carbon atoms of the alkylene, alkenylene, alkynylene, arylene, heteroarylene, cycloalkylene, and heterocyclylene groups are optionally substituted 1-4 times with a substituent independently selected from $R^c$;
Y is a direct bond, —O—, —N($R^{10}$), —S—, $SO_2$—, —C(O)N($R^{10}$)—, —N($R^{10}$)—C(O)—, —N($R^{11}$)C(O)N($R^{10}$)—, —N($R^{10}$)$SO_2$—, —$SO_2$N($R^{10}$)—, —C(O)—O—, —N($R^{11}$)$SO_2$N($R^{10}$)—, —O—CO—, or —N=N—,
  wherein
    $R^{10}$ and $R^{11}$ are independently selected from the group consisting of: $R^d$ and $R^e$, and
Q is selected from the group consisting of

1)

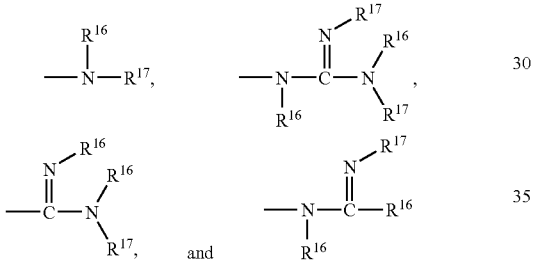

wherein $R^{16}$ and $R^{17}$ are independently selected from the group consisting of: $R^d$ and $R^e$;
2) -heteroaryl;
  -heterocyclyl;
  -fused cycloalkylheteroaryl;
  -fused heterocyclylaryl;
  -fused heterocyclylheteroaryl;
  -fused arylheterocyclyl;
  -fused heteroarylcycloalkyl; and
  -fused heteroarylheterocyclyl;
  wherein the heteroaryl, heterocyclyl, fused cycloalkylheteroaryl, fused heterocyclylaryl, fused heterocyclylheteroaryl, fused arylheterocyclyl, fused heteroarylcycloalkyl, and fused heteroarylheterocyclyl groups are optionally substituted 1-4 times with a substituent independently selected from $R^c$; and
3) a ring system comprising at least one nitrogen atom selected from the group consisting of:

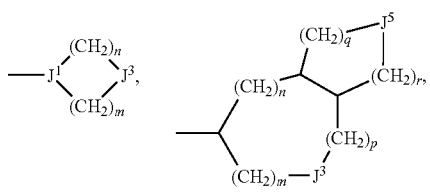

-continued

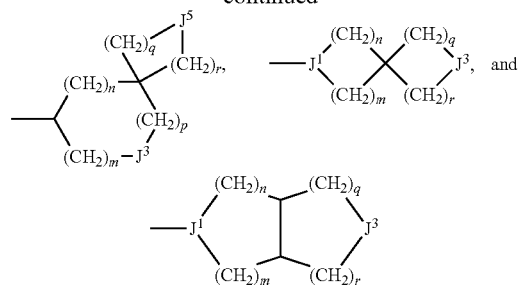

wherein
  n, m, p, q and r are independently 0-4 such that n+m+p equals from 2-5 and q+r equals from 2-5, and the cycloalkyl or heterocyclo ring system is optionally substituted on the ($CH_2$) carbon atoms 1-2 with $R^{18}$ or $R^{19}$, wherein $R^{18}$ and $R^{19}$ are independently selected from the group consisting of $R^f$ and $R^g$,
$J^1$ is selected from the group consisting of:

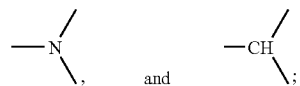

$J^3$ and $J^5$ are independently selected from the group consisting of —$CH_2$—, —O—, —S—, —S(O)$_2$—, —C(O)—, —C(O)N(H)—, —NHC(O)—, —NHC(O)N(H)—, —$NHSO_2$—, —$SO_2$N(H)—, —C(O)—O—, —O—C(O)—, —$NHSO_2$NH—,

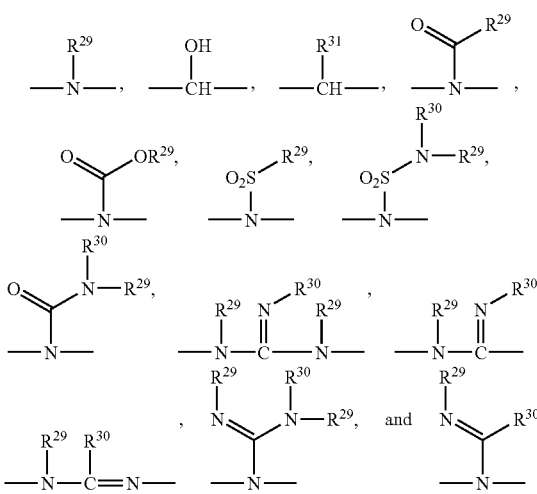

$R^{29}$ and $R^{30}$ are independently selected from the group consisting of $R^d$ and $R^e$;
$R^{31}$ is $R^f$; and
$R^1$ is $R^b$;
$R^b$ is
  a) -cycloalkyl,
  b) -cyano,
  c) —$OR^d$,
  d) —$NO_2$,
  e) -halogen,
  f) -haloalkyl,
  g) —S(O)$_s R^d$, h) —SR$^d$,
i) —S(O)$_2$OR$^d$,
j) —S(O)$_n$NR$^d$R$^e$,
k) —NR$^d$R$^e$,
l) —O(CR$^f$R$^g$)$_t$NR$^d$R$^e$,
m) —C(O)R$^d$,
n) —CO$_2$R$^d$,
o) —CO$_2$(CR$^f$R$^g$)$_t$C(O)NR$^d$R$^e$,
p) —OC(O)R$^d$,
q) —C(O)NR$^d$R$^e$,
r) —NR$^d$C(O)R$^e$,
s) —OC(O)NR$^d$R$^e$,
t) —NR$^d$C(O)OR$^e$,
u) —NR$^d$C(O)NR$^d$R$^e$,
v) —CF$_3$,
w) —OCF$_3$
x) —C$_{1-10}$ alkyl,
y) —C$_{2-10}$ alkenyl,
z) —C$_{2-10}$ alkynyl,
aa) —C$_{1-10}$ alkylene-aryl,
bb) —C$_{1-10}$ alkylene-heteroaryl, or
cc) -heteroaryl,
wherein alkyl, alkenyl, alkynyl, aryl, heteroaryl, and cycloalkyl groups are optionally substituted 1-4 times with a substituent independently selected from R$^c$; or
R$^b$ is phenyl;
R$^c$ is
a) -halogen,
b) -amino,
c) -carboxy,
d) —C$_{1-4}$ alkyl,
e) —O—C$_{1-4}$ alkyl,
f) -cycloalkyl,
g) —O-cycloalkyl,
h) -aryl,
i) —C$_{1-4}$ alkylene-aryl,
j) -hydroxy,
k) —CF$_3$,
l) —O-aryl,
m) -heteroaryl,
n) -heteroaryl-C$_{1-10}$ alkyl,
o) heterocyclyl,
p) —CO$_2$—C$_{1-10}$ alkyl, or
q) —CO$_2$—C$_{1-10}$ alkyl-aryl,
R$^d$ and R$^e$ are independently selected from the group consisting of hydrogen, C$_{1-10}$ alkyl, C$_{2-10}$ alkenyl, C$_{2-10}$ alkynyl, cycloalkyl, —C$_{1-10}$ alkylene-cycloalkyl, aryl and heterocyclyl, wherein alkyl, alkenyl, alkynyl, cycloalkyl, aryl and heterocyclyl groups are optionally substituted with one to four substituents independently selected from R$^c$; or R$^d$ and R$^e$ together with the atoms to which they are attached form a heterocyclic ring of 5 to 7 members containing 0-2 additional heteroatoms independently selected from oxygen, sulfur and nitrogen and optionally substituted with 1-3 times with R$^c$,
R$^f$ and R$^g$ are independently selected from the group consisting of hydrogen, C$_{1-10}$ alkyl, cycloalkyl, —C$_{1-10}$ alkylene-cycloalkyl, and aryl, wherein alkyl, cycloalkyl, and aryl groups are optionally substituted with one to four substituents independently selected from R$^c$; or R$^f$ and R$^g$ together with the carbon to which they are attached form a ring of 5 to 7 members containing 0-2 heteroatoms independently selected from oxygen, sulfur and nitrogen optionally substituted with 1-3 times with R$^c$,
s is an integer from 1 to 2,
t is an integer from 1 to 10,
u is an integer from 0 to 1,
v is an integer from 0 to 2,
or a pharmaceutically acceptable salt or prodrug thereof.

2. The compound of Formula (I) in claim 1 or a pharmaceutically acceptable salt thereof, wherein G$^2$ is substituted with at least one substituent selected from the group consisting of: halo, phenyl, C$_{1-10}$ alkyl, piperazine-1-yl, 4-(C$_{1-10}$ alkyl)-piperazine-1-yl, C$_{1-10}$ alkoxy, haloalkyl, cycloalkyl, and C$_{1-10}$ alkylene-cycloalkyl.

3. The compound of Formula (I) in claim 1 or a pharmaceutically acceptable salt thereof, wherein G2 is phenyl, naphthyl, isoquinolin-3-yl, pyridine-2-yl, pyridine-3-yl, pyridine-4-yl, thiophen-2-yl, thiazole-2-yl, imidazole-2-yl or benzothiazole-2-yl,
wherein G$^2$ is unsubstituted or substituted with at least one substituent selected from the group consisting of: chloro, fluoro, methyl, ethyl, propyl, isopropyl, tert-butyl, butyl, phenyl, methoxy, trifluoromethyl, trifluoromethoxy, and cyclopentyl.

4. The compound of Formula (I) in claim 1 or a pharmaceutically acceptable salt thereof, wherein G$^1$ is unsubstituted or substituted with at least one group selected from the group consisting of: halo, phenyl, C$_{1-10}$ alkyl, piperazine-1-yl, 4-(C$_{1-10}$ alkyl)-piperazine-1-yl, —C$_{1-10}$ alkoxy, —C$_{1-10}$ alkylene-OH, -haloalkyl, -cycloalkyl, —C$_{1-10}$ alkylene-cycloalkyl, morpholine-4-yl, —C$_{1-10}$-alkylene-morpholine-4-yl, pyrrole-1-yl, -amino, —NH—(C$_{1-10}$ alkyl), —N(C$_{1-10}$ alkyl)$_2$, —NHC(O)—C$_{1-10}$ alkyl, —NHC(O)-1-(C$_{1-10}$ alkyl)-piperidine-4-yl), —NHC(O)-phenyl, —NH—C$_{1-10}$ alkylene-morpholine-4-yl, —O—C$_{1-10}$ alkylene-morpholine-4-yl, and —NH—C$_{1-10}$ alkylene-OH.

5. The compound of Formula (I) in claim 1 or a pharmaceutically acceptable salt thereof, wherein G$^1$ is 1H-indazole-5-yl or 1H-indazole-6-yl,
wherein G$^1$ is unsubstituted or substituted at the 3-position with a substituent selected from the group consisting of: halo, phenyl, C$_{1-10}$ alkyl, piperazine-1-yl, 4-(C$_{1-10}$ alkyl)-piperazine-1-yl, —C$_{1-10}$ alkoxy, —C$_{1-10}$ alkylene-OH, -haloalkyl, -cycloalkyl, —C$_{1-10}$ alkylene-cycloalkyl, morpholine-4-yl, —C$_{1-10}$-alkylene-morpholine-4-yl, pyrrole-1-yl, -amino, —NH—(C$_{1-10}$ alkyl), —N(C$_{1-10}$ alkyl)$_2$, —NHC(O)—C$_{1-10}$ alkyl, —NHC(O)-(1-(C$_{1-10}$ alkyl)-piperidine-4-yl), —NHC(O)-phenyl, —NH—C$_{1-10}$ alkylene-morpholine-4-yl, —O—C$_{1-10}$ alkylene-morpholine-4-yl, and —NH—C$_{1-10}$ alkylene-OH.

6. The compound of Formula (I) in claim 1 or a pharmaceutically acceptable salt thereof, wherein
u is 1,
A is a direct bond, and
Q is selected from the group consisting of: 4-(C$_{1-10}$ alkyl)-piperazine-1-yl, piperadine-1-yl, morpholine-4-yl, —NH—C$_{1-10}$ alkyl, —N—(C$_{1-10}$ alkyl)$_2$, —N—(C$_{1-10}$ alkyl)(cycloalkyl), and —NH-cycloalkyl.

7. The compound of Formula (I) in claim 1 or a pharmaceutically acceptable salt thereof, wherein u is zero and v is zero.

8. The compound of Formula (I) in claim 1 or a pharmaceutically acceptable salt thereof, wherein u is 1 and v is zero.

9. The compound of Formula (I) in claim 1 or a pharmaceutically acceptable salt thereof, wherein u is zero and v is one.

10. The compound of Formula (I) in claim 1 or a pharmaceutically acceptable salt thereof, wherein
u is zero,
v is one, and
R$^1$ is selected from the group consisting of: —C$_{1-10}$ alkyl, -cycloalkyl, —C$_{1-10}$ alkylene-cycloalkyl, —C$_{1-10}$ haloalkyl, -phenyl, —O—C$_{1-10}$ alkyl, —O-cycloalkyl, and —O—C$_{1-10}$ haloalkyl.

11. The compound of Formula (I) in claim 1 or a pharmaceutically acceptable salt thereof, wherein
X is —NH—,
E is —NH—,
v is zero,
L¹ is —NHC(O)— or —C(O)NH—,
G¹ is 1H-indazol-6-yl or 1H-indazol-5-yl,
wherein G¹ is optionally substituted 1-4 times with a substituent selected from the group consisting of $R^b$.

12. The compound of Formula (I) in claim 11 or a pharmaceutically acceptable salt thereof, wherein G¹ is unsubstituted.

13. The compound of Formula (I) in claim 1 or a pharmaceutically acceptable salt thereof having the formula:

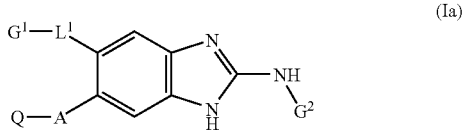

(Ia)

wherein
G¹, G², L¹, Q, and A are as defined in claim 1.

14. The compound of Formula (I) in claim 1 or a pharmaceutically acceptable salt thereof having the formula:

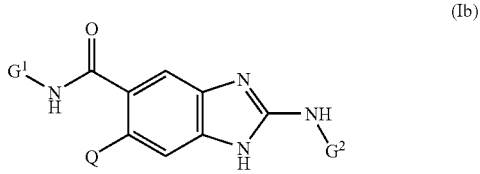

(Ib)

wherein
G¹, G², and Q are as defined in claim 1.

15. The compound of Formula (Ib) in claim 14 or a pharmaceutically acceptable salt thereof, wherein
Q is selected from the group consisting of: 4-($C_{1-10}$ alkyl)-piperazine-1-yl, piperadine-1-yl, morpholine-4-yl, —NH—$C_{1-10}$ alkyl, —N—($C_{1-10}$ alkyl)₂, —N—($C_{1-10}$ alkyl)(cycloalkyl), and —NH-cycloalkyl.

16. The compound of Formula (Ib) in claim 14 or a pharmaceutically acceptable salt thereof, wherein
G² is selected from the group consisting of: phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, and 4,5,6,7-tetrahydro-thiazolo[5,4-c]-pyridine-2-yl,
wherein G² is optionally substituted 1-4 times with a substituent selected from the group consisting of $R^b$.

17. The compound of Formula (I) in claim 1 or a pharmaceutically acceptable salt thereof having the formula:

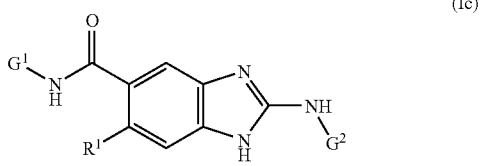

(Ic)

wherein
G¹, G², and R¹ are as defined in clam 1.

18. The compound of Formula (Ic) in claim 17 or a pharmaceutically acceptable salt thereof, wherein
R¹ is selected from the group consisting of: —$C_{1-10}$ alkyl, -cycloalkyl, —$C_{1-10}$ alkylene-cycloalkyl, —$C_{1-10}$ haloalkyl, -phenyl, —O—$C_{1-10}$ alkyl, —O-cycloalkyl, and —O—$C_{1-10}$ haloalkyl.

19. The compound of Formula (Ic) in claim 17 or a pharmaceutically acceptable salt thereof, wherein
G² is selected from the group consisting of: phenyl, naphthyl, isoquinolin-3-yl, pyridine-2-yl, pyridine-3-yl, pyridine-4-yl, thiophen-2-yl, thiazole-2-yl, imidazole-2-yl, benzothiazole-2-yl, and 4,5,6,7-tetrahydro-thiazolo[5,4-c]-pyridine-2-yl,
wherein G² is optionally substituted 1-4 times with a substituent selected from the group consisting of $R^b$.

20. The compound of Formula (I) in claim 1 selected from the group consisting of: 4-[6-(1H-Indazol-6-ylcarbamoyl)-2-(2-trifluoromethylphenylamino)-3H-benzimidazol-5-yl]-piperazine-1-carboxylic acid tert-butyl ester, 6-piperazin-1-yl-2-(2-trifluoromethylphenylamino)-1H-benzimidazole-5-carboxylic acid (1H-indazol-6-yl)-amide, 4-[6-(1H-Indazol-6-ylcarbamoyl)-2-(3-methylpyridin-2-ylamino)-3H-benzimidazol-5-yl]-piperazine-1-carboxylic acid tert-butyl ester, and 2-(3-Methylpyridin-2-ylamino)-6-piperazin-1-yl-1H-benzimidazole-5-carboxylic acid (1H-indazol-6-yl)-amide, or a pharmaceutically acceptable salt thereof.

21. A pharmaceutical composition comprising a compound of Formula (I) in claim 1 or a pharmaceutically acceptable salt thereof, and a pharmaceutically acceptable carrier.

22. The pharmaceutical composition of claim 21 comprising a therapeutically effective amount of the compound of Formula (I) or a pharmaceutically acceptable salt thereof.

23. The pharmaceutical composition of claim 21 further comprising an additional therapeutic agent selected from the group consisting of antimetabolites, protein tyrosine kinase inhibitors, and antibodies.

24. 6-piperazin-1-yl-2-(2-trifluoromethylphenylamino)-1H-benzimidazole-5-carboxylic acid (1H-indazol-6-yl)-amide or a pharmaceutically acceptable salt thereof.

25. 6-piperazin-1-yl-2-(2-trifluoromethylphenylamino)-1H-benzimidazole-5-carboxylic acid (1H-indazol-6-yl)-amide.

26. 6-piperazin-1-yl-2-(2-trifluoromethylphenylamino)-1H-benzimidazole-5-carboxylic acid (1H-indazol-6-yl)-amide trihydrochloride salt.

27. A pharmaceutical composition comprising 6-piperazin-1-yl-2-(2-trifluoromethylphenylamino)-1H-benzimidazole-5-carboxylic acid (1H-indazol-6-yl)-amide or a pharmaceutically acceptable salt thereof, and a pharmaceutically acceptable carrier, excipient, diluent, or a mixture thereof.

28. The pharmaceutical composition of claim 27, wherein the pharmaceutical composition is in the form of a liposome.

* * * * *